United States Patent
Kim

(10) Patent No.: US 10,787,650 B2
(45) Date of Patent: Sep. 29, 2020

(54) ARTIFICIAL BIOLUMINESCENT ENZYMES

(71) Applicant: NATIONAL INSTITUTE OF ADVANCED INDUSTRIAL SCIENCE AND TECHNOLOGY, Tokyo (JP)

(72) Inventor: Sung Bae Kim, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 57 days.

(21) Appl. No.: 15/763,779

(22) PCT Filed: Sep. 30, 2016

(86) PCT No.: PCT/JP2016/079160
§ 371 (c)(1),
(2) Date: Mar. 27, 2018

(87) PCT Pub. No.: WO2017/057752
PCT Pub. Date: Apr. 6, 2017

(65) Prior Publication Data
US 2018/0265850 A1   Sep. 20, 2018

(30) Foreign Application Priority Data
Sep. 30, 2015   (JP) .................... 2015-194788

(51) Int. Cl.
| C12N 9/02 | (2006.01) |
| C12N 15/53 | (2006.01) |
| C12N 15/62 | (2006.01) |
| C12N 1/20 | (2006.01) |
| C12N 5/10 | (2006.01) |
| C12Q 1/66 | (2006.01) |
| G01N 33/543 | (2006.01) |
| C12N 15/09 | (2006.01) |
| C12Q 1/26 | (2006.01) |
| C07K 19/00 | (2006.01) |
| G01N 21/76 | (2006.01) |
| G01N 33/535 | (2006.01) |

(52) U.S. Cl.
CPC ............ *C12N 9/0069* (2013.01); *C07K 19/00* (2013.01); *C12N 5/10* (2013.01); *C12N 15/09* (2013.01); *C12Q 1/26* (2013.01); *C12Y 113/12005* (2013.01); *G01N 21/763* (2013.01); *G01N 33/535* (2013.01); *G01N 33/543* (2013.01); *C07K 2319/01* (2013.01)

(58) Field of Classification Search
None
See application file for complete search history.

(56) References Cited

U.S. PATENT DOCUMENTS

| 2015/0284813 A1 | 10/2015 | Kim et al. |
| 2016/0281129 A1 | 9/2016 | Kim et al. |

FOREIGN PATENT DOCUMENTS

| JP | 2007-508014 A | 4/2007 |
| JP | 2011-067190 A | 4/2011 |
| JP | 2012-249619 A | 12/2012 |
| JP | 2014-085311 A | 5/2014 |
| JP | 2014-100137 A | 6/2014 |
| WO | WO 2005/038029 A2 | 4/2005 |
| WO | WO 2014/065047 A1 | 5/2014 |
| WO | WO 2015/056762 A1 | 4/2015 |

OTHER PUBLICATIONS

Nishihara, R., "Synthetic Coelenterazine Derivatives for Bioluminescent Imaging", Ph.D. Thesis, Graduate School of Science and Technology, Keio University, 2017 (Year: 2017).*
Dictionary definition of "represent", obtained from Merriam-Webster online, 1 page, last viewed on Jan. 11, 2018 (Year: 2018).*
Inouye et al., "Overexpression, purification and characterization of the catalytic component of *Oplophorus* luciferase in the deep-sea shrimp, *Oplophorus gracilirostris*," Protein Expr. Purif., 56(2): 261-268 (2007).
Kim et al., "Molecular Tension-Indexed Bioluminescent Probe for Determining Protein—Protein Interactions," Bioconjug. Chem., 20(12): 2324-2330 (2009).
Kim et al., "Creation of Artificial Luciferases for Bioassays," Bioconjug. Chem., 24(12): 2067-2075 (2013).
Kim et al., "Functional artificial luciferases as an optical readout for bioassays," Biochem. Biophys. Res. Commun., 448(4): 418-423 (2014).
Loening et al., "A red-shifted *Renilla* luciferase for transient reporter-gene expression," Nat. Methods, 7(1): 5-6 (2010).
Ozawa et al., "Advances in Fluorescence and Bioluminescence Imaging," Anal. Chem., 85(2): 590-609 (2013).

(Continued)

Primary Examiner — David Steadman
(74) Attorney, Agent, or Firm — Leydig, Voit & Mayer, Ltd.

(57) ABSTRACT

The invention relates to provision of artificial bioluminescent enzymes. The invention provides for a polypeptide, including any one of amino acid sequences (i) to (iii) below, and having luciferase activity: (i) an amino acid sequence of SEQ ID NO: 1; (ii) an amino acid sequence of SEQ ID NO: 1 in which 1 to 10 amino acids are substituted, added, or deleted; or (iii) an amino acid sequence having at least 95% sequence identity to the amino acid sequence of SEQ ID NO: 1.

18 Claims, 23 Drawing Sheets

Specification includes a Sequence Listing.

(56) References Cited

OTHER PUBLICATIONS

Shimomura, "Bioluminescence: Chemical Principles and Methods" (published by World Scientific Publishing Co. Pte. Ltd., Singapore, 2006), pp. i-xxvii (Preface, Table of Contents, and Introduction).

Takenaka et al., "Two forms of secreted and thermostable luciferases from the marine copepod crustacean, *Metridia pacifica*," *Gene*, 425(1-2): 28-35 (2008).

Takenaka et al., "Evolution of Bioluminescence in Marine Planktonic Copepods," *Mol. Evol. Biol.*, 29(6): 1669-1681 (2012).

Takenaka et al., "Computational analysis and functional expression of ancestral copepod luciferase," *Gene*, 528(2): 201-205 (2013).

Wang et al., "Quantum Yields and Quantitative Spectra of Firefly Bioluminescence with Various Bivalent Metal Ions," *Phochem. Photobiol.*, 87(4): 846-852 (2011).

Japanese Patent Office, International Search Report in International Patent Application No. PCT/JP2016/079160 (dated Jan. 10, 2017).

\* cited by examiner (A) native CTZ (nCTZ)

(B) native CTZ (nCTZ)

(C)

(D)

(A)

(B)

(A)

(B)

(A)

(B)

(C) Western blot (A)

ARTIFICIAL BIOLUMINESCENT ENZYMES

CROSS-REFERENCE TO RELATED APPLICATIONS

This patent application is the U.S. national phase of International Patent Application No. PCT/JP2016/079160, filed Sep. 30, 2016, which claims the benefit of Japanese Patent Application No. 2015-194788, filed on Sep. 30, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 63,760 bytes ASCII (Text) file named "73871Replacement-SequenceListing," created Jan. 27, 2020.

TECHNICAL FIELD

The present invention relates to novel artificial bioluminescent enzymes.

BACKGROUND ART

Curiosity about luminescence emitted by luminescent organisms is so old a theme as to be described even in a document from the third century BCE. However, it was not until the 20th century that an actual chemical principle of bioluminescence was elucidated (Non Patent Literature 1).

With regard to practical utilization of bioluminescence, applications have rapidly expanded after successful gene cloning of a luminescent enzyme from a luminescent organism. A history of bioluminescence research has taken the following course in recent 20 years. First, a bioluminescent enzyme is established from nature, and the luminescent enzyme is made into a luminescent probe with a gene recombination technology. Further, the research has been advanced with a view to applying the luminescent probe to bioimaging and a diagnostic apparatus. Those three have served as three pillars for bioluminescence to support the field of bioluminescence.

Bioluminescence provides distinctive bioanalytical benefits, such as a low background intensity, a high signal-to-noise (S/N) ratio, a wide dynamic range of signals, and suitability in bioimaging (Non Patent Literature 2). Bioluminescence is generated by bioluminescent enzymes and "photoproteins", such as $Ca^{2+}$-sensitive aequorins obtained from luminescent organisms. Many researchers have been devoted to creating novel bioluminescent enzymes having excellent optical properties and functionalities for facilitating their applications to bioanalysis as optical readouts (Non Patent Literatures 3 and 4).

Through a series of researches conducted by Takenaka et al., luminescent zooplankton were collected at the southern deep-sea of Hokkaido and various natural luminescent enzymes were established. First, 2 kinds of luminescent enzymes were able to be established in 2008 (Non Patent Literature 5), 11 kinds of luminescent enzymes were able to be established in 2012 (Non Patent Literature 6 and Patent Literature 1), and 12 kinds of luminescent enzymes were able to be established in 2013 (Non Patent Literature 10). With the establishment of those natural luminescent enzymes, the number of copepoda luminescent enzymes on databases reached 25 kinds.

It has long been a dream of luminescence researchers to create a bioluminescence reaction system that emits light with a higher luminescence intensity and higher stability.

In recent years, the inventors of the present invention established a series of artificial bioluminescent enzymes (Artificial Luciferases: ALucs) through extraction of frequently occurring amino acids from multiple sequence alignment of copepod bioluminescent enzymes from zooplankton samples collected at the southern deep-sea of Hokkaido (13 kinds) and other existing bioluminescent enzymes (2 kinds) (Non Patent Literatures 4 and 7, and Patent Literature 2). In addition, peripheral technology researches regarding substrates and reaction solutions that contribute to optimal luminescence reactions of those artificial bioluminescent enzymes were conducted (Patent Literatures 3 and 4). It is known that copepod bioluminescent enzymes generally share a high homology with each other, and are phylogenetically close to *Oplophorus* bioluminescent enzymes (OLucs) from deep-sea shrimp (see FIG. 1).

ALuc30, which was one of the ALucs established by the inventors of the present invention, was analyzed for unique supersecondary structure codes (SSCs) of all constituent amino acids of the protein. As a result, it was revealed that a helix-loop-helix structure, which resembled a typical "EF-hand" common to $Ca^{2+}$-binding proteins (calmodulin and aequorins), was present in the sequence (Non Patent Literature 7) (see FIG. 2 and FIG. 3). A bioluminescent enzyme that emits bioluminescence in a cation-dependent manner has been previously reported: e.g., beetle bioluminescent enzymes require $Mg^{2+}$ as a cofactor, which can be substituted for various divalent cations (Non Patent Literature 8). In addition, it has been previously reported that a luminescence intensity of OLuc is inhibited by several multivalent cations, but the mechanism is unclear (Non Patent Literature 9).

Such previous researches have suggested that a luminescence activity of a bioluminescent enzyme strongly depends on kinds and concentrations of reaction solution additives, in particular, cations.

CITATION LIST

Patent Literature

PTL 1: JP 2012-249619 A
PTL 2: JP 2014-100137 A
PTL 3: WO 2015/056762 A1
PTL 4: JP 2014-085311 A

Non-Patent Literature

NPL 1: Shimomura, O., Bioluminescence. 2006, Singapore: World Scientific Publishing Co. Pte. Ltd.
NPL 2: Ozawa, T., H. Yoshimura, and S. B. Kim, Advances in Fluorescence and Bioluminescence Imaging. Anal. Chem., 2013. 85(2): p. 590-609.
NPL 3: Loening, A. M., A. Dragulescu-Andrasi, and S. S. Gambhir, A red-shifted *Renilla* luciferase for transient reporter-gene expression. Nat. Methods, 2010. 7(1): p. 5-6.
NPL 4: Kim, S. B., M. Torimura, and H. Tao, Creation of artificial luciferases for bioassays. Bioconjugate Chem., 2013. 24: p. 2067-2075.

NPL 5: Takenaka, Y., et al., Two forms of secreted and thermostable luciferases from the marine copepod crustacean, *Metridia pacifica*. Gene, 2008. 425(1-2): p. 28-35.

NPL 6: Takenaka, Y., et al., Evolution of Bioluminescence in Marine Planktonic Copepods. Mol. Biol. Evol., 2012. 29(6): p. 1669-1681.

NPL 7: Kim, S. B. and H. Izumi, Functional artificial luciferases as an optical readout for bioassays. Biochem. Biophys. Res. Comm., 2014. 448(4): p. 418-423.

NPL 8: Wang, Y., et al., Quantum Yields and Quantitative Spectra of Firefly Bioluminescence with Various Bivalent Metal Ions. Photochemistry and Photobiology, 2011. 87(4): p. 846-852.

NPL 9: Inouye, S. and S. Sasaki, Overexpression, purification and characterization of the catalytic component of *Oplophorus* luciferase in the deep-sea shrimp, *Oplophorus gracilirostris*. Protein Expression and Purification, 2007. 56(2): p. 261-268.

NPL 10: Yasuhiro, T., et al., Computational analysis and functional expression of ancestral copepod luciferase. Gene. 2013 Oct. 10; 528(2): 201-205

NPL 11: Kim, S. B., M. Sato, and H. Tao, Molecular Tension-Indexed Bioluminescent Probe for Determining Protein-Protein Interactions. Bioconjugate Chem., 2009. 20(12): p. 2324-2330.

SUMMARY OF INVENTION

Technical Problem

It has long been a dream of relevant researchers to create a "bioluminescent enzyme system having a variation in luminescence intensity and showing high stability while having a small molecular weight." However, existing bioluminescent enzymes have relatively large molecular weights among copepod luminescent enzymes, and are poor in terms of luminescence intensity diversity and stability, which are required in various bioassays. A bioluminescent enzyme is used as a luminescent label, and hence as its molecule becomes smaller, the risk of causing steric hindrance on a host molecule lowers. In general, a small-molecule protein can be expected to have a higher expression amount. Further, when the bioluminescent enzyme is allowed to have a variation in luminescence intensity and stability as compared to a conventional one, diverse needs in bioassays and bioluminescence imaging (BLI) can be met. In general, a luminescent enzyme having a high luminescence intensity has poor luminescence stability, and a luminescent enzyme having a low luminescence intensity has good luminescence stability. Accordingly, a combination of those two luminescent enzymes is advantageous for the observation of diverse molecular events in a time course. For example, a dual assay can be constructed. In a dual assay system, two luminescent enzymes coexist, and hence the assay always includes one step of suppressing a luminescent enzyme activity. Accordingly, a technique involving combining a luminescent enzyme having high stability and a luminescent enzyme having low stability is effective. Thus, an object of the present invention is to provide a luminescent enzyme having a small molecular weight as compared to an existing bioluminescent enzyme, or a luminescent enzyme having different luminescence intensities or stability.

Solution to Problem

It has been considered that novel artificial bioluminescent enzymes (ALucs) that overthrow conventional common knowledge can be newly established by utilizing a hitherto untried new technology for artificial protein creation. First, (1) As compared to around 2013, when ALucs were established for the first time, many luminescent plankton (copepoda)-derived natural luminescent enzymes have been further discovered, and an expanded database has been made. (2) A special amino acid sequence called an EF-hand, which binds to a cation, such as $Ca^{2+}$, seems to be present in an ALuc, and the sequence has been found to play an important role in luminescence activity. (3) Luminescent plankton (copepoda)-derived natural luminescent enzymes have different sequence lengths, and there is an example in which even the shortest sequence shows weak luminescence. Accordingly, it has been considered possible to create ALucs having sequences much shorter than those of conventional ALucs.

In the present invention, first, ALucs showing high luminescence intensities while conserving EF-hands in shorter sequences than conventional ones have been newly established by incorporating all the above-mentioned three elements. Those ALucs have been given the names of ALucs of 40's and 50's (ALuc41-51), and thus the present invention has been completed. In addition, on the basis of the backbones of existing ALucs, novel artificial bioluminescent enzymes (ALuc51-ALuc57) have been developed with reference to the amino acid sequences of ALuc40's.

That is, the present invention is as described below.

[1] A polypeptide, comprising any one of amino acid sequences (i) to (iii) below, and having a copepod luciferase activity:

(i) an amino acid sequence represented by SEQ ID NO: 1 or 12;

(ii) an amino acid sequence represented by SEQ ID NO: 1 or 12 in which one or several amino acids are substituted, added, or deleted; or (iii) an amino acid sequence having an identity of not less than 90% with an amino acid sequence represented by SEQ ID NO: 1 or 12.

[2] The polypeptide according to Item [1], wherein the amino acid sequence represented by SEQ ID NO: 1 or 12 is an amino acid sequence selected from the group consisting of amino acid sequences represented by SEQ ID NOs: 2 to 11 and 13 to 18.

[3] A nucleic acid, which encodes the polypeptide of Item [1] or [2].

[4] An expression vector, in which the nucleic acid of Item [3] is expressibly inserted.

[5] The expression vector according to Item [4], wherein the nucleic acid is linked to a nucleic acid encoding another protein so that the polypeptide encoded by the nucleic acid is expressed as a fusion protein with the another protein.

[6] A transformed cell, in which the nucleic acid of Item [3] is expressibly introduced.

[7] A reporter protein to be used for a reporter-gene assay method, the reporter protein comprising the polypeptide of Item [1] or [2].

[8] A luminescent fusion protein, comprising a fusion protein containing the reporter protein of Item [7], and a target protein or a peptide that recognizes a target protein.

[9] The luminescent fusion protein according to Item [8], wherein the luminescent fusion protein has a membrane localization signal (MLS) attached to a C-terminus of the reporter protein, and a target polypeptide inserted therebetween.

[10] The luminescent fusion protein according to Item [9], wherein the target polypeptide inserted is a fluorescent protein or a luciferase.

[11] The luminescent fusion protein according to Item [10], wherein the target polypeptide inserted is a polypeptide that changes a form in a plasma membrane, or a polypeptide having an amino acid sequence recognizable by the polypeptide that changes a form in a plasma membrane.

[12] An expression vector, comprising a reporter gene encoding the luminescent fusion protein of any one of Items [9] to [11].

[13] A transformed cell, in which the expression vector of Item [12] is introduced.

[14] A reporter-gene assay method for assaying an expression position, an expression timing, or an expression amount upon expression of a target gene in a cell in response to external stimulus, the method using the transformed cell of Item [13].

[15] The assay method according to Item [14], wherein the assay method is a reporter-gene assay method or a two-hybrid assay.

[16] A bioluminescent probe for measuring a ligand activity of a ligand-binding protein, the bioluminescent probe comprising a fusion protein containing the reporter protein of claim 7 bisected into an N-terminal side and a C-terminal side, a ligand-binding target protein, and a polypeptide that recognizes a change in steric structure upon binding of a ligand to the target protein.

[17] An expression vector for measuring a ligand activity of a ligand-binding protein, in which a nucleic acid encoding the bioluminescent probe of Item [16] is controlled by a control sequence that enables the nucleic acid to be expressed in a cell.

[18] A transformed cell, in which the expression vector of Item [17] is introduced.

[19] The transformed cell according to Item [18], wherein the transformed cell is a stem cell.

[20] A method of detecting a ligand activity of a ligand-binding protein in a test cell, the method using the expression vector of Item [16].

[21] A bioluminescence imaging method, comprising observing a ligand activity of a ligand-binding protein in a test cell using the expression vector of Item [16].

[22] A fusion protein for detecting a ligand,
the fusion protein comprising the polypeptide of Item [1] or [2], which is located between a protein A and a protein B, which have a binding site to which the ligand binds,
wherein the polypeptide makes a luciferase activity variable through use of a molecular strain that occurs when the protein A and the protein B have the ligand bound thereto.

[23] An expression vector, comprising a polynucleotide encoding the fusion protein of Item [22].

[24] A transformed cell, comprising the expression vector of Item [23].

[25] A method of detecting a ligand in a test sample, the method comprising a step of bringing the test sample into contact with the fusion protein of Claim 22.

In addition, the present invention also encompasses the following aspects.

[2-1]
A reaction buffer for an artificial bioluminescent enzyme, comprising components (1) and (2) below, the bioluminescence reaction buffer having an action of elevating a luminescence intensity of artificial bioluminescence:
(1) a basic buffer containing a Tris-buffer and/or an HBSS buffer; and
(2) a metal cation selected from the group consisting of Mg(II), Ca(II), and Cr(II).

[2-2]
A reaction buffer for an artificial bioluminescent enzyme, comprising components (1) and (2) below, the bioluminescence reaction buffer having an action of suppressing a luminescence intensity of artificial bioluminescence:
(1) a basic buffer containing a Tris-buffer and/or an HBSS buffer; and
(2) a metal cation selected from the group consisting of Mn(II), Co(II), Cu(II), Zn(II), Cd(II), Pb(II), Al(III), Fe(III), and Mo(IV).

[2-3]
A reaction buffer for an artificial bioluminescent enzyme, comprising components (1) and (2) below, the bioluminescence reaction buffer having an action of improving luminescence stability of artificial bioluminescence:
(1) a basic buffer containing a Tris-buffer and/or an HBSS buffer; and
(2) Co(II).

[2-4]
A reaction buffer for an artificial bioluminescent enzyme, comprising components (1) and (2) below, the bioluminescence reaction buffer having an action of improving an S/N ratio of artificial bioluminescence:
(1) a basic buffer containing a Tris-buffer and/or an HBSS buffer; and
(2) a metal cation selected from the group consisting of Co(II), Mn(II), and Cu(II).

[2-5]
A reaction buffer for an artificial bioluminescent enzyme, comprising components (1) and (2) below, the bioluminescence reaction buffer having an action of elevating a luminescence intensity of artificial bioluminescence:
(1) a basic buffer containing a Tris-buffer and/or an HBSS buffer; and
(2) vitamin C.

[2-6]
A reaction buffer for an artificial bioluminescent enzyme, the buffer having a pH of from 7 to 10.

Advantageous Effects of Invention

According to the present invention, the ALucs having high luminescence intensities as compared to natural luminescent enzymes have been newly established on the basis of a new molecular design technique.

BRIEF DESCRIPTION OF DRAWINGS

FIG. 2(A) is an illustration of multiple alignment of sequences and the supersecondary structure codes (SSC) of ALucs: ALuc16 (SEQ ID NO: 31); ALuc23 (SEQ ID NO: 32); ALuc25 (SEQ ID NO: 33); ALuc30 (SEQ ID NO: 34); and Aluc34 (SEQ ID NO: 35). The letters h, s, and b respectively mean the following: h) α-helix-type; s) (β-sheet-type; and b) disorder residue. Putative α-helices are marked with gray bars and numbered H1-H9. Pink shadows indicate consecutive homology regions. Key amino acids of the EF-hand-like regions (helix-loop-helix structure) are highlighted in yellow, and also with arrows, and compared to those of coelenterazine-binding protein (CBP). The arrow head in red shows the putative cleavage site of ALucs in the secretion process of ALucs. FIG. 2(B) is an image for showing relative optical intensities of ALuc mutants. The putative core sites of EF-hand-like regions of ALuc25 were mutated, and the consequent optical intensities were compared to native ALuc25 and other conventional bioluminescent enzymes. The corresponding mutation sites were as follows: ALuc25m1, E150Y and A182Y; ALuc25m2, E150W and A182W; ALuc25m3, E150Y; and ALuc25m4, E150W.

FIG. 4(A) is an image for showing the proton-dependent elevation of the optical intensities of native CTZ and ALucs imaged in pseudocolor (n=3; standard deviation). The image is one of triplicate results. FIG. 4(B) is an illustration of the chemical structure of native CTZ. FIG. 4(C) is a graph for showing the proton-dependent elevation of the optical intensities of ALucs (n=3; standard deviation). The maximal optical intensities were found in a higher pH region. FIG. 4(D) is a graph for showing relative optical stabilities of ALucs and marine bioluminescent enzymes at pH 9 (n=3; standard deviation). A percentage represents a sustained optical intensity as a ratio 20 minutes after nCTZ injection.

FIG. 6(A) is a graph for showing relative optical intensities of ALuc16 according to metal cations in 100 μg/mL (determined in triplicate). The optical intensities were normalized by the amount of ALuc16 (ng) and the integration time (sec). In inset a, a representative optical image by the indicated cations is shown. In inset b, the Mg(II)-concentration dependence of the optical intensities is shown (n=3; standard deviation). The asterisk highlights the elevated optical intensities. FIG. 6(B) is a graph for showing the cation-driven variance of the optical spectra. The intensity variance was monitored every 5 minutes for a duration of 60 minutes after substrate injection. The long-term stability was measured with 100 μg/mL of Ca(II). $I_{600}$ means an optical intensity ratio longer than 600 nm over the total intensity.

FIG. 8(A) is a graph for showing the time-course of the bioluminescence intensities with varying concentrations of Ca(II). The intensity variance was monitored every 10 minutes until 60 minutes after substrate injection. In the inset, the relative optical stability between 100 μg/mL of Ca(II) and Mg(II) is shown. In the optical image, the prolonged optical intensities with varying concentrations of Ca(II) are shown. The overall intensity range was adjusted by time to highlight the relative intensity variance. The scale of the relative luminescence unit (RLU) was shown in the indicators. FIG. 8(B) is a graph for showing the time-course of the absolute optical intensities with varying concentrations of Mg(II) (n=3; standard deviation). The initial optical intensities at 0 minutes are elevated in a concentration-dependent manner.

In FIG. 14(B), amino acids of ALuc23 are highlighted. Several bases at the 3'-terminus of ALuc23 are removed to reduce the background intensity and realize a complementary concept in the probe, which is an original purpose. The amino acid sequence highlights the eliminated C-terminus of ALuc23.

FIG. 15(A) is a graph for showing the absolute luminescence intensity of TPv2.4 for rapamycin (n=3). A number above the bar graph represents a factor between luminescence intensities at the times of the presence and absence of rapamycin ($10^{-6}$ M). In the upper and lower insets, a bioluminescence image and the chemical structure of native coelenterazine are shown and illustrated, respectively. A white bar represents an experiment under coexistence with native coelenterazine. FIG. 15(B) is the time course of bioluminescence after substrate addition (n=3). The bioluminescent enzyme is monitored every 5 minutes and expressed as a relative luminescence intensity in percent (%).

FIG. 18(A) is an illustration of alignment of amino acid sequences of newly developed artificial bioluminescent enzymes. The alignment was performed with CLUSTAL 2.1. ALuc50 (SEQ ID NO: 10); ALuc51 (SEQ ID NO: 11); ALuc45 (SEQ ID NO: 5); ALuc49 (SEQ ID NO: 9); ALuc44 (SEQ ID NO: 4); ALuc41 (SEQ ID NO: 2); ALuc47 (SEQ ID NO: 7); ALuc48 (SEQ ID NO: 8); ALuc43 (SEQ ID NO: 3); ALuc46 (SEQ ID NO: 6); ALuc42 (SEQ ID NO: 13); ALuc52 (SEQ ID NO: 14); ALuc53 (SEQ ID NO: 15); ALuc55 (SEQ ID NO: 16); ALuc56 (SEQ ID NO: 17); ALuc57 (SEQ ID NO: 18); ALuc30 (SEQ ID NO: 34).

FIG. 22(A) is a graph for showing the absolute values of the luminescence intensities of the molecular strain sensor with or without a metal ion. A luminescence intensity integrated for 1 second per 1 μg of the molecular strain sensor is shown, and hence the unit is RLU/sec/μg. FIG. 22(B) is a graph for showing relative values of the luminescence intensities of the molecular strain sensor with or without a metal ion. That is, relative luminescence intensities at the time of the presence of a metal ion as compared to luminescence intensities (1) at the time of the absence of the metal ion are shown.

FIG. 23(A) is a graph for showing the time courses of the luminescence intensity according to changes in $Ca^{2+}$ concentration (within 1 minute after substrate addition). An increase in $Ca^{2+}$ concentration reduces an overall luminescence intensity, but improves an S/N ratio. FIG. 23(B) is a graph for showing the time courses of the luminescence intensity according to changes in $Co^{2+}$ concentration (within 1 minute after substrate addition).

DESCRIPTION OF EMBODIMENTS

Figure 1:
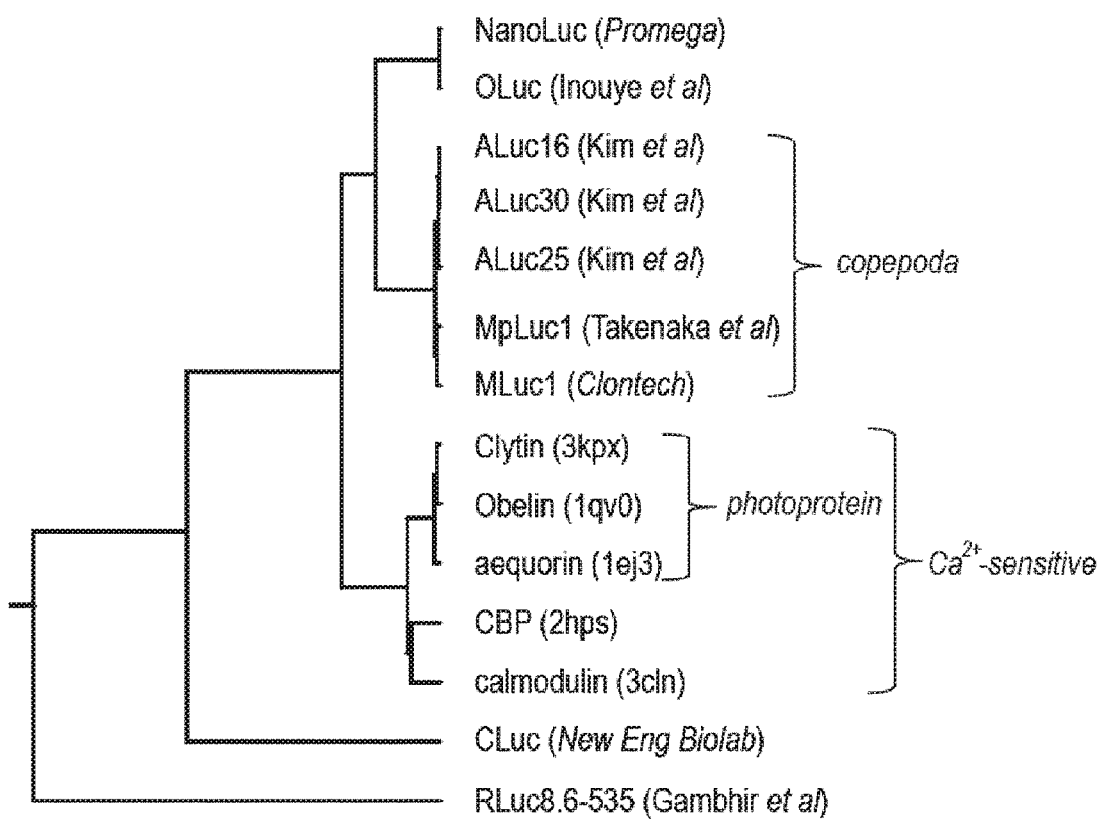
FIG. 1 is a phylogram of marine bioluminescent enzymes, photoproteins, and other $Ca^{2+}$-binding proteins. A PDB accession number, a developer, or a provider is shown in parentheses. Abbreviations: NonoLuc represents a mutant of *Oplophorus* bioluminescent enzyme (OLuc), ALucs represent artificial bioluminescent enzymes, MpLuc1 represents *Metridia pacifica* bioluminescent enzyme 1, MLuc represents *Metridia longa* bioluminescent enzyme, CBP represents a coelenterazine-binding protein from *Renilla muelleri*, CLuc represents *Cypridina* bioluminescent enzyme, and RLuc8.6-535 represents *Renilla* bioluminescent enzyme 8.6-535.

1. Artificial Luciferases (ALucs) of the Present Invention
(1-1) Copepod Luciferase:

Regarding luminescent marine animals, it is known that marine animals derived from *Metridia okhotensis, Pleuromamma abdominalis, Lucicutia ovaliformis, Heterorhabdus tanneri, Heterostylites major, Gaussia princeps, Renilla reniformis, Metridia pacifica, Lucicutia grandis, Lucicutia bicornuta, Pleuromamma xiphias, Pleuromamma scutullata, Haloptilus pseudooxycephalus, Candacia longimana, Candacia columbiae, Candacia bipinnata, Calanus jashnovi, Neocalanus cristatus, Neocalanus flemingeri, Neocalanus plumchrus, Scaphocalanus magnus, Spinocalanus spinipes, Euchaeta marina, Undeuchaeta plumose, Undeuchaeta major, Xanthocalanus kurilensis, Scaphocalanus magnus Gaidius variabilis, Euchirella amoena, Cypridina (Cypridina noctiluca;* CLuc), obelin, aqualine, or *Oplophorus* produce bioluminescent enzymes (luciferases).

In the present invention, the "copepod luciferase" indicates a luminescent enzyme (luciferase) produced by small crustaceans called copepods that live as luminescent plankton among the "luminescent marine animals." Specific examples of the "copepod luciferase" include MoLuc1, MoLuc2, PaLuc1, PaLuc2, LoLuc, HtLuc1, HtLuc2, HmLuc1, HmLuc2, *Gaussia* luciferase (GLuc), *Renilla* luciferase (RLuc), *Metridia* luciferase (MLuc, MpLuc1, MpLuc2), and *Cypridina noctiluca* luciferase (CLuc). Regarding the substrate specificity, the "copepod luciferase" specifically oxidizes "coelenterazine." The "copepod luciferase" generally has an enzymatic property of catalyzing luminescent reaction under a deep-sea environment, i.e., an optimum pH of from about 7.5 to about 8 and an optimum temperature of from about 4° C. to about 10° C., but also catalyzes luminescence under various conditions other than the above. The "copepod luciferases" hereinafter refer to luciferases sharing common enzyme activity and structural characteristics with luciferases originating from known copepods. Specifically, the "copepod luciferases" mean luciferases having an optimum pH of from about 5 to about 8 and an optimum temperature of from about 4° C. to about 25° C., and an enzymatic activity that catalyzes luminescent reaction using "coelenterazine" as a substrate. The luciferases have two enzymatic activity domains and a secretion signal at their N-terminus, and a molecular weight of about 20 kD (from 18 kD to 28 kD), which is the smallest in the luminescent enzymes. The amino acid sequence homology of the "copepod luciferases" is about not less than 50%, and the amino acid sequence structures, such as hydrophilic and hydrophobic patterns, and the position of the enzymatic activity region, are similar. The "copepod luciferases" are luciferases having higher luminescence intensities than other marine organism-derived luciferases.

Herein, the "coelenterazine" is not limited to native coelenterazine (native CTZ), but includes various derivatives of native coelenterazine. That is, the "coelenterazine" may also be referred to as "coelenterazine-type." Specific examples of the coelenterazine include native coelenterazine (Native CTZ), coelenterazine ip (CTZ ip), coelenterazine i (CTZ i), coelenterazine hcp (CTZ hcp), coelenterazine 400A (CTZ 400A), coelenterazine fcp (CTZ fcp), coelenterazine cp (CTZ cp), coelenterazine f (CTZ f), coelenterazine h (CTZ h), and coelenterazine n (CTZ n).

(1-2) Artificial Luciferases (ALucs) of the Present Invention

The novel artificial luciferases (ALucs) of the present invention have been created based on the amino acid sequences of the "copepod luciferases," and hence have the basic enzyme properties of the "copepod luciferases," such as the substrate specificity and suitable pH described above. The artificial luciferases of the present invention are also novel artificial luciferases having significantly excellent luminescence characteristics such as luminescence intensity, luminescence in a long wavelength, and luminescence stability.

A typical artificial luciferase (ALuc) in the present invention is a polypeptide containing an amino acid sequence represented by SEQ ID NO: 1 or SEQ ID NO: 12. Examples of the polypeptide containing an amino acid sequence represented by SEQ ID NO: 1 include ALuc41 (SEQ ID NO: 2), ALuc43 (SEQ ID NO: 3), ALuc44 (SEQ ID NO: 4), ALuc45 (SEQ ID NO: 5), ALuc46 (SEQ ID NO: 6), ALuc47 (SEQ ID NO: 7), ALuc48 (SEQ ID NO: 8), ALuc49 (SEQ ID NO: 9), ALuc50 (SEQ ID NO: 10), and ALuc51 (SEQ ID NO: 11). In addition, examples of the polypeptide having an amino acid sequence represented by SEQ ID NO: 2 include ALuc42 (SEQ ID NO: 13), ALuc52 (SEQ ID NO: 14), ALuc53 (SEQ ID NO: 15), ALuc55 (SEQ ID NO: 16), ALuc56 (SEQ ID NO: 17), and ALuc57 (SEQ ID NO: 18).

That is, the artificial luciferase (ALuc) according to one embodiment of the present invention may also be expressed as a polypeptide containing any one of amino acid sequences (i) to (iii) below, and having a copepod luciferase activity:

(i) an amino acid sequence represented by any one of SEQ ID NOs: 2 to 11 and 13 to 18;

(ii) an amino acid sequence represented by any one of SEQ ID NOs: 2 to 11 and 13 to 18 in which one or several amino acids are deleted, substituted, inserted, or added (herein, the "several" in the "one or several amino acids" means from 1 to 20, preferably from 1 to 10, more preferably from 1 to 5); and (iii) an amino acid sequence having an identity of not less than 90% with an amino acid sequence represented by any one of SEQ ID NOs: 2 to 11 and 13 to 18.

For example, an amino acid sequence having an identity of not less than 95%, not less than 96%, not less than 97%, not less than 98%, not less than 99%, and not less than 99.5% is more preferred.

The amino acid sequences of the artificial luciferases (ALucs) of the present invention have common basic frame structures shown in FIG. 1. As long as the artificial luciferase has such a basic frame structure, an equivalent high performance copepod luciferase activity can be obtained even when amino acids at other positions are freely selected amino acids. Accordingly, the artificial luciferase (ALuc) of the present invention can be expressed as a polypeptide containing any one of amino acid sequences (iv) to (vi) below, and having a copepod luciferase activity:

(iv) an amino acid sequence represented by SEQ ID NO: 1 or SEQ ID NO: 12;

(v) an amino acid sequence represented by SEQ ID NO: 1 in which one or several amino acids are deleted in at least one of a region corresponding to positions 1-29 and a region corresponding to positions 195-199; or (vi) an amino acid sequence represented by SEQ ID NO: 12 in which one or several amino acids are deleted in at least one of a region corresponding to positions 1-29 and a region corresponding to positions 214-218.

In the amino acid sequence represented by SEQ ID NO: 1, amino acids from positions 1-20 of the N-terminal side are secretion signals (secretion peptide; SP), and a peptide at positions 192-196 of the C-terminal side is a Glycine rich linker-like peptide (commonly known as a GS linker). Accordingly, part or all of the amino acids in these regions may be deleted. Similarly, in the amino acid sequence represented by SEQ ID NO: 12, amino acids from positions 1-20 of the N-terminal side are secretion signals (secretion peptide; SP), and a peptide at positions 211-215 of the C-terminal side is a Glycine rich linker-like peptide (commonly known as a GS linker). Accordingly, part or all of the amino acids in these regions may be deleted. In copepod luciferases, such as *Metridia pacifica* luciferase 1 (MpLuc1) and *Pleuromamma* luciferase, the secretion signals correspond to amino acids at positions 1-18 in *Metridia pacifica* luciferase 1 (MpLuc1), and correspond to amino acids at positions 1-19 in *Pleuromamma* luciferase. It is known that these amino acids may be deleted.

The function of an artificial luciferase is not significantly impaired even when amino acids at positions 20-29 in the amino acid sequence represented by SEQ ID No: 1 or SEQ ID NO: 12 are substituted with a functional amino acid sequence (e.g., antigen recognition site, affinity chromatography recognition site, or official signal). Accordingly, part or all of the amino acids in this region may be deleted.

In the amino acid sequence represented by SEQ ID NO: 1 or SEQ ID NO: 12, amino acids represented by small letters are described in detail below.

In addition, in this case, the properties of individual amino acids were determined to be, for example, hydrophilic, hydrophobic, or neutral on the basis of Table 1 below.

TABLE 1

| Amino acid | Property | | |
|---|---|---|---|
| Alanine | Hydrophobic | Aliphatic | Neutral |
| Arginine | Hydrophilic | | Basic |
| Asparagine | Hydrophilic | | Neutral |
| Aspartic acid | Hydrophilic | | Acidic |
| Cysteine | Hydrophobic | Sulfur-containing | Neutral |
| Glutamic acid | Hydrophilic | | Acidic |
| Glutamine | Hydrophilic | | Neutral |
| Glycine | Hydrophobic | Aliphatic | Neutral |
| Histidine | Hydrophilic | | Basic |
| Isoleucine | Hydrophobic | Aliphatic | Neutral |
| Leucine | Hydrophobic | Aliphatic | Neutral |
| Lysine | Hydrophilic | | Basic |
| Methionine | Hydrophobic | Sulfur-containing | Neutral |
| Phenylalanine | Hydrophobic | Aromatic | Neutral |
| Proline | Hydrophobic | Imide | Neutral |
| Serine | Hydrophilic | Hydroxy | Neutral |
| Threonine | Hydrophilic | Hydroxy | Neutral |
| Tryptophan | Hydrophobic | Aromatic | Neutral |
| Tyrosine | Hydrophobic | Aromatic | Neutral |
| Valine | Hydrophobic | Aliphatic | Neutral |

Of the amino acids shown in SEQ ID NO: 1, amino acids at positions 20, 31, 33, 40, 45, 46, 63, 67, 89, 90, 104, 132, 167, 183, and 186 may be any amino acids, and may also be deleted. It is preferred that the amino acid at position 20 be P or H, the amino acid at position 31 be D or G, the amino acid at position 33 be V or E, the amino acid at position 40 be G or D, the amino acid at position 45 be R or L, the amino acid at position 46 be D or deleted, the amino acid at position 63 be K or L, the amino acid at position 67 be I or K, the amino acid at position 89 be I or D, the amino acid at position 90 be K or W, the amino acid at position 104 be H or E, the amino acid at position 132 be D or E, the amino acid at position 167 be K or L, the amino acid at position 183 be K or A, and the amino acid at position 186 be D, A, or G.

In addition, amino acids at positions 11, 13, 37, 41, 51, 69, 95, 120, 121, 124, 125, 154, 157, 160, 164, and 191 are hydrophobic amino acids (e.g., V, F, A, and L), and it is preferred that the amino acid at position 11 be V or I, the amino acid at position 13 be L or F, the amino acid at position 41 be V or L, the amino acid at position 51 be A or G, the amino acid at position 70 be I or L, the amino acid at position 95 be M or V, the amino acid at position 96 be Y or W, the amino acid at position 120 be P or A, the amino acid at position 121 be I or V, the amino acid at position 124 be A or I, the amino acid at position 125 be P or L, the amino acid at position 154 be L or W, the amino acid at position 157 be L or W, the amino acid at position 160 be V or L, the amino acid at position 164 be A or L, and the amino acid at position 191 be L or A.

Amino acids at positions 19, 21-27, 35, 42, 43, 52, 74, 88, 110, 111, 172, and 184 are hydrophilic amino acids (e.g., Q, K, D, R, H, E, and T), and it is preferred that the amino acid at position 19 be K or N, the amino acids at positions 21-27 be HHHHHHH (SEQ ID NO: 41) or TEDEDED (SEQ ID NO: 42), the amino acid at position 35 be N or K, the amino acid at position 42 be V or L, the amino acid at position 43 be N or T, the amino acid at position 52 be D or R, the amino acid at position 74 be K or Q, the amino acid at position 88 be K or H, the amino acid at position 110 be K or E, the amino acid at position 111 be D or E, the amino acid at position 172 be D or S, and the amino acid at position 184 be E or Q.

Amino acids at positions 38, 39, 50, 134, 176, 185, 187, and 192 are neutral amino acids, and it is preferred that the amino acid at position 38 be A or T, the amino acid at position 39 be I or T, the amino acid at position 50 be S or V, the amino acid at position 134 be T or A, the amino acid at position 176 be S or G, the amino acid at position 185 be V or Q, the amino acid at position 187 be T, N, Y, F, or W, and the amino acid at position 192 be A or G.

Of the amino acids shown in SEQ ID NO: 12, amino acids at positions 20, 31, 33, 40, 45, 46, 51-69, 82, 86, 108, 109, 123, 151, 186, 202, and 205 may be any amino acids, and may also be deleted. It is preferred that the amino acid at position 20 be P or H, the amino acid at position 31 be D or G, the amino acid at position 33 be V or E, the amino acid at position 40 be G or D, the amino acid at position 45 be R or L, the amino acid at position 46 be D or deleted, the amino acids at positions 51-69 be EDMNVISRDTDVDAN-RADR (SEQ ID NO: 43) or deleted, the amino acid at position 82 be K or L, the amino acid at position 86 be I or K, the amino acid at position 108 be I or D, the amino acid at position 109 be K or W, the amino acid at position 123 be H or E, the amino acid at position 151 be D or E, the amino acid at position 186 be K or L, the amino acid at position 202 be K or A, and the amino acid at position 205 be D, A, or G.

In addition, amino acids at positions 11, 13, 37, 41, 70, 88, 114, 125, 139, 140, 143, 144, 173, 176, 179, 183, and 210 are hydrophobic amino acids (e.g., V, F, A, and L), and it is preferred that the amino acid at position 11 be V or I, the amino acid at position 13 be L or F, the amino acid at position 41 be V or L, the amino acid at position 70 be A or G, the amino acid at position 89 be I or L, the amino acid at position 114 be M or V, the amino acid at position 125 be Y or W, the amino acid at position 139 be P or A, the amino acid at position 140 be I or V, the amino acid at position 143 be A or I, the amino acid at position 144 be P or L, the amino acid at position 173 be L or W, the amino acid at position 176 be L or W, the amino acid at position 179 be V or L, the amino acid at position 183 be A or L, and the amino acid at position 210 be L or A.

Amino acids at positions 19, 21-27, 35, 42, 43, 71, 93, 107, 129, 130, 191, and 203 are hydrophilic amino acids (e.g., Q, K, D, R, H, E, and T), and it is preferred that the amino acid at position 19 be K or N, the amino acids at positions 21-27 be HHHHHHH (SEQ ID NO: 41) or TED-EDED (SEQ ID NO: 42), the amino acid at position 35 be N or K, the amino acid at position 42 be V or L, the amino acid at position 43 be N or T, the amino acid at position 71 be D or R, the amino acid at position 93 be K or Q, the amino acid at position 107 be K or H, the amino acid at position 129 be K or E, the amino acid at position 130 be D or E, the amino acid at position 191 be D or S, and the amino acid at position 203 be E or Q.

Amino acids at positions 38, 39, 50, 153, 195, 204, 206, and 211 are neutral amino acids, and it is preferred that the amino acid at position 38 be A or T, the amino acid at position 39 be I or T, the amino acid at position 50 be S or V, the amino acid at position 153 be T or A, the amino acid at position 195 be S or G, the amino acid at position 204 be V or Q, the amino acid at position 206 be T, N, Y, F, or W, and the amino acid at position 211 be A or G.

The artificial luciferase according to another embodiment of the present invention includes an antibody recognition site (epitope sequence) therein. The "antibody recognition site" or the "epitope sequence" may also be referred to as "antigen site."

Specifically, in the artificial luciferase having an antibody recognition site (epitope sequence) therein, a region corresponding to positions 20-31 in SEQ ID NO: 1 or SEQ ID NO: 12 includes an antibody recognition site (epitope sequence). Preferred examples of the antibody recognition site (epitope sequence) include, but not limited to, a His-tag (HHHHHH) (SEQ ID NO: 19), a FLAG-tag (DYKDDDDK) (SEQ ID NO: 20), a Myc-tag (EQKLISEEDL) (SEQ ID NO: 21), an HA-tag (YPYDVPDYA) (SEQ ID NO: 22), a V5-tag (GKPIPNPLLGLDST) (SEQ ID NO: 23), and a T7-tag (MASMTGGQQMG) (SEQ ID NO: 24).

In an example of the artificial luciferase having a His-tag therein, amino acids at positions 20-31 in SEQ ID NO: 1 or SEQ ID NO: 12 are all H (His×8 sequence).

In an example of the artificial luciferase having a FLAG-tag therein, amino acids at positions 20-31 in SEQ ID NO: 1 or SEQ ID NO: 12 are DYKDDDDK (FLAG-tag sequence, SEQ ID NO: 20).

In an example of the artificial luciferase having a c-Myc-tag therein, the sequence of the region corresponding to positions 20-31 in SEQ ID NO: 1 or SEQ ID NO: 12 is EQKLISEEDL (Myc-tag sequence, SEQ ID NO: 21).

In an example of the artificial luciferase having an HA-tag therein, amino acids at positions 20-31 in SEQ ID NO: 1 or SEQ ID NO: 12 are YPYDVPDYA (HA-tag sequence, SEQ ID NO: 22).

In one embodiment, the amino acid sequence of SEQ ID NO: 1 and the amino acid sequence of SEQ ID NO: 12 may be represented as follows.

```
SEQ ID NO: 1:
MMGIKVLFALyCyALVQAzxzzzzzzzzDIVxVxGzEynnxyzzDxxFTIn yzRGKLPGKKLPxEVLxEyEANAzKAGCTRGCLICLSzxxCTAKyKKWLP GRCxSyEGDzzTGQGGIGEyyVDyyEIPGFKxLnPMEQFIAQVDLCADCT TGCyKGyANyKCSyLLxKWLPzRCAnFADHIQxznxnIKGynGS
```

(In the amino acid sequence, x represents any amino acid, y represents a hydrophobic amino acid, z represents a hydrophilic amino acid, and n represents a neutral amino acid.)

```
SEQ ID NO: 12:
MMGIKVLFALyCyALVQAzxzzzzzzzzDIVxVxGzFynnxyzzDxxFTIn xxxxxxxxxxxxxxxxxxxxyzRGKLPGKKLPxEVLxEyEANAzKAGCTRG CLICLSzxxCTAKyKKWLPGRCxSyEGDzzTGQGGIGEyyVDyyEIPGFK xLnPMEQFIAWDLCADCTTGCyKGyANyKCSyLLxKWLPzPCAnFADKIQ xznxnIKGynGS
```

(In the amino acid sequence, x represents any amino acid, y represents a hydrophobic amino acid, z represents a hydrophilic amino acid, and n represents a neutral amino acid.)

2. Strategy for Establishing Artificial Luciferase of the Present Invention

It is an object of the present invention to establish an artificial bioluminescent enzyme that (1) has a low genetic correlation with already developed artificial bioluminescent enzymes (ALucs), (2) has a smaller molecular weight, and (3) shows luminescence intensities with a higher variation or luminescence stability.

However, this object is an object that is difficult to meet by any known method, such as a point mutagenesis method (site-directed mutagenesis). The above-mentioned object is not achieved even with the conventional ALuc series recently developed by the inventor of the present invention. The above-mentioned object cannot be achieved because the conventional ALuc series adopt a strategy involving extracting frequently occurring amino acids from aligned sequences, and hence their combination inevitably results in the longest amino acid sequence.

Therefore, in the present invention, in order to achieve the object, a research for establishing "small and strong luminescent enzymes" has been conducted by returning to the starting point of ALuc establishment and restarting design from the beginning.

As described above, since a patent application on the conventional ALucs (JP 2014-100137 A), a database has been further accumulated, and today, the database contains as many as 27 kinds of natural copepod luminescent enzymes (25 kinds from National Institute of Advanced Industrial Science and Technology (AIST), and 2 kinds from another institution). Novel ALuc sequences have been established by a strategy involving boldly deleting infrequently occurring amino acids while extracting frequently occurring amino acids from sequence information on the new data pool. For this purpose, dedicated software, such as WebLogo, is preferably used (see FIG. 17). Frequently occurring amino acids have been connected together to create new sequences completely different from any of the conventional luminescent enzyme sequences.

Further, in order to reduce a molecular weight, the following procedure, which has been found for the first time by the inventor of the present invention, has been performed.

Figure 17:
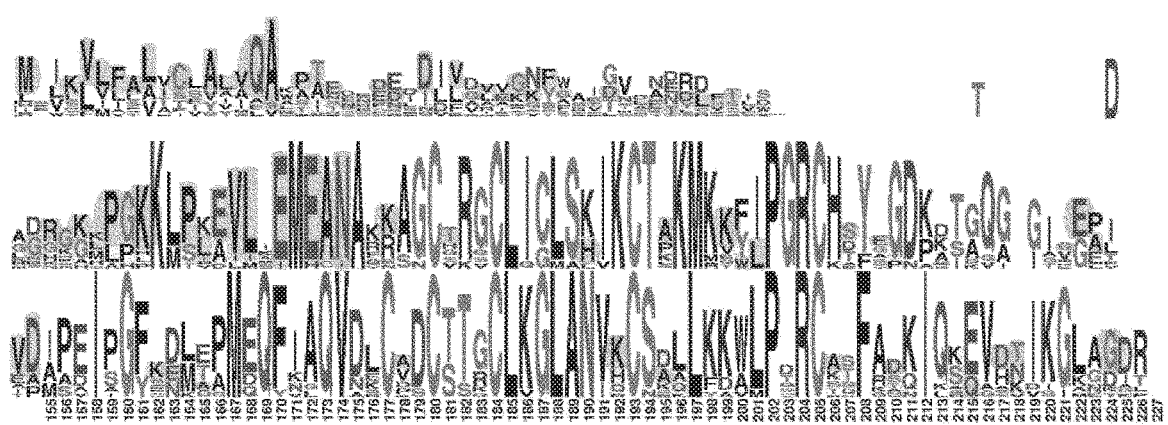
FIG. 17 is an illustration of results of extraction of frequently occurring amino acids from natural luminescent plankton-derived luminescent enzymes using known software (WebLogo display). The size of a letter means the degree of frequency.

First, when a set of frequently occurring amino acids is extracted using dedicated software, such as WebLogo, infrequently occurring amino acids appear as blanks in the extracted sequence (see FIG. 17). Thus, the inventor of the present invention has concluded that regions that do not show sizable frequencies are sites that do not particularly affect an enzymatic activity, and has eliminated the regions. At the same time, the inventor of the present invention has connected together only frequently occurring parts, to thereby newly establish a series of ALucs having sequences much shorter than those of the conventional ALucs. When the sequences were further folded, repetition was found between upper and lower sequences, and an adjustment was made to increase the homology between the upper and lower sequences.

Further, typical EF-hand-like structures are present at four sites in each of the sequences (FIG. 3), and introduction of a mutation into any of these EF-hand-like structures inactivates the enzyme. Thus, it has been revealed for the first time that the EF-hand-like structures are sites deeply involved in luminescence characteristics of ALucs. Therefore, as ALucs of the numbers 40's and 50's, which have been newly established in the present invention, a series of ALucs have been able to be created with consideration for the conservation of the EF-hand-like structures. Thus, novel artificial luciferases provided by the present invention have been achieved by the novel approach as described above.

Now, "3. Enzymatic Activity of Artificial Luciferase (ALuc) of the Present Invention," "4. Functional Improvement of Artificial Luciferase (ALuc) of the Present Invention," "5. Application of Luciferase (ALuc) of the Present Invention to "reporter-gene assay method "," "6. Buffer for Bioassay," "7. Bioassay of Interest for Artificial Luciferase of the Present Invention," "8. Measuring Procedure and Measuring Apparatus Used in Test Using Artificial Luciferase of the Present Invention," and "9. Analyte of Interest in Bioassay" are described referring to or citing the contents disclosed in JP 2014-100137 A and WO 2014/065047 A1. The above-mentioned literatures are incorporated herein by reference.

3. Enzymatic Activity of Artificial Luciferase (ALuc) of the Present Invention (3-1) Enzymatic Activity Confirmation Method The enzymatic activity of ALuc may be examined according to the following method. First, using a known lipid reagent for gene introduction, an expression vector encoding ALuc is introduced into African monkey-derived COS-7 cells. As a control, an expression vector having a known GLuc without any mutation is also introduced into the cells in the same manner. At a predetermined time (from 10 hours to 20 hours, for example, 16 hours) after the introduction of the vector, a cell lysate is prepared using a known cell lysis reagent.

After that, the cell lysate is mixed with a known substrate solution containing coelenterazine, and its color intensity, temporal stability in luminescence, and the like are measured.

The luminescence intensity may be found by measuring the intensity at a specific wavelength using a conventional luminescence spectrophotometer after addition of a known substrate. By performing the measurement every minute, the temporal stability in luminescence can be evaluated based on the temporal change in luminescence. In order to measure a shift to a longer wavelength, scanning of the entire wavelength is required.

(3-2) Characteristics of Enzymatic Activity of Artificial Luciferase (ALuc) of the Present Invention Typical examples of the artificial luciferase (ALuc) of the present invention include ALuc41 (SEQ ID NO: 2), ALuc43 (SEQ ID NO: 3), ALuc44 (SEQ ID NO: 4), ALuc45 (SEQ ID NO: 5), ALuc46 (SEQ ID NO: 6), ALuc47 (SEQ ID NO: 7), ALuc48 (SEQ ID NO: 8), ALuc49 (SEQ ID NO: 9), ALuc50 (SEQ ID NO: 10), and ALuc51 (SEQ ID NO: 11).

Characteristics of enzymatic activity commonly observed in conventional copepod luciferases may be, for example, as follows.

(1) Exhibiting transient high-intensity light and poor luminescence stability,
(2) Having a secretion signal at the N-terminal side,
(3) The size of the luminescent enzyme being smaller than that of other luminescent enzymes, and
(4) Commonly exhibiting blue light (480 nm).

The ALuc series of the present invention maintain the characteristics (2) and (3). In addition, the ALuc series have much higher luminescence stability (Item (1) above) than conventional copepod luciferases. In particular, ALuc45 exhibits a remarkably stable luminescence signal even as compared to an existing ALuc.

Luminescence intensity and stability are picked up as two major properties of a bioluminescent enzyme. As described above, some novel ALucs are improved in both luminescence intensity and luminescence stability as compared to conventional ones, overthrowing the common knowledge that, in general, an improvement in luminescence intensity leads to poor stability and an improvement in stability leads to a poor luminescence intensity.

In view of the above, the present invention is confirmed to produce artificial luciferases of great promise that maintain the advantageous features of conventional copepod luciferases while overcoming common problems of conventional copepod luciferases.

Further, in one embodiment, the ALuc provided by the present invention has a smaller molecular weight even as compared to an existing ALuc. A bioluminescent enzyme is used as a luminescent label, and hence being a small molecule provides the following advantages. That is, as the molecule becomes smaller, the risk of causing steric hindrance on a host molecule lowers. In addition, a small-molecule protein can be expected to have a higher expression amount. Further, it is considered that the risk of protein misfolding lowers, and after folding, a luminescence function is quickly exhibited. As just described, a smaller-molecule ALuc is excellent in, for example, the above-mentioned points.

4. Functional Improvement of Artificial Luciferase (ALuc) of the Present Invention The usages of the artificial luciferase (ALuc) of the present invention typically include those as a luminescent enzyme component of a conventional bioluminescent probe, and, owing to its high luminance and stable luminescence signal, as substitutes for reporter genes for fluorescent imaging in vivo. The present invention is mainly used in mammals, such as humans, in vivo, or in mammalian cells in vitro.

Accordingly, the advantageous modifications for improving other functions include modification of the codons corresponding to the amino acid into codons suitable for host organisms for easy expression, and an improvement of expression promoters for indirect functional improvement. Further, by linking a functional peptide to an N- or C-terminus of the artificial bioluminescent enzyme (ALuc) of the present invention, various additional functions can be expected. For example, by linking a membrane localization signal (MLS) to the N- or C-terminus, the ALuc can be localized in the plasma membrane. In this case, the secretion signal at the N-terminal side (positions 1-20, or part of the sequence) derived from ALuc may be present or absent. However, the secretion signal is transferred across endoplasmic reticulum, and hence the folding efficiency of an ALuc-containing fusion protein can be increased in some cases. In the present invention, when two or more types of peptides, including a signal peptide, are linked, the length, reading frame, and the like are adjusted using a known suitable linker, even when the linker is not specified. Localization of ALuc in the plasma membrane allows smooth external supply of the substrate or oxygen. Thus, a luminescent probe (e.g., luminescent capsule) containing ALuc as a base can quickly respond to the external signal. The present invention adopts the above as required. The modification strategies for improving functions are specifically described below. However, the present invention is not limited to these methods.

5. Application of Luciferase (ALuc) of the Present Invention to "Reporter-gene Assay method"

(5-1) "Reporter-Gene Assay Method" of the Present Invention

The ALuc of the present invention and the gene thereof can be preferably used as a "reporter protein" or a "reporter gene" in "reporter-gene assay methods."

The "reporter protein" or "reporter gene" in the present invention indicates a luminescent label used for examining the behavior of a target protein or a target gene in cells in response to external stimulus. In addition, the "reporter-gene assay method" in the present invention is an assay method in which the behavior of a target protein or a target gene in cells in response to external stimulus is observed in view of the luminescence by ALuc, luminescence amount, luminescence timing, or luminescence site, by using the ALuc of the present invention or its gene as a "reporter protein" or a "reporter gene." Specifically, the reporter-gene assay method may be said to be a method of qualitatively or quantitatively measuring the expression site, expression timing, or expression amount of the target gene as the luminescence site, luminescence timing, or luminescence amount of the reporter protein ALuc.

More specifically, the reporter protein is typically used as a fusion protein by being fused with the N- or C-terminus of the target protein. However, reporter proteins bisected into the N-terminal side and the C-terminal side may be fused with the target protein in a direct manner or via another peptide sequence. The reporter gene is typically used for examining the behavior of the target protein after expression, by being linked to the 5'- or 3'-terminus of the target gene to form a chimera gene. Similarly, the reporter gene may be bisected, with one part linked to the 5'-terminus of the target gene, and the other linked to the 3'-terminus of the target gene, or both may be inserted into the target gene for use.

The reporter protein of the present invention may be described as follows using the definition of ALuc above.

The reporter protein, comprising a polypeptide containing any one of amino acid sequences (i) to (vii) below, and having a copepod luciferase activity:
(i) an amino acid sequence represented by any one of SEQ ID NOs: 2 to 11 and 13 to 18;
(ii) an amino acid sequence represented by any one of SEQ ID NOs: 2 to 11 and 13 to 18 in which one or several amino acids are deleted, substituted, inserted, or added (herein, the "several" means from 1 to 20, preferably from 1 to 10, more preferably from 1 to 5);
(iii) an amino acid sequence having an identity of not less than 90% with an amino acid sequence represented by any one of SEQ ID NOs: 2 to 11 and 13 to 18;
(iv) an amino acid sequence represented by SEQ ID NO: 1;
(v) an amino acid sequence represented by SEQ ID NO: 1 in which one or more amino acids are deleted in at least one of a region corresponding to positions 1-29 and a region corresponding to positions 195-199;
(vi) an amino acid sequence represented by SEQ ID NO: 12; and
(vii) an amino acid sequence represented by SEQ ID NO: 12 in which one or more amino acids are deleted in at least one of a region corresponding to positions 1-29 and a region corresponding to positions 214-218.

When the reporter protein of the present invention is used in in vivo conditions, e.g., in a living body, the "reporter gene" comprising a nucleic acid encoding any one of the amino acid sequences (i) to (vii) is linked with a target gene, and incorporated into a vector or the like to be introduced into target cells.

The "reporter-gene assay method" of the present invention is hereinafter categorized into three groups: "basic", "inducible", and "activatable", which are disclosed in Niu, G., Chen, X. Y. Theranostics, 2 2012 413. of Niu et al., and application of the ALuc of the present invention to each assay method is specifically described. Herein, the "basic" method may be said to be the simplest reporter-gene assay method system in which ALuc is simply linked with each subject protein for labeling. Typical examples include a bioluminescent enzyme fusion protein that is linked with an antibody (i.e., bioluminescent enzyme label antibody). The "inducible" method differs from the "basic method" in that the expression of the reporter is controlled by a promoter. Typical examples include so-called reporter-gene assay methods and two hybrid assays (reporter is expressed depending on stimulus) in addition to a bioluminescence resonance energy transfer (BRET) method. In addition, the "activatable" method is a reporter-gene assay method utilizing the mechanism in which the reporter itself actively reacts in response to ligand stimulation to illuminate. Typical examples include an integrated-molecule-format bioluminescent probe and a luminescent capsule. This method can also be applied to a protein-fragment complementation assay (PCA), protein splicing assay (PSA), and the like.

(5-2) Basic Method

When the ALuc of the present invention is applied to a "basic method" as a reporter protein, a fusion protein in which the ALuc is simply linked with a target protein may be produced. The basic method differs from the other reporter-gene assay methods sin that expression during the production of the fusion protein is performed by using an uncontrolled-type promoter.

Herein, the "fusion protein" includes (i) a fusion protein integrally expressed from a gene encoding a fusion protein containing a reporter protein, which is ALuc, and a target protein or a peptide recognizing the target protein, and (ii) a fusion protein obtained by separately expressing a reporter protein, which is ALuc, and a target protein or a peptide recognizing the target protein, and linking them by a chemical reaction. Examples of the means for linking separately expressed proteins and the like by a chemical reaction include linking using a cross linker, linking using an avidin-biotin binding ability, and binding using chemical reactivity of amino acid residues.

A bioluminescent fusion protein that binds to a typical antibody is hereby described. The bioluminescent fusion protein may be completed by producing a chimera DNA in which an ALuc gene is linked with the upstream or downstream of cDNA of antibody single chain variable fragment (scFv), and introducing the DNA into a suitable expression vector.

(5-3) "Inducible" Method

Application of a bioluminescent enzyme to an "inducible method" as a reporter protein has been employed for analyzing the expression timing and expression amount of genes in the production of a recombinant protein using a recombinant DNA technology. In particular, the bioluminescent enzyme has been widely used as an indicator of the expression timing and expression amount change in response to external stimulus. Examples of assay systems included in the "inducible methods" include reporter-gene assay methods, yeast two-hybrid assays, mammalian two-hybrid assays, protein splicing assays (PSA), protein complementation assays (PCA), circular permutation assays, and bioluminescence resonance energy transfer assays (BRET). Use of the ALuc of the present invention as a reporter gene essential for these assay systems can remarkably improve assay measurement performance.

The reporter-gene assay method and the two-hybrid assay, which are typical "inducible method" assay systems, are hereinafter described in detail.

(i) Reporter-Gene Assay Method

Reporter-gene assay methods have been widely used as means for analyzing activation of transcription factors in response to external stimulus and gene expression regulation, and are typically used for detecting endocrine disruptors (environmental hormones) that disturb signaling via nuclear receptors. The expression of a target gene (e.g., hormone-responsive gene) involving signaling via nuclear receptors is caused when the complex of a ligand and a receptor binds to a cis region (hormone-response element) that regulates the transcription of the gene. This assay is an assay in which a plasmid that contains a reporter gene, such as luciferase, at the downstream of the cis region of each hormone-responsive gene is introduced into cells, and the amount of the hormone molecule, which is to be a ligand, or the amount of the endocrine disruptor is detected by the amount of bioluminescence or the like.

Mammalian cells used for general gene recombination, such as COS cells, CHO-K1 cells, HeLa cells, HEK293 cells, and NIH3T3 cells, are preferably used as host cells in the reporter-gene assay method. However, yeast cells, bacterial cells, such as *Escherichia coli*, insect cells, and the like may be used. The present invention is mainly used in mammals, such as humans, in vivo, or in mammalian cells in vitro.

In the reporter-gene assay method, firefly luciferase that has been widely used has the following drawbacks: [1] due to its large molecular weight, the start of expression takes a long period of time, thereby imposing a great burden on the host cells, and [2] due to the low luminescence intensity of firefly luciferase, it generally takes from 1 day to 2 days after stimulation to accumulate a sufficient amount of luciferase (reporter). However, by selecting the ALuc of the present invention as a reporter protein, these problems are overcome. In particular, the ALuc of the present invention is excellent in maintaining a high luminescence intensity as compared to firefly luciferase or the like and having an even smaller molecular weight as compared to a conventional ALuc (e.g., ALuc30).

The use of the ALuc of the present invention as a reporter protein ensures a significantly high luminescence intensity of the reporter, and hence provides an advantage of significantly prompt measurement after the stimulation. Accordingly, the measurement time can be greatly reduced as compared to conventional reporter proteins while ensuring high temporal stability in luminescence, thereby enabling luminescence measurement even for a cell strain with insufficient gene introduction efficiency.

Specifically, the ALuc of the present invention is employed in these reporter-gene assay methods in such a manner that the luminescent enzyme is linked to a known eukaryotic cell expression vector containing a special promoter in an upstream portion, and the vector is then introduced into a eukaryotic cell. After a predetermined time, the measurement may be performed under the condition of the presence or absence of a signal (stimulation) (Takenaka, Y., Yamaguchi, A., Tsuruoka, N., et al. Molecular Biology and Evolution, 29 2012 1669.). The known pTransLucent vector may be used as the expression vector for reporter-gene assay method that can carry the ALuc of the present invention, and the ALuc may be easily incorporated therein using a known method.

(ii) Two-Hybrid Method

The two-hybrid method is one of the techniques for studying protein-protein interactions. In 1989, a yeast two-hybrid (Y2H) system using yeast (*Saccharomyces cerevisiae*) was first established. This method utilizes the fact that the DNA binding domain (GAL4 DBD) and the transcriptional activation domain (TA) of GAL4 protein, which is a transcriptional activator, are separable. Fused GAL4 DBD and protein A (bait) are expressed as a fusion protein, and simultaneously, fused transcriptional activation domain (TA) and protein B (prey) are expressed in the cell as a fusion protein. Thus, an interaction between proteins A and B can be observed. When proteins A and B bind, DBD approaches TA and the DNA binding domain (DBD) binds to the "UASG" base sequence, which promotes the expression of the reporter gene that is linked to the downstream of the sequence. When the reporter gene is luciferase, the compatibility of proteins A and B can be measured by monitoring bioluminescence in the presence of its specific substrate. This enables screening of proteins and peptides that interact with protein A (bait). The protein B (prey) used herein may be supplied from an expression library.

As host cells, in addition to yeast cells, bacteria, such as *Escherichia coli*, mammalian cells, and insect cells are used. Other than GAL4 DBD, which is a transcriptional activator derived from yeast, "LexA" or the like, which is a repressor protein derived from *Escherichia coli*, may be used. A DNA encoding such a protein is linked to a DNA encoding a bait protein (i.e., protein A described above), such as a ligand binding region of a ligand-responsive transcriptional regulator, and then linked to the downstream of a promoter capable of functioning in host cells. On the other hand, usable examples of the "transcriptional activation region of a transcriptional activator" include a GAL4 transcriptional activation region, an *Escherichia coli*-derived B42 acid transcriptional activation region, and a herpes simplex virus VP16 transcriptional activation region. A DNA encoding such a transcriptional activation region is linked to a DNA encoding a prey protein (i.e., protein B described above), and then linked to the downstream of the promoter capable of functioning in host cells.

Specifically, examples of the vector that has a DNA encoding a DNA binding region of transcriptional regulator GAL4 and that can use budding yeast as a host cell may include plasmid pGBT9 (produced by Clontech). Examples of the vector that has a DNA encoding a GAL4 transcriptional activation region and that can be used in budding yeast may include plasmid pGAD424 (produced by Clontech). In addition, examples of the vector that has a DNA encoding a GAL4 DNA binding region and that can be used in mammalian cells may include pM (produced by Clontech) and pBIND (produced by Promega). Examples of the vector that has a DNA encoding a herpes simplex virus VP16 transcriptional activation region and that can be used in mammalian cells may include pVP16 (produced by Clontech) and pACT (produced by Promega). In addition, examples of the vector that has a DNA encoding a LexA DNA binding region and that can be used in mammalian cells may include pLexA (produced by Clontech). Examples of the vector that has a DNA encoding B42 and that can be used in mammalian cells may include pB42AD (produced by Clontech).

In this case, for example, a vector in which the ALuc gene of the present invention is inserted as a reporter gene into the downstream of, for example, the region ("USAG") to which GAL4 binds may be formed. In the case of mammalian hosts, by using a commercially available pG5Luc vector (Promega) or pFR-Luc vector (Stratagene), the luciferase (ALuc) of the present invention may be easily incorporated and used by a known method in place of firefly luciferase incorporated into the vector. The luciferase (ALuc) of the present invention may also be used in place of chloramphenicol acetyltransferase (CAT) of a commercially available pG5CAT vector (Clontech).

(5-4) "Activatable" Method

The assay system carrying a bioluminescent enzyme as a reporter protein according to the "activatable" method has been also studied and developed by the inventors of the present invention as a "bioluminescent probe" technology. Examples of application of the ALuc of the present invention to a "bioluminescent probe" and an "intracellular imaging method" using the bioluminescent probe are described below as typical examples of the "activatable" method. Before the description, the "luminescent fusion protein (luminescent capsule)" developed for the first time in the present invention is described. In addition, the ALuc of the present invention can be suitably used as a reporter protein in protein-fragment complementation assays (PCA) and protein splicing assays (PSA), which are included in the "activatable" method.

(i) Production of Luminescent Fusion Protein (Luminescent Capsule)

By binding a membrane localization signal to the C-terminus of the ALuc of the present invention, the ALuc can be localized in the plasma membrane. Such a molecular design of localization in the plasma membrane allows smooth supply of the substrate and oxygen, enabling visualization of stable bioluminescence with extremely high intensity. For the visualization, it is possible to insert a polypeptide or protein gene as a cargo between the ALuc and a nucleic acid encoding the signal peptide. This allows efficient transfer of the cargo protein to the plasma membrane surface, and makes the place where the protein is transferred illuminated. One typical example is as follows. When the DEVD (SEQ ID NO: 25) sequence or IETD (SEQ ID NO: 26) sequence responsive to a cell death signal is inserted between proteins, the DEVD (SEQ ID NO: 25) sequence or IETD (SEQ ID NO: 26) sequence actively responds to the activities of caspase-3 or caspase-8 as signals at the cell death, and functions as a visualization system. The inventor of the present invention named the luminescent fusion protein with this structure a "luminescent capsule."

As compared to conventional luminescent probes, the luminescent capsule has advantages of showing stable luminescent properties with remarkably high intensity, and being responsive to a specimen that cannot pass through the plasma membrane. The luminescent capsule has a structure in which a "membrane localization signal (MLS)" is linked to the "C-terminus of the luminescent enzyme" as a basic frame structure. The effect of a compound causing a form change on the cell surface, such as a compound inducing cell death, can be visualized as a form change in the plasma membrane surface, by this structure or even when the luminescent enzyme of the present invention is tandemly linked to enhance the amount of luminescence, and hence easy observation is possible. Preferably, it is possible to insert, between the MLS and the C-terminus of the luminescent enzyme, a polypeptide causing a form change in the plasma membrane surface, or the partial recognition sequence of the peptide, specifically, for example, the full length or the partial recognition sequence of a G-protein coupled receptor (GPCR) or c-Src. In addition, by inserting a polypeptide inducing cell death or the recognition sequence of the peptide as a cargo between the MLS and C-terminus of the luminescent enzyme, cell death can be visualized. More specifically, when a peptide sequence (generally 20 amino acids or less, preferably 10 amino acids or less) recognized by caspases, proteases (e.g., serine protease and cysteine protease), or digestive enzymes (e.g., trypsin and amylase), for example, an amino acid sequence containing "DEVD" (SEQ ID NO: 25) or "IETD" (SEQ ID NO: 26) is inserted as a cargo, cell death can be visualized by caspase-3 activities. Further, by linking a fluorescent protein or another luminescent enzyme as a cargo between the luminescent enzyme and MLS, the amount of luminescence on the plasma membrane surface is increased as in the case where the luminescent enzyme of the present invention is tandemly linked, allowing easy observation of the plasma membrane form. This fusion protein even responds to a ligand that cannot pass through the plasma membrane, and hence screening with respect to various stimulations is possible.

That is, the luminescent capsule of the present invention is a luminescent fusion protein in which any protein or polypeptide, which is intended to be expressed on the plasma membrane surface, is inserted between the membrane localization signal (MLS) and the C-terminus of the ALuc of the present invention. Typical examples include:

(a) a luminescent fusion protein in which a fluorescent protein or luciferase is inserted between the membrane localization signal (MLS) and the C-terminus of the ALuc of the present invention (the luciferase may be ALuc other than that of the present invention); and (b) a luminescent fusion protein in which a polypeptide changing the form in the plasma membrane, or a polypeptide having 20 or less amino acids, preferably 10 or less amino acids recognized by the polypeptide changing the form in the plasma membrane, is inserted between the membrane localization signal (MLS) and the C-terminus of the ALuc of the present invention. In particular, the polypeptide changing the form in the plasma membrane is preferably a polypeptide inducing cell death, more preferably a polypeptide having 20 or less amino acids containing caspase or the recognition sequence of the caspase, i.e., "DEVD" (SEQ ID NO: 25) or "IETD" (SEQ ID NO: 26).

(ii) Application to Luminescent Probe

In addition, by incorporating the ALuc of the present invention into the integrated-molecule-format luminescent probe (Kim, S. B., Awais, M., Sato, M., et al. Anal. Chem., 79 2007 1874, Kim, S. B., Otani, Y., Umezawa, Y., et al. Anal. Chem., 79 2007 4820, Kim, S. B., Sato, M., Tao, H. Bioconjugate Chem., 19 2008 2480, Kim, S. B., Sato, M., Tao, H. Anal. Chem., 81 2009 67, U.S. Pat. Nos. 8,124,424, 8,043,827, US 2009-0269781 A1, and WO 2008/084869 A1) or the two-molecule-format luminescent probe (Kim, S. B., Kanno, A., Ozawa, T., et al. ACS Chem. Biol., 2 2007 484, and Kim, S. B., Ozawa, T., Watanabe, S., et al. Proc. Natl. Acad. Sci. U.S.A, 101 2004 11542.) according to the inventions of the patent applications already filed by the inventors of the present invention, the presence or absence of ligand and the intensity of ligand activity can be observed with high luminance. By comprising, as the probe components, [1] the bisected luminescent enzyme (N- and C-terminal fragments), and [2] a ligand-binding protein responsive to the target ligand and [3] a recognition protein that recognizes the binding of the ligand with the ligand-binding protein, which are linked to the vicinity of the bisected luminescent enzyme, it is possible to form a high-performance luminescent probe. This luminescent probe can function such that, when the recognition protein recognizes the ligand binding of the ligand-binding protein, the two adjacent fragments of the bisected enzyme complement each other and thereby change the enzymatic activity. Here, due to the high luminescence intensity and stability of the bisected enzyme, it is possible to perform reliable measurement with an improved detection limit.

In the present invention, the "integrated molecule-format luminescent probe" means a known bioluminescent probe in which all components for visualization imaging are integrated in a single fusion molecule (U.S. Pat. Nos. 8,124,424 and 8,043,827). For example, the "integrated molecule-format luminescent probe" means a fusion protein that comprises, as fundamental components, the two fragments of N- and C-terminals obtained by bisecting the ALuc of the present invention, a ligand-binding protein, and a recognition protein for recognizing the ligand-binding protein. Similarly, the "two molecule-format luminescent probe" means a bioluminescent probe in which the two fragments of N- and C-termini obtained by bisecting the ALuc of the present invention are present in the fusion protein containing the ligand-binding protein, and in the fusion protein containing the recognition protein, respectively.

When the ALuc of the present invention is used for these bioluminescent probes, the ALuc needs to be bisected into an N-terminal fragment and a C-terminal fragment. The bisected position may be a position corresponding to a cleavage position in a known ALuc.

A specific method of using the superluminescent enzyme of the present invention as an integrated molecule-format luminescent probe is in accordance with a method described in detail in (U.S. Pat. Nos. 8,124,424, 8,043,827, US 2009-0269781 A1, or WO 2008/084869 A1). Specifically, the luciferase (ALuc) of the present invention is bisected, and a chimera DNA encoding a luminescent probe in which a ligand-binding protein and a peptide sequence, which recognizes the change in steric structure upon binding of a ligand to the protein, are linked in a linear chain form is designed. In general, the chimera DNA is subcloned into a vector suitable for the cells in which the chimera DNA is intended to be expressed, and the vector is introduced into the cells to be expressed. However, the chimera DNA may be ligated to a control sequence at an upstream portion to be directly introduced into the cells. The target cells are preferably mammalian-derived cells, such as human cells. Other suitable examples may include cells that exist in a living subject, and culture cells that retain the native function, yeast cells, insect cells, and prokaryotic cells such as *Escherichia coli*. The specific type of the vector is also not particularly limited. A suitable vector capable of being expressed in the target host cells for expression is appropriately selected. The introduction of the vector into the cells may be performed using a known transfection method, such as a microinjection method or an electroporation method, or a transfection method using a lipid (e.g., BioPORTER (Gene Therapy Systems, Inc.) or Chariot (Active Motif)).

The bioluminescent probe using the superluminescent enzyme of the present invention is introduced into cells as a chimera DNA and then expressed in the cells as a fusion protein, and hence by measuring the change in light amount emitted from the cells after subjecting the transformed cell to ligand stimulation, for example, the property or levels of activity of the ligand may be evaluated.

When the superluminescent luciferase (ALuc) of the present invention is incorporated in the bioluminescent probe, the "ligand-binding protein," which can be incorporated in the probe together with the ALuc, is intended to mean a protein that binds with a ligand at the ligand binding site. The ligand-binding protein may serve to, in response to the binding with the ligand, for example, change the steric structure, cause phosphorylation, or facilitate protein-protein interaction. Examples of such ligand-binding proteins include nuclear receptors (NR) to which such ligands as hormones, chemical substances, or signaling proteins bind; cytokine receptors; and various protein kinases. A suitable ligand-binding protein is selected depending on the target ligand. The ligand that binds to the ligand-binding protein is not particularly limited as long as the ligand binds to the ligand-binding protein. The ligand may be an extracellular ligand that is introduced from outside the cells to inside the cells, or an intracellular ligand that is produced inside the cells in response to extracellular stimulus. Examples thereof may include agonists or antagonists of the receptor protein (for example, nuclear receptor, or G-protein-coupled receptor), and signaling proteins, such as cytokines, chemokines, or insulin, intracellular second messenger, lipid second messenger, phosphorylated amino acid residue, G-protein-coupled receptor ligand, and other ligands that specifically bind to proteins involved in intracellular signaling.

For example, when the intracellular second messenger, the lipid second messenger, or the like is used as a ligand, the binding domain of each second messenger may be used as the ligand-binding protein. The "second messenger" means a different kind of intracellular signaling substance that is newly produced as a result of the binding of the extracellular signaling substance, such as a hormone or a neurotransmitter, with a receptor that exists in the plasma membrane. Examples of the second messenger include cGMP, AMP, PIP, PIP2, PIP3, inositol trisphosphate (IP3), IP4, $Ca^{2+}$, diacylglycerol, and arachidonicacid. For example, for $Ca^{2+}$ as the second messenger, calmodulin (CaM) may be used as the ligand-binding protein.

In addition, as a method of using the enzyme of the present invention as an integrated-molecule-format bioluminescent probe, the enzyme may be used as a fusion protein described in Japanese Patent Application No. 2009-200413 or Japanese Patent Application No. 2010-018759.

(iii) Intracellular Imaging

In addition, the use of the gene encoding the ALuc enables stable introduction of the ALuc into various cell strains. For example, the use of the gene enables stable introduction of the ALuc into the undifferentiated embryonic cells, ES cells, or induced pluripotent stem cells (iPS cells). The cells do not emit light themselves, and hence it has been very difficult to research the intracellular molecular phenomenon and tissue specificity of the cells. In order to address this difficulty, a molecular probe containing the ALuc is introduced into somatic cells before the embryo is formed, and then the embryo is differentiated into various tissues. This enables measurement of specific molecular phenomena in respective organs with high sensitivity.

This process is performed according to the method of Yamanaka et al. (Okita K., Ichisaka, T., Yamanaka, S. Nature, 448 2007 313).

In addition, by linking the ALuc of the present invention to a suitable signal peptide, the ALuc can be used for luminance imaging of various organelles. For example, by linking a GAP-43-derived "MLCCMRRTKQV sequence" (SEQ ID NO: 27) to an N- or C-terminus of ALuc, the ALuc may be localized in the plasma membrane. Linking of a "GRKKRRQRRR sequence" (SEQ ID NO: 28) to a terminus enables localization in cell cytoplasm. In addition, for localization in endoplasmic reticulum (ER) and cellular nucleus, a "KDEL sequence" (SEQ ID NO: 29) and a "DPKKKRKV sequence" (SEQ ID NO: 30), respectively, are linked to a terminus. Further, by linking to an antigen site, such as a HIS-tag (HHHHHH) (SEQ ID NO: 19), a FLAG-tag (DYKDDDDK) (SEQ ID NO: 20), a Myc-tag (EQKLISEEDL) (SEQ ID NO: 21), an HA-tag (YPYDVPDYA) (SEQ ID NO: 22), a V5-tag (GKPIPNPLLGLDST) (SEQ ID NO: 23), or a T7-tag (MASMTGGQQMG) (SEQ ID NO: 24), the ALuc can be used for immunostaining or separation/purification in acellular systems. In these usages, known techniques such as immunostaining or immunocytochemistry may be adopted.

Even when an artificial bioluminescent enzyme (ALuc) is newly established as in the present invention, the optimization of a luminescence reaction solution is another object in order to provide an optimal luminescence reaction field. Bioluminescence is an oxidation reaction caused by the following four elements: a luminescent enzyme, a substrate, oxygen ($O_2$), and a reaction solution (including a cofactor). Therefore, in order to provide the ALuc with the optimal luminescence reaction field, the four elements need to be suitably controlled. With regard to the substrate among the four constituent elements, an excellent substrate can be developed through synthesis research. Oxygen may not be particularly added in the field of a luminescence reaction. The optimization of the "luminescent enzyme and reaction solution" as other controllable elements is important for achieving a high luminescence intensity property and luminescence stability of bioluminescence.

A reason why the reaction solution is important is that the reaction solution constitutes the "optimal luminescence reaction field." In the reaction field, each constituent element contributes to luminescence. However, despite the importance of the reaction solution, the constituent factors of the reaction solution are diverse and the number of additives is large, and hence it is difficult to create an optimal reaction system in a given luminescence reaction system. The constituent factors are diverse, including the kind of a buffer (Tris, phosphate, or the like), ions (cation and anion), a hydrogen concentration (pH), a surfactant, an antioxidant, a stabilizer, a sugar, and the like, and hence it is an extremely difficult object to create optimal composition in all of these constituent factors.

Figure 5:
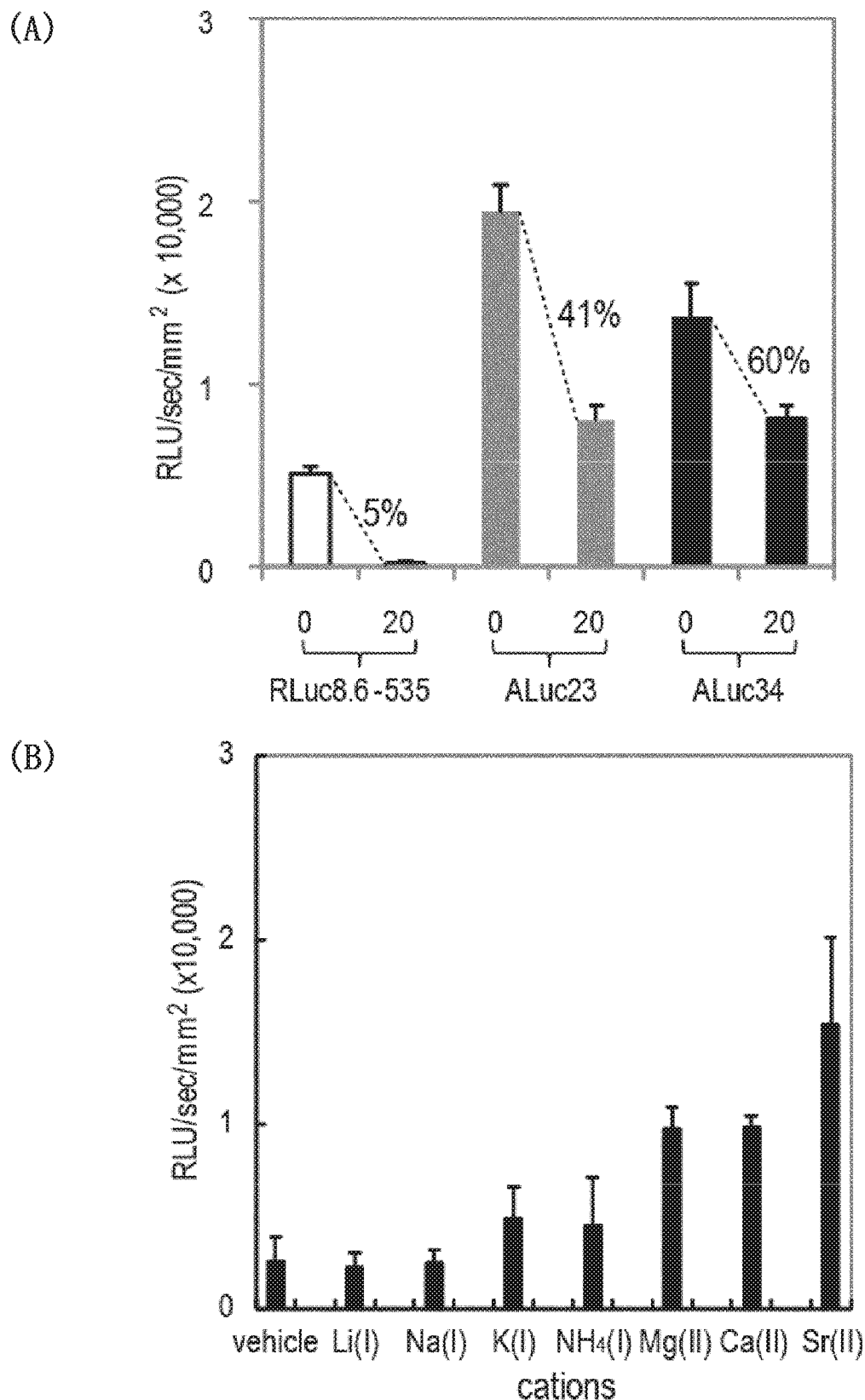
FIG. 5(A) is a graph for showing the optical stability of bioluminescent enzymes. A percentage represents an optical intensity remaining after 20 minutes as compared to the initial intensity.
FIG. 5(B) is a graph for showing relative optical intensities of ALuc16 according to monovalent and divalent metal cations in a Tris-HCl buffer.

In order to constitute the above-mentioned optimal luminescence reaction solution, the kind of the added cation (FIG. 5, FIG. 6, and FIG. 22), the concentration of the cation (FIG. 7), the time course of the luminescence intensity (FIG. 8 and FIG. 23), the kind of the substrate (analog) (FIG. 15), and the like were studied to investigate the composition of the luminescence solution optimal for the novel ALucs. The composition of the luminescence solution found through the investigation is described below.

6. Buffer for Bioassay
(6-1) Buffer Component 1 (HBSS Buffer) Serving as Basic Buffer Component As a buffer to be used for the ALuc of the present invention, an HBSS buffer (Hanks' balanced salt solution) may be used as a basic composition. The HBSS buffer may be prepared in accordance with a known protocol (e.g., see the website of National Institute of Biomedical Innovation, Health and Nutrition at cellbank.nibio.gojp/legacy/sheet/att00011.htm), as described below.

First, the following four types of solutions are prepared beforehand, and mixed for use.

Solution 1: 1.4% $NaHCO_3$ solution
Solution 2: a solution prepared by dissolving 80.0 g of NaCl, 4.0 g of KCl, 2.0 g of $MgSO_4.7H_2O$, 0.6 g of $Na_2HPO_4.2H_2O$, 10.0 g of glucose, and 0.6 g of $KH_2PO_4$ in 800 ml of water
Solution 3: a solution prepared by dissolving 1.4 g of $CaCl_2$ in 100 ml of water
Solution 4: a solution prepared by weighing 0.4 g of phenol red, making it into a paste with a small amount of water, and adding water thereto to give 150 ml of a solution The mixture is adjusted to a pH of 7.0 with a sodium hydroxide solution (N/20) so as to give 200 ml.

For use, 2.5 ml of solution 1, 8 ml of solution 2, 1 ml of solution 3, and 1 ml of solution 4 are added to 87.5 ml of sterile water. When phenol red is not used, the mixing of solution 4 may be omitted.

(6-2) Buffer Component 2 (Tris buffer) Serving as Basic Buffer Component

The Tris buffer refers to a widely used conventional buffer component (herein, the "tris" is an abbreviation for tris (hydroxymethyl)aminomethane, which is typically prepared by adding HCl to 10 mM of a tris salt to thereby adjust the pH, and optionally adding 1 mM of EDTA thereto as an additive), and is used in a variety of biological studies because of its high biocompatibility. Nonetheless, there has been insufficient study of the effects of the Tris buffer on a bioluminescent reaction.

In the ALuc of the present invention, the Tris buffer can be suitably used for bioluminescence, and can be used as a basic buffer component usable in both cell lysis and assay.

(6-3) Buffer Formulation in the Present Invention

The above-mentioned basic buffer components, the HBSS buffer and the Tris-buffer, may be used in combination thereof. These buffers are mixed at a ratio of from 20 to 50:from 50 to 20, preferably from 40 to 60:from 60 to 40, most preferably 60:40 in volume % (v/v).

As the surfactant, NP-40, TW80, and SDS are used in combination thereof. The NP-40, TW80, and SDS are mixed at a ratio of 1:from 0.1 to 1:from 0 to 0.5, preferably from 1 to 2:from 0.5 to 2:from 0.1 to 1, most preferably 1:1:0.1 in volume % (v/v).

The surfactant TW80 is mixed with other surfactants and the ratio is adjusted to be from 1% (v/v) to 10% (v/v), preferably from 5% (v/v) to 10% (v/v).

As a polyol, polyethylene glycol (PEG), and a sugar component (sucrose or glucose) are used in combination thereof. PEG400 is contained in an amount of from 0.01% (v/v) to 10% (v/v), and the sugar component (sucrose or glucose) is contained in an amount of from 0 mg/mL to 20 mg/mL. PEG400 is preferably contained in an amount of from 0.1% (v/v) to 10% (v/v), and the sugar component (sucrose or glucose) is preferably contained in an amount of from 2 mg/mL to 10 mg/mL.

As a heavy metal, Fe(III), Cu(II), Mo(VI), and Zn(II) may be contained alone or in combination thereof in a concentration within a range of from 0.01 PPM to 1 PPM, preferably 1 PPM.

Halogen ions $Br^-$ and $I^-$ may be contained alone or in combination thereof in a concentration of from 1 mM to 100 mM, preferably from 50 mM to 100 mM.

It is more preferred to optionally add a reducing agent, such as vitamin C, to improve the luminescence stability.

7. Bioassay of Interest for Artificial Luciferase of the Present Invention

As bioassays to which the ALuc of the present invention is applicable, for example, the following known methods may be given. However, the bioassays to which the ALuc of the present invention is applicable are not limited to the following.

(1) Reporter-gene assay method, (2) two-hybrid assay, (3) enzyme-linked immunosorbent assay, (4) radioimmunoassay (RIA), (5) FRET method utilizing fluorescence resonance energy transfer between fluorescent proteins (FRET), (5) protein complementation assay (PCA), (6) integrated-molecule-format bioluminescent probe; or simply single-chain probe, (7) circular permutation substitution probe, (8) molecular strain sensor (molecular tension-indexed bioluminescent probe), (9) multiple recognition-type bioluminescent probe, and (10) multicolor bioluminescent imaging probe set.

8. Measuring Procedure and Measuring Apparatus Used in Test Using Artificial Luciferase of the Present Invention The luminescence activity may be measured in accordance with an apparatus and an operation method for a typical bioluminescence assay, and conventional protocols are applicable without any restriction.

Luminometers (e.g., MiniLumat LB 9506 (Berthold); and GloMax 20/20n (Promega)) have typically been used to measure bioluminescence intensity. A lysate buffer is poured over cultured cells in a plate to thereby produce a cell lysate. After the cell lysate is mixed with a substrate, the luminescence is immediately measured.

In order to measure the ligand activity of cultured cells in a 96-well plate, a ready-made bioluminescence plate reader (e.g., Mithras LB 940 (Berthold); and SH-9000 (Corona)) may be used. Using a substrate solution autoinjector attached to the plate reader, a substrate may be instantaneously introduced, and bioluminescence generated by the expressed probe may be instantaneously measured in the presence of the ligand.

9. Analyte of Interest in Bioassay

Examples of analytes in these bioassays include organic or inorganic compounds (particularly low molecular weight compounds), proteins having bioactivity, and peptides. These substances may be those whose function and structure are known or unknown. A "combinatorial chemical library" is an effective means as a group of analytes for efficiently identifying target substances. The preparation and screening of a combinatorial chemical library are well known in the art (see, e.g., U.S. Pat. Nos. 6,004,617 and 5,985,365). Alternatively, a commercially available library may be used (e.g., libraries available from ComGenex (US), Asinex (Russia), Tripos, Inc. (US), ChemStar, Ltd. (Russia), 3D Pharmaceuticals (US), and Martek Biosciences). By applying a combinatorial chemical library to a cellular cluster for expressing the probe, so-called "high-throughput screening" may be carried out.

10. Terms and Concepts Used in the Present Invention

The other terms and concepts used in the present invention are specifically defined in the descriptions of embodiments and Examples of the invention. The terms are generally selected from the IUPAC-IUB Commission on Biochemical Nomenclature, or based on interpretations of idiomatic terms and words in the related field. Except for the technologies with apparent sources, the various technologies used to carry out the present invention may be easily and consistently performed by one of ordinary skill in the art with reference to published literatures and the like. For example, genetic engineering and molecular biological technologies may be carried out according to: the methods described in: J. Sambrook, E. F. Fritsch & T. Maniatis, "Molecular Cloning: A Laboratory Manual (2nd edition)," Cold Spring Harbor Laboratory Press, Cold Spring Harbor, N.Y. (1989); D. M. Glover et al. ed., "DNA Cloning," 2nd ed., Vols. 1 to 4, (The Practical Approach Series), IRL Press, Oxford University Press (1995); Ausubel, F. M. et al., Current Protocols in Molecular Biology, John Wiley & Sons, New York, N.Y., 1995; Japanese Biochemical Society ed., "Zoku Seikagaku Jikken Koza 1 [Continuation of Biochemistry Experimental Series 1], Idensi Kenkyu Ho [Gene Study Method] II," Tokyo Kagaku Dojin (1986); Japanese Biochemical Society ed., "Shin Seikagaku Jikken Koza 2 [New Biochemistry Experimental Series 2], Kakusan [Nucleic Acid] III (Kumikae DNA Gijutsu [DNA Recombinant Technology])," Tokyo Kagaku Dojin (1992); R. Wu ed., "Methods in Enzymology," Vol. 68 (Recombinant DNA), Academic Press, New York (1980); R. Wu et al. ed., "Methods in Enzymology," Vols. 100 (Recombinant DNA, Part B) & 101 (Recombinant DNA, Part C), Academic Press, New York (1983); R. Wu et al. ed., "Methods in Enzymology," Vols. 153 (Recombinant DNA, Part D), 154 (Recombinant DNA, Part E), & 155 (Recombinant DNA, Part F), Academic Press, New York (1987); and the like; the methods described in the literatures cited in these literatures; or other various similar methods and modified methods thereof that are substantially the same as the disclosed methods. The proteins, peptides, and DNAs encoding them used in the present invention are available from existing databases (e.g., www.ncbi.nlm.nih.gov).

In addition, the patent literatures and the non patent literatures described herein are incorporated herein by reference.

EXAMPLES

The present invention is described in more detail below by way of Examples. However, the technical scope of the present invention is not limited to Examples below.

Example 1

<Experiment> EF-Hand-Like Regions of ALucs

The inventors of the present invention recently created a series of artificial luciferases (ALucs) by linking frequently occurring amino acids in the alignment of copepod luciferase sequences from zooplankton samples (Non Patent Literatures 4 and 7). The molecular structure of ALuc30 in FIG. 2(A) was previously predicted by a template-based modeling of the amino acid sequence (Non Patent Literature 7 and Izumi, H., et al., Data Mining of Supersecondary Structure Homology between Light Chains of Immunoglobulins and MHC Molecules: Absence of the Common Conformational Fragment in the Human IgM Rheumatoid Factor. Journal of Chemical Information and Modeling, 2013. 53(3): p. 584-591.). The detailed procedure of the present template-based modeling (TBM) approach was previously demonstrated.

In brief, the inventors of the present invention reviewed the known crystallographic information of existing marine luciferases available from public databases. It was found that ALucs share the highest sequence homology with the coelenterazine-binding protein (CBP) derived from *Renilla muelleri* (PDB id: 2hps and 2hq8) (16.7%) among structure-available luciferases in the databases. Thus, CBP was chosen for the molecular-structural template of ALucs. The sequence of CBP was aligned with the sequence of ALuc30 in the view of the supersecondary structure code (SSC). In the alignment, all consensus amino acids in CBP were first substituted with ones of ALuc30. Finally, the molecular structure of ALuc30 was optimized by a molecular mechanics (MM) method based on a Polak-Ribiere algorithm.

Figure 2:
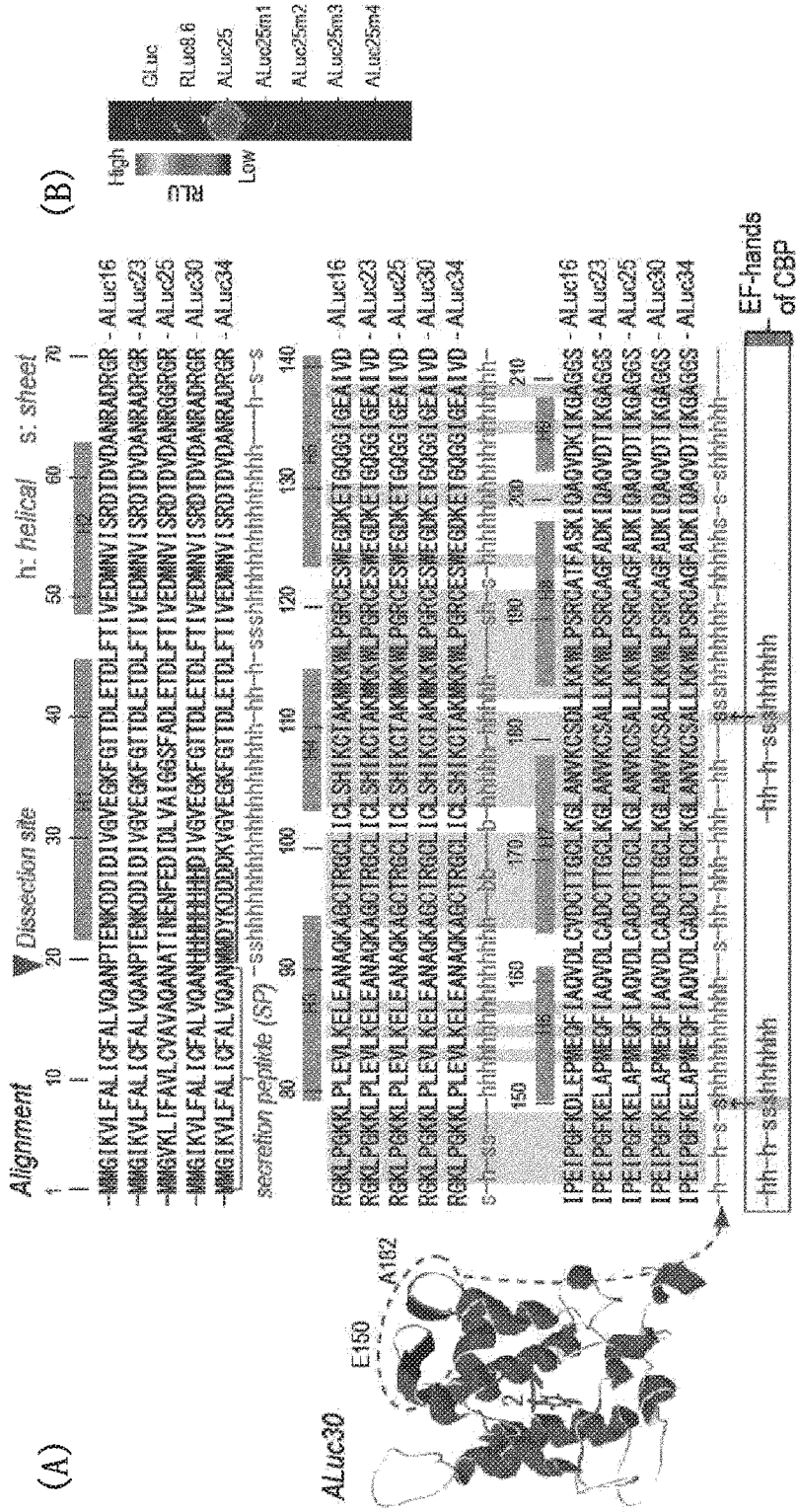
FIGS. 2(A) and 2(B) are an illustration of detailed projection of the putative supersecondary structures of ALuc30.

The inventors of the present invention performed multiple sequence alignments of ALucs with typical $Ca^{2+}$-binding proteins using ClustalW 2.1 (SFI). The alignment revealed putative EF-like motifs, a unique, repeated SSC pattern showing a helix-loop-helix structure (FIG. 2 and FIG. 3).

Point-Mutation of ALuc25 for Ensuring Key Amino Acids pcDNA3.1 plasmids encoding ALuc25 mutants were generated by a site-directed mutagenesis technique, called "QuikChange", via PCR and appropriate primers (FIG. 2(B)) (Sawano, A. and A. Miyawaki, Directed evolution of green fluorescent protein by a new versatile PCR strategy for site-directed and semi-random mutagenesis. Nucleic Acids Res., 2000. 28(16): p. e78.). The mutants were named ALuc25 m1 (mutation sites: E150Y, A182Y), m2 (mutation sites: E150W, A182W), m3 (mutation site: E150Y), and m4 (mutation site: E150W). As per the references, the same pcDNA3.1 plasmids encoding GLuc and RLuc8.6-535 were prepared. Aliquots of the plasmids were transiently transfected into COS-7 cells with a lipofection reagent, TransIT-LT1 (Mirus). Sixteen hours after transfection, the cells were lysed with a lysis buffer (Promega), and an aliquot (10 µL) of the lysate was transferred to an optical bottom 96-well plate. Immediately after simultaneous injection of a specific substrate (native coelenterazine; nCTZ) into the plate, the optical intensities were estimated with an image analyzer (LAS-4000, FujiFilm).

<Results and Discussion>
EF-Hand-Like Structure of ALucs is Pivotal Site for ALuc Activity.

Figure 3:
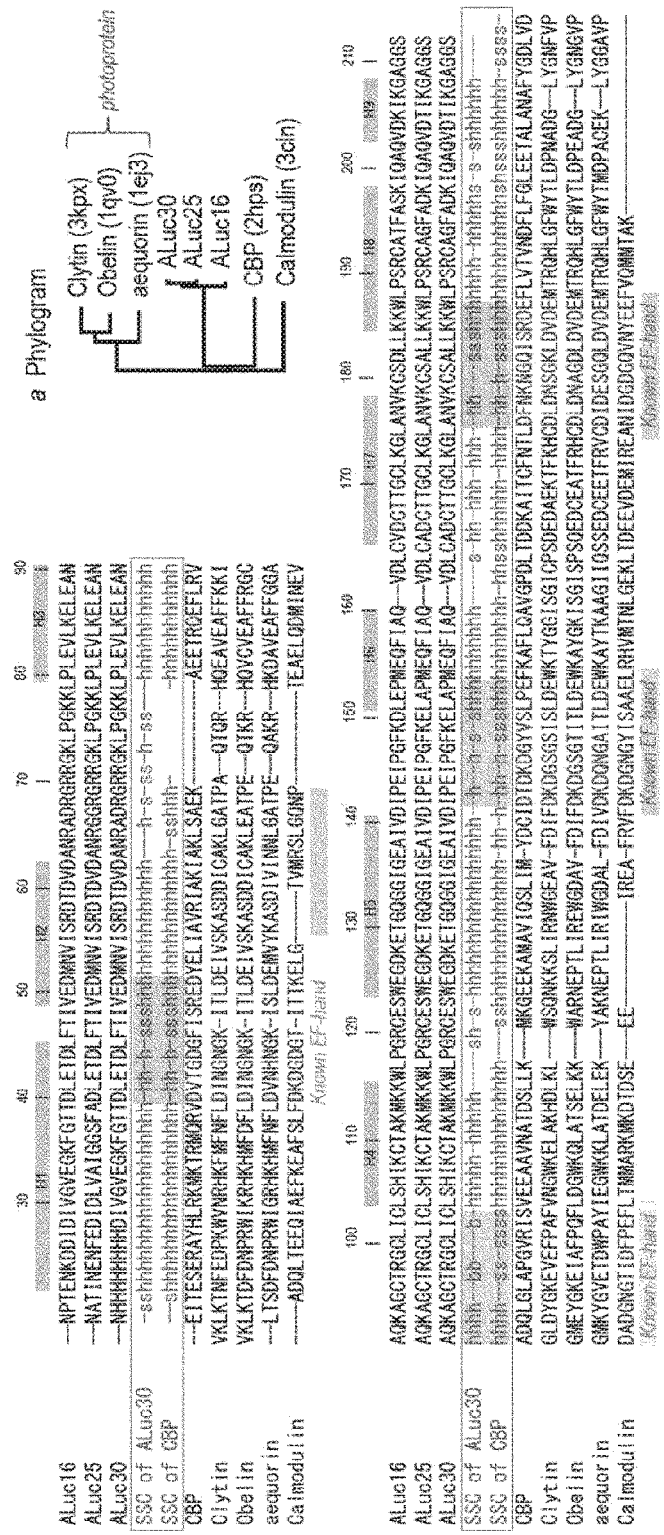
FIG. 3 is an illustration of multiple alignment of ALucs and Ca2+-binding protein sequences: ALuc16 (SEQ ID NO: 31); ALuc25 (SEQ ID NO: 33); ALuc30 (SEQ ID NO: 34); CBP (SEQ ID NO: 36); Clytin (SEQ ID NO: 37); Obelin (SEQ ID NO: 38); aequorin (SEQ ID NO: 39); Calmodulin (SEQ ID NO: 40). In the sequences, the SSC codes "h" and "s" mean helix and sheet structures, respectively. In the alignment, correlations between helix-loop-helix structures of ALucs, and known EF-hands of Ca2+-binding proteins are highlighted. A sequence number and a gray bar represent an amino acid number and a helical region of ALucs, respectively. The amino acid sequences of EF-hands are highly variable, but share the same SSC codes as shown in red series in the alignment. In inset a, a phylogram of ALucs, photoproteins, and other Ca2+-binding proteins is illustrated. Information on the EF-hand regions was obtained from the following references:(1) Gifford et al. Biochemical Journal 2007, 405, 199; (2) Titushin et al. Photochemical & Photobiological Sciences 2008, 7, 189; and (3) Oishi et al. FEBS Letters 1992, 307, 272). ALucs have a relatively high homology with the coelenterazine-binding protein (CBP).

We performed multiple sequence alignments of ALucs with typical $Ca^{2+}$-binding proteins using ClustalW 2.1 (SFI) (FIG. 3). Although the binding proteins of ALucs had a poor sequence homology with natural luciferase and $Ca^{2+}$, the alignment of the SSC sequences revealed a unique, repeated SSC pattern showing a helix-loop-helix structure (FIG. 2(A) and FIG. 3), which appeared at the corresponding sites of the known EF-hand structure of $Ca^{2+}$-binding proteins like coelenterazine-binding protein (CBP) (Petri, E. T., et al., Structure of the EF-hand domain of polycystin-2 suggests a mechanism for $Ca^{2+}$-dependent regulation of polycystin-2 channel activity. Proc. Natl. Acad. Sci. U.S.A, 2010. 107 (20): p. 9176-9181). The structure is rare among non-$Ca^{2+}$-binding proteins.

Point mutations in the amino acids (E150Y, A182Y, E150W, and A182W) in the proposed EF-hand-like structure completely destroyed the optical intensities of ALuc25 (FIG. 2(B)). These results suggested that the EF-hand-like structure was a structural core of ALuc activities.

Although we discuss results from different ALucs in this research, we expected that the results are common optical features of ALucs, considering the sequential similarity therebetween (FIG. 1 and FIG. 2(A)). For instance, the only difference between ALuc30 and ALuc34 is the epitope sequence at amino acids 20 to 27 (underlined).

Example 2

<Experiment> Proton-Dependent Optical Intensities of ALucs

Figure 4:
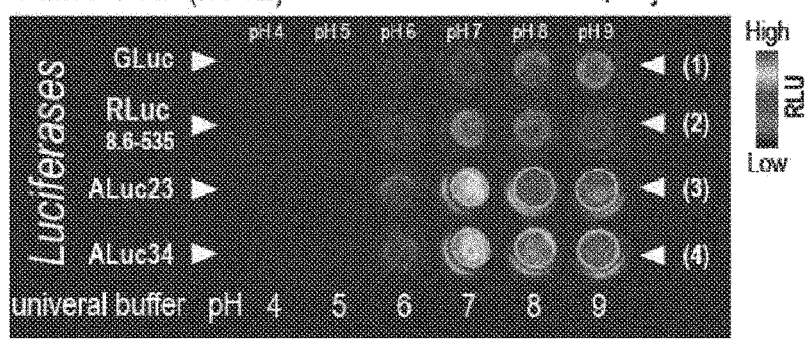
FIG. 4 are an image, an illustration, and graphs for showing the proton-driven optical properties of ALucs.
Figure 4:
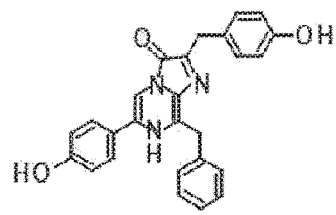
Figure 4:
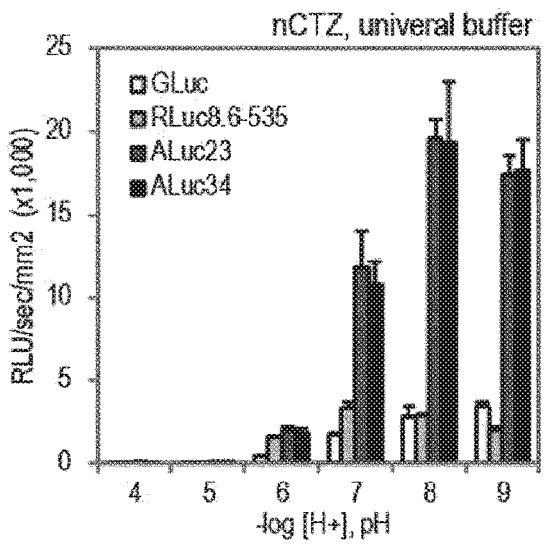
Figure 4:
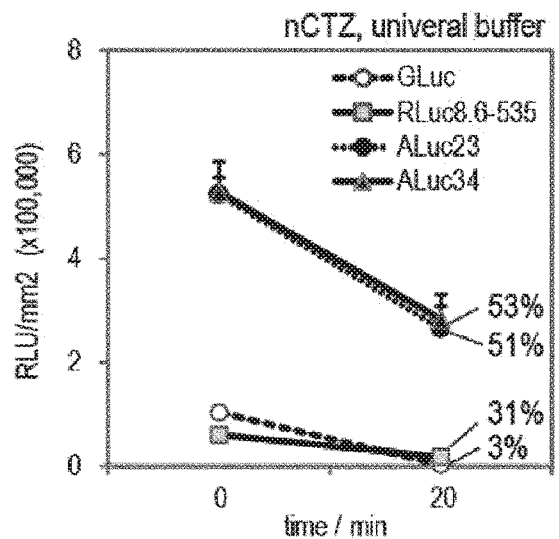

The proton-driven optical intensities of ALucs were calculated to help elucidate the proton-bioluminescence relationship (FIG. 4). African green monkey kidney-derived COS-7 cells were cultured in a 96-well plate, and transfected with a pcDNA3.1(+) vector (Invitrogen) encoding Gluc, RLuc8.6-535, ALuc23, or ALuc34. The cells were cultured and lysed by the same method as that of FIG. 2(B). Then, 10 µL of the lysates in the plate were simultaneously mixed with 40 L of the substrate solution, which was prepared by mixing a native coelenterazine (nCTZ) stock (FIG. 4(B)) with an aliquot of the universal buffer with the pH ranging from 4 to 9 (final concentration of the substrate: 0.1 mg/ml). Immediately after the substrate injection, the plate was moved into an image analyzer (LAS-4000, FujiFilm), and relative optical intensities were integrated for 30 seconds. The time course of the intensities was estimated every 5 minutes for 20 minutes (FIG. 4(D)).

<Results and Discussion> Low Proton Concentrations Elevate Optical Intensities of ALucs In order to elucidate the smallest cation (H+)-driven feature of ALuc activity, the optical intensities according to the proton concentrations (pH) were measured (FIG. 4). In the lower pH region, such as pH 4 and pH 5 (acidic condition), the optical intensities were suppressed to the background level. In contrast, the optical intensities of ALuc23 and ALuc34 were dramatically elevated at pH 7 up to about 5 fold, as compared to pH 6 (FIG. 4(C)). The ALucs sustained 51% to 53% of the initial optical intensities, even after 20 minutes at pH 9, at which GLuc and RLuc8.6-535 showed poor optical stability and retained less than 30% of the initial intensities after 20 minutes (FIG. 4(D)).

The corresponding feature of ALucs was observed under coexistence with a coelenterazine analog (FIG. 4(A)). The maximal optical intensities were obtained at pH 9, and the intensities were 41% (ALuc23) and 60% (ALuc34) of the initial intensities, even 20 minutes after the substrate injection (FIG. 4(A)).

This pH-driven elevation of ALuc activities is highly distinctive from those of other marine luciferases, such as *Oplophorus* (shrimp) luciferase (OLuc), *Gaussia* (copepod) luciferase (GLuc), *Cypridina* luciferase (CLuc), and *Periphylla* luciferase (PLuc). The maximal optical intensities of the other marine luciferases are generally found at about pH 7.5, quickly decrease at a pH higher than pH 8, and lose much of the intensity at about pH 9 (Non Patent Literature 1 and Inouye, S. and S. Sasaki, Overexpression, purification and characterization of the catalytic component of *Oplophorus* luciferase in the deep-sea shrimp, *Oplophorus gracilirostris*. Protein Expression and Purification, 2007. 56(2): p. 261-268; Ruecker, O., et al., *Gaussia*-luciferase as a sensitive reporter gene for monitoring promoter activity in the nucleus of the green alga *Chlamydomonas reinhardtii*. Molecular Genetics and Genomics, 2008. 280(2): p. 153-162.).

The pKa value of the hydroxyl groups of nCTZ is about 7.6 in an aqueous solution phase (aqueous phase) (Ohmiya, Y. and T. Hirano, Shining the light: The mechanism of the bioluminescence reaction of calcium-binding photoproteins. Chemistry & Biology, 1996. 3(5): p. 337-347.), and hence nCTZ is considered to be in a deprotonated, anionic form at about pH 9 (FIG. 4). The highest optical intensities of ALucs at pH 9 strongly suggest that ALucs provide an optical platform for accommodating anionic nCTZ and its analogs, as compared to other luciferases (FIG. 4(B)).

Example 3

<Experiment> Metal Cation-Driven Optical Intensities of ALucs

Figure 6:
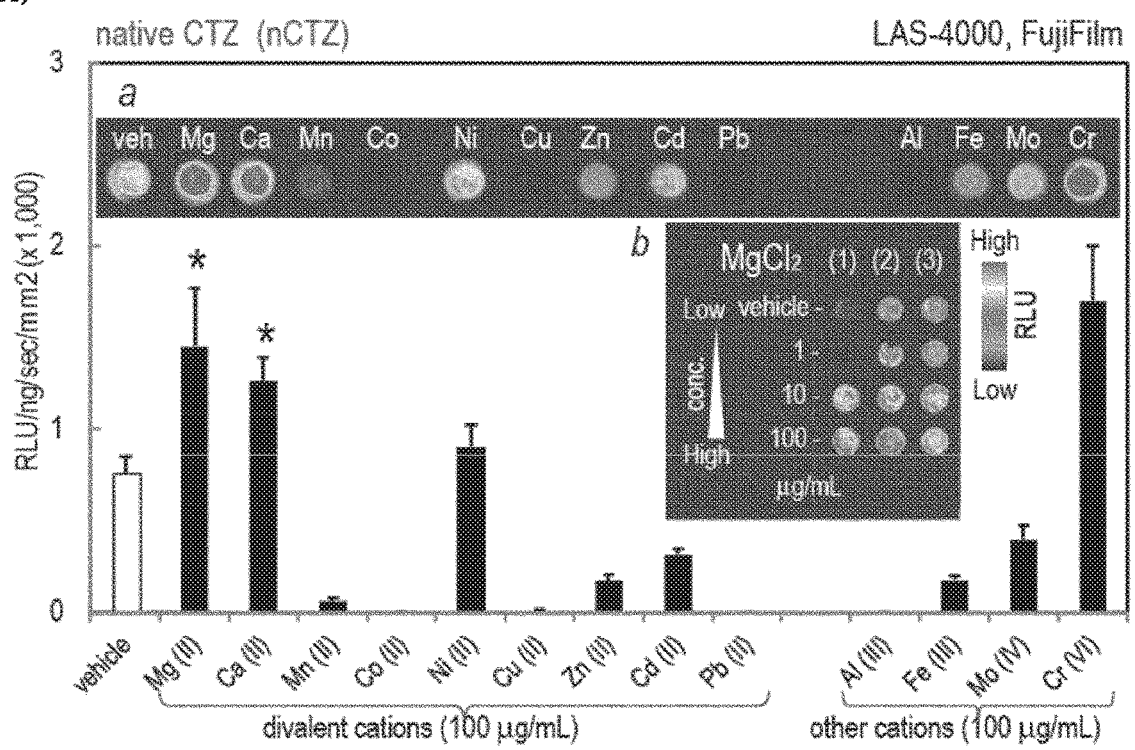
FIG. 6 are graphs for showing metal cation-driven optical intensities of ALuc16.
Figure 6:
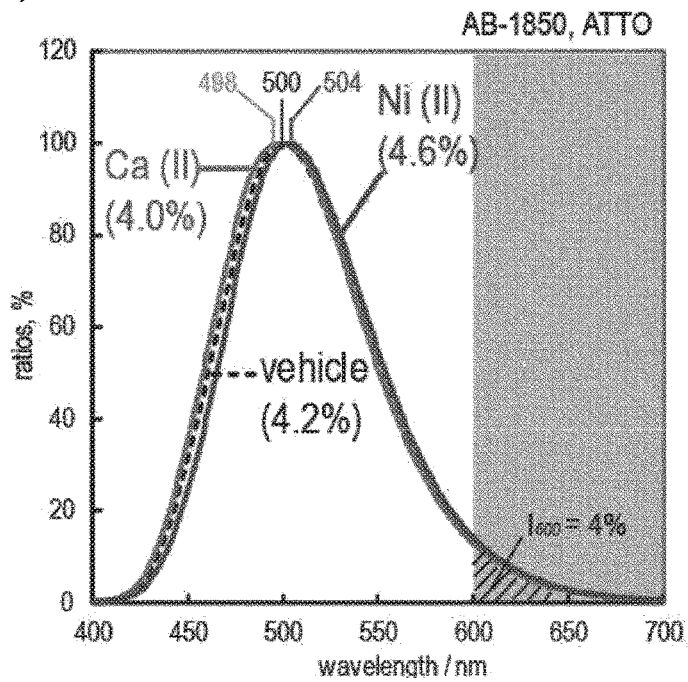

The metal cation-driven optical properties were estimated with ALuc16 (FIG. 6). A metal cation-free sample of ALuc16 was prepared beforehand as follows: we first generated a DNA construct of ALuc16 carrying a Strep-II tag at the C-terminus via PCR. The construct was then cloned into a pOPTHM vector (providing a cleavable N-terminal $His_6$-MBP tag), and expressed in the bacterial strain Shuffle T7 Express (New England Biolabs) with 0.3 mM IPTG induction. The cells were resuspended and sonicated in an ice-cold lysis buffer (50 mM Tris-HCl pH 8.0, 500 mM KCl, 5 mM imidazole, 0.2 mg/mL HEWL, 1 EDTA-free protease inhibitor cocktail tablet (produced by Roche Diagnostics)). The lysate was centrifuged at 18,000 rpm for 40 minutes, and then the supernatant was passed over a 5 mL HisTrap HP column (GE Healthcare). An AKTA Purifier system (GE Healthcare) was used to wash the column and elute the ALuc16 fusion protein as follows: the column was washed with 100 mL of a wash buffer (20 mM Tris-HCl pH 8.0, 50 mM potassium phosphate pH 8.0, 100 mM NaCl, and 15 mM imidazole pH 8.0), and then eluted in an imidazole gradient (15 mM to 300 mM) over 80 mL. The eluted sample was dialyzed to a metal-cation-free Tris-HCl buffer (0.05 M, pH 8.2) at 4° C. for 24 hours, and finally adjusted to a concentration of 1 mg/ml by dilution.

The purified ALuc16 stock was further diluted 500-fold to 2 μg/mL with the metal-cation-free Tris-HCl buffer (0.05 M, pH 8.2) before experiments. Then, 45 μL of the mixture was mixed with 5 μL of varying concentrations of a metal cation (Ca(II), Mg(II), Mn(II), Co(II), Ni(II), Cu(II), Zn(II), Cd(II), Pb(II), Al(III), Fe(III), Mo(IV), or Cr(VI)) in a 96-well optical bottom plate (Nunc) for the experiment of FIG. 6(A) (Solution A). Meanwhile, the corresponding substrate solution carrying nCTZ (Promega) was diluted 100-fold with the cation-free Tris-HCl buffer (Solution B). 50 μL of Solution B was simultaneously injected into Solution A in the 96-well plate with a multichannel micropipette (Gilson). The microplate was immediately moved to an image analyzer (LAS-4000, FujiFilm) equipped with a cooled charge-coupled device (CCD) camera, and the optical intensities were simultaneously estimated in a precision mode. The measurements were conducted in triplicate (n=3). The optical images were analyzed with Multi Gauge V3.2 (FujiFilm).

The corresponding bioluminescence spectra (FIG. 6(B)) were also measured using the same method as that of FIG. 6(A). In a 200 μL PCR tube, 50 μL of the mixture of ALuc16 and a metal cation (Ca(II), Fe(III), Ni(II), Zn(II), Mg(II), or Cr(VI); concentration: 100 μg/mL) in the metal-cation-free Tris-HCl buffer (Solution A) was further mixed with 10 μL of an nCTZ solution (Solution B). The tube was immediately moved into the chamber of a precision spectrophotometer (AB-1850, ATTO) (FIG. 6(B)), and the consequent spectra were taken in an integration of 30 seconds.

Figure 7:
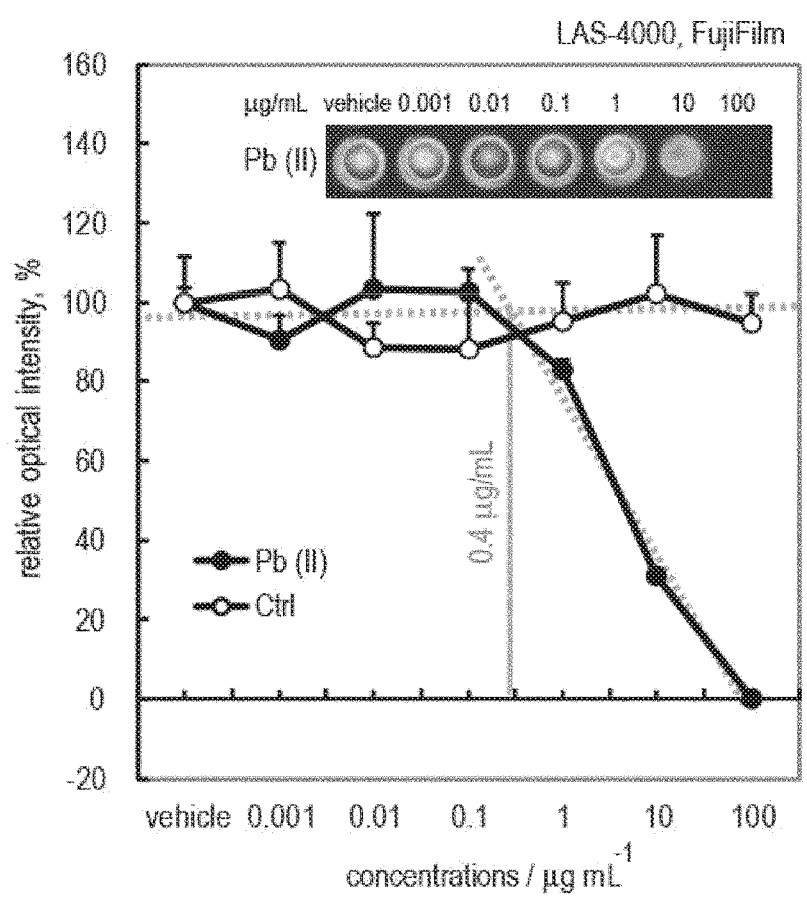
FIG. 7 is a graph for showing dose-response curves of ALuc16 activities with Pb(II) or a substrate alone (Ctrl). The ALuc16 activities are inhibited by raising concentrations of Pb(II). In the inset, an optical image taken with LAS-4000 (FujiFilm) is shown. A detection limit is found at around 0.4 μg/mL.

Detailed dose-response curves of ALuc activities were determined with varying concentrations of Pb(II) or a substrate alone for a negative control (FIG. 7). The experiment was conducted by the same method as that of FIG. 6. In the inset, the optical image taken with LAS-4000 (FujiFilm) is shown.

Reagents

The standard metal cations in FIG. 6 were purchased from Wako Pure Chemical Industries. The counter anion is chloride. The pcDNA3.1(+) plasmids encoding ALuc16, 23, 25, 30, and 34 were from the inventor's previous research (Non Patent Literatures 4 and 7). The plasmids encoding *Renilla reinformis* luciferase 8.6-535 (RLuc8.6-535) and *Gaussia princepes* luciferase (GLuc) were custom-synthesized by Eurofins Genomics and subcloned into the pcDNA3.1(+) vector (Invitrogen). A lipofection reagent (TransIT-LT1) was purchased from Mirus. The native coelenterazine (nCTZ) was obtained from the commercial RLuc assay kit (E2820, Promega) (Nishihara, R., et al., Bioluminescent coelenterazine derivatives with imidazopyrazinone C-6 extended substitution. Chem. Commun., 2014. 51: p. 391-394.). The ingredients for the universal buffer (citric acid, boric acid, $KH_2PO_4$) were obtained from Wako Pure Chemical Industries, and the Trizma base salt was purchased from Sigma-Aldrich and used for preparing a metal cation-free Tris-HCl buffer. Possible metal cation contamination in the inventor's reagents was simply estimated with inductively coupled plasma-mass spectrometry (ICP-MS) beforehand, and the results found that the concentrations of cations were all less than 1 μg/mL, and the concentrations of multivalent metal cations were less than 0.1 μg/mL (Table 2).

TABLE 2

| | | Li | | | Be | | | B | | |
|---|---|---|---|---|---|---|---|---|---|---|
| Result (ppb) | Blank | N.D. | ± | | N.D. | ± | | N.D. | ± | | |
| | TRIS | N.D. | ± | | N.D. | ± | | 21.4 | ± | 0.059 | 0.3% |
| | TRIS (adjusted) | N.D. | ± | | N.D. | ± | | 21.4 | ± | | |

| | | Al | | | K (key reference) | | | Ca | | |
|---|---|---|---|---|---|---|---|---|---|---|
| Result (ppb) | Blank | 1.66 | ± | 0.177 10.7% | N.D. | ± | | N.D. | ± | | |
| | TRIS | 5.35 | ± | 0.072 1.4% | 910 | ± | 46.0 5.1% | 6.80 | ± | 1.19 | 17.6% |
| | TRIS (adjusted) | 3.70 | ± | | 910 | ± | | 6.80 | ± | | |

| | | Cr | | | Mn | | | Fe | | |
|---|---|---|---|---|---|---|---|---|---|---|
| Result (ppb) | Blank | 0.006 | ± | 0.002 33.2% | 0.017 | ± | 0.006 37.2% | 0.611 | ± | 0.130 | 21.2% |
| | TRIS | 0.048 | ± | 0.007 14.7% | 0.341 | ± | 0.019 5.5% | 3.58 | ± | 0.023 | 0.6% |
| | TRIS (adjusted) | 0.041 | ± | | 0.325 | ± | | 2.97 | ± | | |

| | | Cu | | | Zn | | | Ga | | |
|---|---|---|---|---|---|---|---|---|---|---|
| Result (ppb) | Blank | 0.426 | ± | 0.051 11.9% | 3.38 | ± | 0.13 3.9% | 0.007 | ± | 0.001 | 18.4% |
| | TRIS | 0.518 | ± | 0.013 2.5% | 7.36 | ± | 0.11 1.5% | 0.287 | ± | 0.003 | 0.9% |
| | TRIS (adjusted) | 0.092 | ± | | 3.98 | ± | | 0.280 | ± | | |

TABLE 2-continued

| | | Rb | | | Sr | | | Mo | | |
|---|---|---|---|---|---|---|---|---|---|---|
| Result (ppb) | Blank | N.D. | ± | | 0.012 | ± 0.002 | 15.2% | N.D. | ± | |
| | TRIS | 0.077 | ± 0.007 | 9.3% | 0.577 | ± 0.001 | 0.2% | 0.042 | ± 0.0003 | 0.7% |
| | TRIS (adjusted) | 0.077 | ± | | 0.564 | ± | | 0.042 | ± | |

| | | In | | Sn | | | Sb | | |
|---|---|---|---|---|---|---|---|---|---|
| Result (ppb) | Blank | N.D. | ± | N.D. | ± | | N.D. | ± | |
| | TRIS | N.D. | ± | 0.110 | ± 0.001 | 1.1% | 0.039 | ± 0.0003 | 0.6% |
| | TRIS (adjusted) | N.D. | ± | 0.110 | ± | | 0.039 | ± | |

| | | Hg | | Tl | | Pb | | |
|---|---|---|---|---|---|---|---|---|
| Result (ppb) | Blank | N.D. | ± | N.D. | ± | 0.007 | ± 0.001 | 16.8% |
| | TRIS | N.D. | ± | N.D. | ± | 0.048 | ± 0.002 | 4.9% |
| | TRIS (adjusted) | N.D. | ± | N.D. | ± | 0.042 | ± | |

| | | U | | |
|---|---|---|---|---|
| Result (ppb) | Blank | N.D. | ± | |
| | TRIS | 0.001 | ± 0.0002 | 12.6% |
| | TRIS (adjusted) | 0.001 | ± | |

| | | Na | | | Mg | | |
|---|---|---|---|---|---|---|---|
| Result (ppb) | Blank | N.D. | ± | | 0.255 | ± 0.020 | 7.7% |
| | TRIS | 949 | ± 2.07 | 0.2% | 30.0 | ± 0.027 | 0.1% |
| | TRIS (adjusted) | 949 | ± | | 29.8 | ± | |

| | | Ti | | V | | |
|---|---|---|---|---|---|---|
| Result (ppb) | Blank | N.D. | ± | 0.009 | ± 0.001 | 9.7% |
| | TRIS | N.D. | | 0.040 | ± 0.001 | 3.6% |
| | TRIS (adjusted) | N.D. | | 0.031 | ± | |

| | | Co | | | Ni | | |
|---|---|---|---|---|---|---|---|
| Result (ppb) | Blank | N.D. | ± | | −0.093 | ± 0.004 | −4.5% |
| | TRIS | 0.005 | ± 0.001 | 21.4% | 2.20 | ± 0.053 | 2.4% |
| | TRIS (adjusted) | 0.005 | ± | | 2.29 | ± | |

| | | As | | Se | |
|---|---|---|---|---|---|
| Result (ppb) | Blank | N.D. | ± | N.D. | ± |
| | TRIS | N.D. | ± | N.D. | ± |
| | TRIS (adjusted) | N.D. | ± | N.D. | ± |

| | | Ag | | Cd | |
|---|---|---|---|---|---|
| Result (ppb) | Blank | N.D. | ± | N.D. | ± |
| | TRIS | N.D. | ± | N.D. | ± |
| | TRIS (adjusted) | N.D. | ± | N.D. | ± |

| | | Cs | | Ba | | |
|---|---|---|---|---|---|---|
| Result (ppb) | Blank | N.D. | ± | 0.001 | ± 0.003 | 450% |
| | TRIS | N.D. | ± | 0.767 | ± 0.007 | 0.9% |
| | TRIS (adjusted) | N.D. | ± | 0.766 | ± | |

| | | Bi | | | Th | | |
|---|---|---|---|---|---|---|---|
| Result (ppb) | Blank | 0.006 | ± 0.0004 | 5.9% | N.D. | ± | |
| | TRIS | 0.018 | ± 0.0003 | 1.5% | 0.003 | ± 0.0002 | 6.8% |
| | TRIS (adjusted) | 0.012 | ± | | 0.003 | ± | |

<Results and Discussion> Metal Cations Dominate Optical Intensities of ALucs

The metal cation-driven optical intensities of ALuc16 were examined (FIG. 6). Monovalent cations, such as Li$^+$, Na$^+$, K$^+$, and NH$_4$$^+$, had little effect on the optical intensities of ALuc16 (FIG. 5(B)). The same conclusion as the monovalent cation-driven feature was previously reported with OLuc (Non Patent Literature 9). In contrast, multivalent cations were found to greatly dominate the optical intensities of ALuc16 (FIG. 6). Ca(II) and Mg(II) among divalent cations elevate the ALuc16 activities up to 1.5 times, whereas the other divalent cations, such as Mg(II), Co(II), Cu(II), Zn(II), and Pb(II), suppress the ALuc16 activities in the metal cation-free Tris-HCl buffer (pH 8.2, 0.05 M) (Non Patent Literature 9, Inouye, S. and Y. Sahara, Identification of two catalytic domains in a luciferase secreted by the copepod *Gaussia princeps*. Biochem. Biophys. Res. Comm., 2008. 365(1): p. 96-101.). The corresponding repressive effects of Cu(II) and Zn(II) on OLuc and GLuc were previously reported. Among multivalent cations, Cr(VI) also boosted the optical intensities of ALuc16 about 2 times. The overall optical intensity ranking is listed as follows in descending order: Cr(VI), Mg(II), Ca(II)>Ni(II)>Mo(IV), Cd(II), Fe(III), Zn(II)>Mn(II) and the others (Co(II), Cu(II), and Pb(II)).

It has been determined that the optimal divalent radius of cations for binding to the EF-hand structures lies between the radii of Mg(II) (0.81 Å) and Ca(II) (1.06 Å) (Snyder, E. E., B. W. Buoscio, and J. J. Falke, Calcium(II) Site Specificity—Effect of Size and Charge on Metal-Ion Binding to an EF-Hand-Like Site. Biochemistry, 1990. 29(16): p. 3937-3943; Ozawa, T., K. Sasaki, and Y. Umezawa, Metal ion selectivity for formation of the calmodulin-metal-target peptide ternary complex studied by surface plasmon resonance spectroscopy. Biochimica Et Biophysica Acta-Protein Structure and Molecular Enzymology, 1999. 1434(2): p. 211-220.). The EF-hands and their mutants are known to have a broad cross-binding affinity with multivalent cations besides $Ca^{2+}$ (Rowe, L., M. Ensor, and S. Daunert, EF-hand $Ca^{2+}$-binding bioluminescent proteins: Effects of mutations and alternative divalent cations—art. no. 64490T. Genetically Engineered and Optical Probes for Biomedical Applications IV, 2007. 6449: p. T4490-T4490; Falke, J. J., et al., Quantitating and Engineering the Ion Specificity of an EF-Hand-Like $Ca^{2+}$ Binding-Site. Biochemistry, 1991. 30(35): p. 8690-8697; Gifford, J. L., M. P. Walsh, and H. J. Vogel, Structures and metal-ion-binding properties of the $Ca^{2+}$-binding helix-loop-helix EF-hand motifs. Biochemical Journal, 2007. 405: p. 199-221.). Considering the radius range, most of the tested metal cations potentially bind to the EF-hand structures. The present cation-driven feature of ALuc16 activities may be explained as follows: (i) the cations, Ca(II) and Mg(II), directly bind to the EF-hand-like structure of ALuc16 and modulate the optical intensities, (ii) the multivalent cations may stabilize the amide anion in the transition state of nCTZ, as a result of a reduced activation energy (Ea) in the enzymatic reaction, or (iii) the above-mentioned effects synergistically contribute to the elevation of the ALuc activities. The synergy effect is plausible with multivalent cations, considering the elevated optical intensities of ALuc16 by Cr(VI).

To date, the correlation between multivalent cations and luciferase activity has been poorly investigated. Few researches have dealt with this issue, and the working mechanism remains unclear. Rodionova et al. reported that Ca(II), Mn(II), and Mg(II) elevate the activities of *Fridericia* luciferase, which is from the Siberian luminous earthworm *Fridericia heliota* (Rodionova, N. S. and V. N. Petushkov, Effect of different salts and detergents on luciferin-luciferase luminescence of the enchytraeid *Fridericia heliota*. Journal of Photochemistry and Photobiology B-Biology, 2006. 83(2): p. 123-128.). However, the boosting effect with Mn(II) was not observed with the present ALuc16. A result with OLuc was previously reported by Inouye et al., who estimated the influence of several multivalent cations (Ca(II), Mg(II), Cu(II), Zn(II), and Cd(II)) on OLuc, where monovalent cations had little effect on the optical intensity of OLuc. In contrast, Cu(II), Zn(II), and Cd(II) inhibited the optical intensity.

The inhibitory effect of Pb(II) was further examined over a long concentration range (FIG. 7). The dose-response curves show that the ALuc16 activities are quickly inhibited by raising concentrations of Pb(II). The ALuc16 activities were not inhibited by the vehicle (Tris-HCl, pH 8.2) as a negative control. The linear range was between 1 μg/mL and 100 μg/mL. The optical intensity was quickly decreased, even by as low as 1 μg/mL of Pb(II) (FIG. 7). This result demonstrates that the column-purified ALuc is a novel optical sensor showing unique metal cation selectivity and sensitivity for multivalent metal cations.

Metal Cations have Little Effect on Bioluminescence Spectra

The inventors of the present invention further examined the contribution of metal cations on bioluminescence spectra. We examined the metal cation-driven variance of the bioluminescence spectra (FIG. 6(B)), where the effective metal cations shown in FIG. 6 were selected, i.e., Ca(II), Fe(III), Ni(II), Zn(II), Mg(II) or Cr(VI). However, in contrast to the inventor's speculation, almost no shift of the spectra was found with the metal cations. For example, Ca(II) and Ni(II) induced only 2 nm of blue shift and 4 nm of red shifts of the spectrum. The negligible effect of metal cations on the spectra suggests that the multivalent cations do not modulate the electric states of the intermediates of nCTZ in the chemical reaction of the light emission of ALucs.

Example 4

<Experiment>

The long-term stability of optical intensities was estimated by the same method as that of FIG. 6(A) (FIG. 8(A)). The microplate was placed in the chamber of LAS-4000, and the optical intensities were monitored every 5 minutes, after substrate injection, for a duration of 60 minutes.

Figure 8:
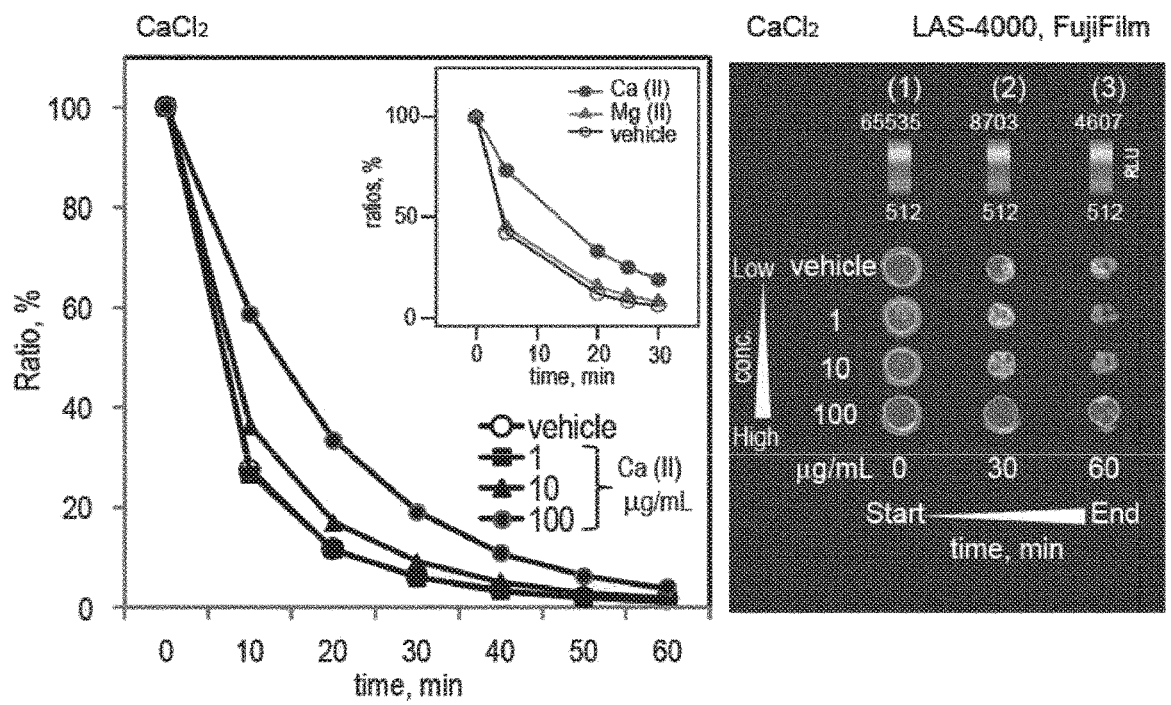
FIG. 8 are graphs for showing the cation-driven long-term stability of the optical intensities by ALuc16.
Figure 8:
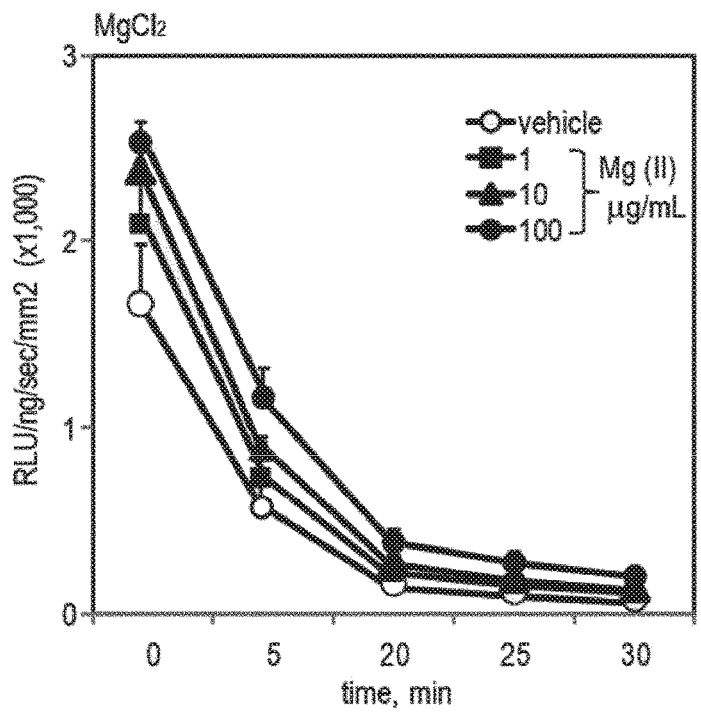

<Results and Discussion> Ca(II) Contributes to Long-Term Stability of ALuc Activities The long-term stability of luciferases is a key determinant for a bioluminescent marker in bioassays. Because of the boosting effect on ALuc activities, we chose Ca(II), Mg(II), and Cr(VI) for the cation-driven long-term stability (FIG. 8). A contrasting effect was found in a comparison of the effects of Ca(II) and Mg(II). Although both Ca(II) and Mg(II) boosted the optical intensities, only Ca(II) prolonged the bioluminescence intensities in a concentration-dependent manner (FIG. 8(A)). Ca(II) sustained 60% of the initial optical intensity for 13 minutes after nCTZ injection, and retained 4% of the optical intensity even after 60 minutes (FIG. 8(A), optical image). In contrast, the Mg(II) concentration dependently elevates the ALuc activities, but seldom influences the long-term stability (FIG. 8(A) and FIG. 9(B)).

The long-term stability suggests that Ca(II) modifies the structural robustness of ALuc16. We thus speculate that Ca(II) binds the EF-hand-like structure of ALuc16 and supports the prolonged optical intensities of ALucs.

Circular Dichroism (CD) Measurement of Metal Cation-Mixed ALuc16

Figure 9:
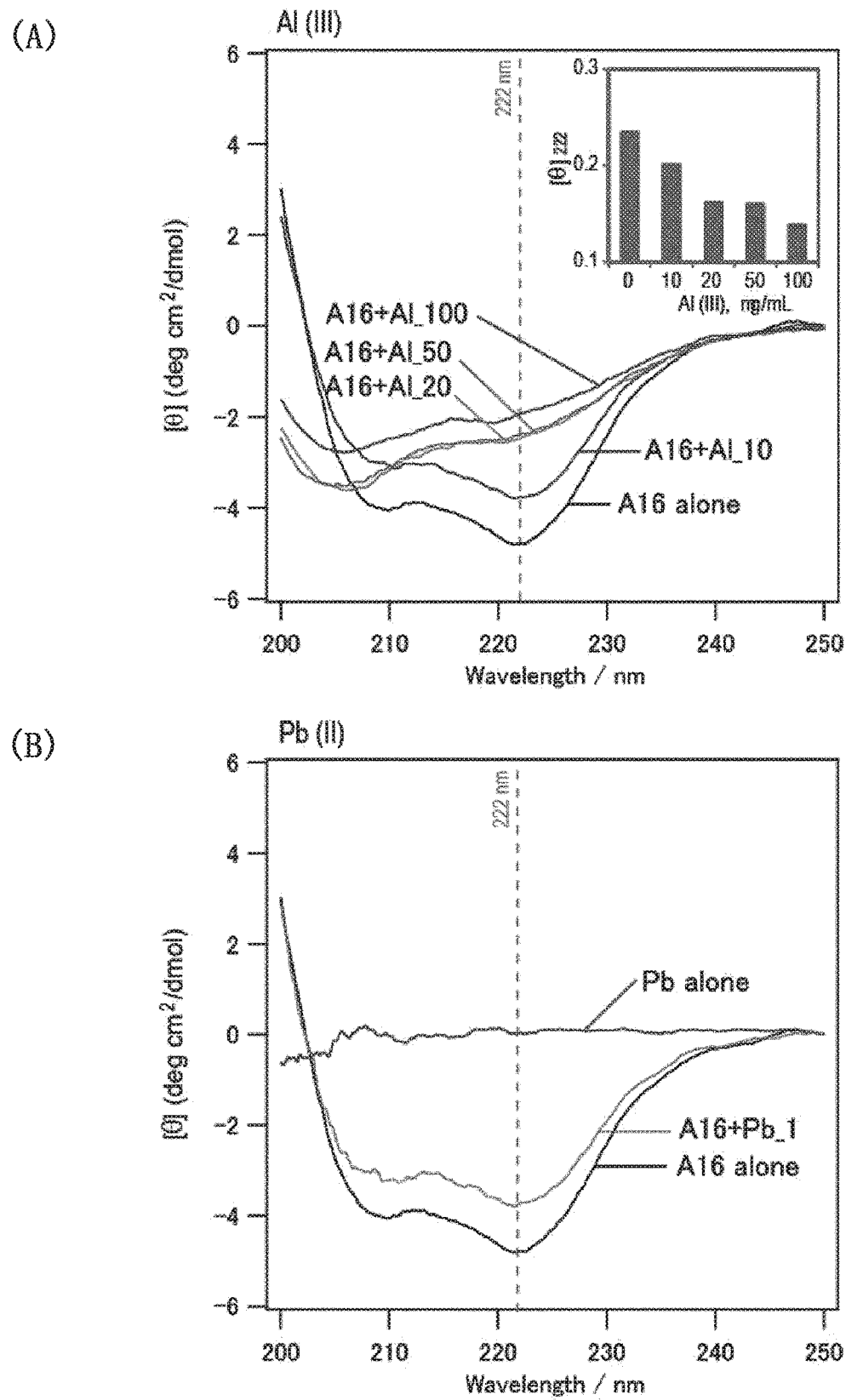
FIG. 9 are graphs for showing circular dichroism (CD) spectra for showing cation-ALuc structure correlations. In response to Pb(II) and Al(III), the structure of ALuc16 is denatured. Al_10, Al_20, Al_50, and Al_100 mean 10 μg/mL, 20 μg/mL, 50 μg/mL, and 100 μg/mL of Al(III), respectively. Pb 1 means 1 μg/mL of Pb(II).

Circular dichroism (CD) measurement was further conducted for reasoning the cation-driven degradation of ALuc16 activities (FIG. 9). Samples were prepared by mixing varying concentrations of Pb(II) or Al(III) with column-purified and dialyzed ALuc16, and were measured with a CD spectrometer (JASCO, Japan) after preparation.

The variation of the molar ellipticity in the CD spectra at 222 nm levels, that is, the α-helical portion is gradually decreased by elevating the Al(III) concentrations. The same feature was observed with Pb(II). Pb(II) levels higher than 1 μg/mL showed basal noise spectra. The overall results suggest that metal cations, such as Pb(II) and Al(III), destroy the tertiary structure of ALuc16, leading to decomposition.

(Example 5) Molecular Strain Sensor

Design of Plasmid

Figure 10:
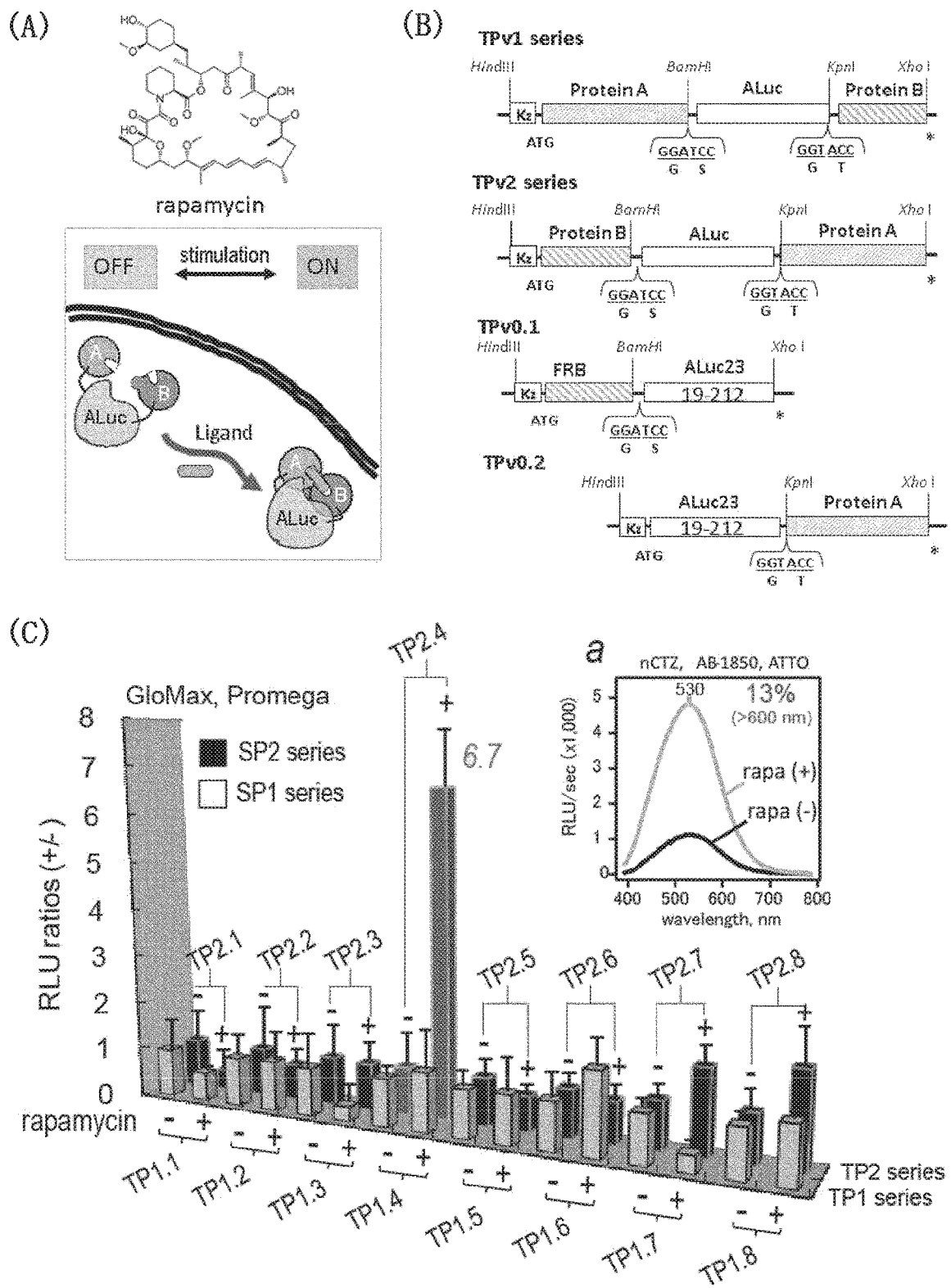
FIG. 10(A) is an illustration of the basic working mechanism of a molecular strain probe in a mammalian cell. Proteins A and B in the molecular strain probe approach each other in response to a ligand. The proteins are bound across ALuc due to a molecular strain. The molecular strain dramatically promotes bioluminescence.
FIG. 10(B) is a schematic diagram of cDNA constructs of bioluminescence template candidates each of which responds to a molecular strain. A difference between strain probes v1 and v2 is which of the proteins A and B is targeted. Abbreviations: TPv1 and v2 represent Tension Probe v1 and v2; and Kz represents a kozak sequence.
FIG. 10(C) is a graph for showing changes in optical intensities of 16 kinds of template candidates before and after ligand stimulation (n=3). Gray and black bars represent TPv1 and v2, respectively. Signs "+" and "−" in the X-axis represent the presence and absence of rapamycin, respectively. A red bar represents dramatic elevation of bioluminescence in a molecular strain probe named "TPv2.4". In inset a, bioluminescence spectra of TPv2.4 before and after rapamycin stimulation are shown. The highest optical intensity was found at 530 nm. Abbreviations: TPv1.1 represents Tension Probe Version 1.1, and TPv2.1 represents Tension probe version 2.1.
Figure 11:
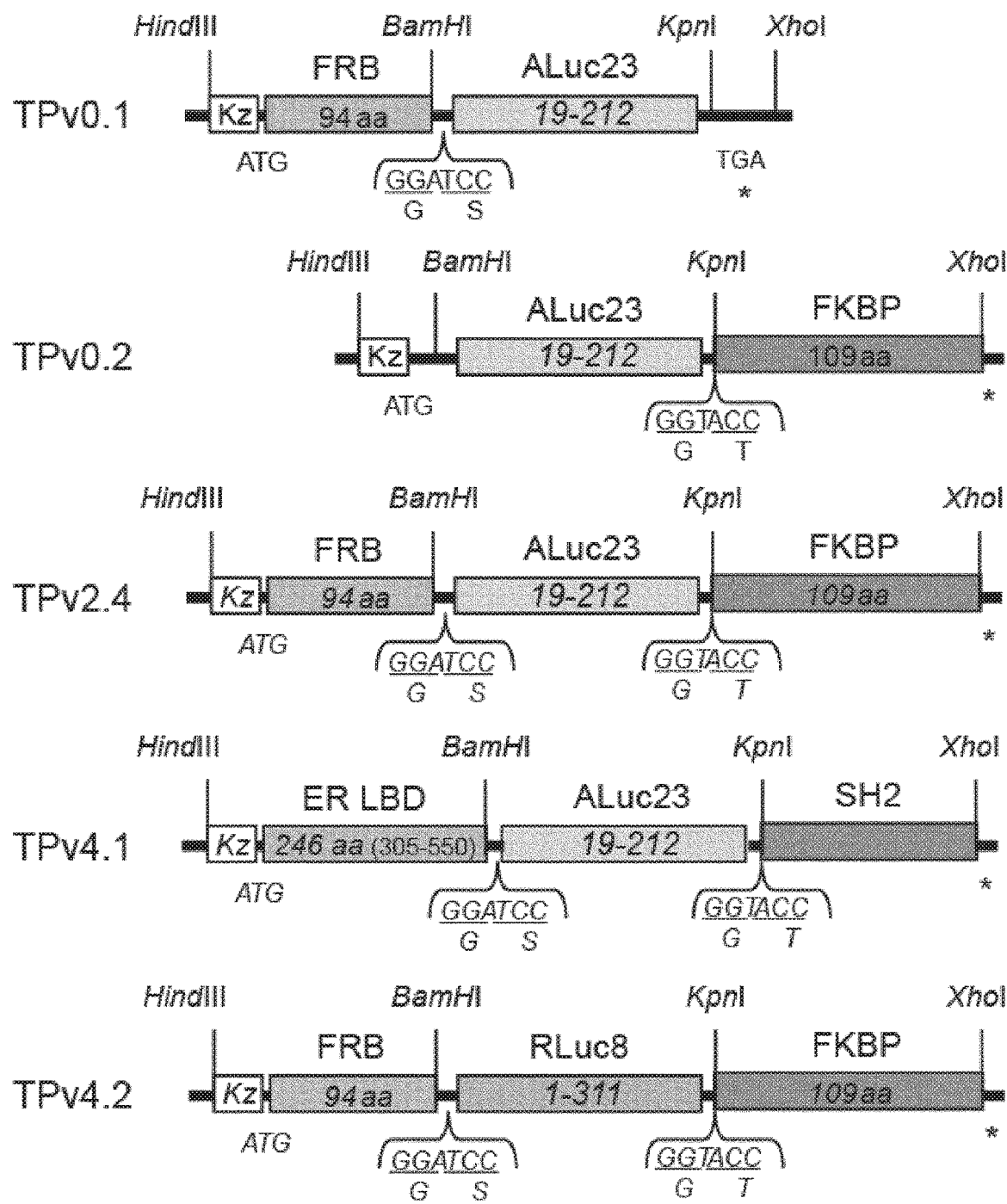
FIG. 11 is a schematic diagram of cDNA constructs encoding molecular strain probes. TPv0.1 and 0.2 are FKBP-deficient and FRB-deficient forms of TPv2.4, respectively. Abbreviations: Kz represents a kozak sequence, ER LBD represents the ligand binding domain of human estrogen receptor (205-555 aa), SH2 represents the SH2 domain of v-Src, and RLuc8 represents an 8-mutation-bearing variant of Renilla luciferase (RLuc).

The inventors of the present invention generated a series of DNA constructs encoding 23 kinds of different molecules designed for estimating their potential as molecular strain sensors able to sense PPIs (Table 3). The basic molecular constructs of TPv1 and TPv2 series probes differ in the consecutive order of their protein components from the N-terminus. Schematic diagrams of the cDNA constructs are illustrated in FIG. 10(B) and FIG. 11.

As templates for polymerase chain reaction (PCR), cDNAs encoding the following components were obtained from the corresponding providers: *Renilla* luciferase 8 (RLuc8) was kindly presented by Prof. Gambhir; ALucs16, 23, 24, and 30 were from the inventor's previous studies (Non Patent Literatures 4 and 7); the human FKBP (12 kD, GenBank accession number: AAP36774.1) and FRB (11 kD, PDB access number: 1AUE_A) were custom-synthesized by Europins Genomics (Tokyo) on the basis of the sequence information on a public database (NCBI); and the ligand binding domain of human estrogen receptor (ER LBD, 305-550 AA) and the SH2 domain of v-Src were from the inventor's previous research (Non Patent Literature 11).

TABLE 3

| Probe name | Protein A[†] | Inserted luciferase | Length of Luciferase[‡] | Internal Secretion peptide (SP)[*] | Protein B[†] |
|---|---|---|---|---|---|
| TPv0.1 | FKBP | ALuc23 | 19-212 | − | |
| TPv0.2 | | ALuc23 | 19-212 | − | FKBP |
| TPv1.1 | FKBP | ALuc16 | 1-212 (full) | + | FRB |
| TPv1.2 | FKBP | ALuc16 | 19-212 | − | FRB |
| TPv1.3 | FKBP | ALuc23 | 1-212 (full) | + | FRB |
| TPv1.4 | FKBP | ALuc23 | 19-212 | − | FRB |
| TPv1.5 | FKBP | ALuc24 | 1-212 (full) | + | FRB |
| TPv1.6 | FKBP | ALuc24 | 19-212 | − | FRB |
| TPv1.7 | FKBP | ALuc30 | 1-212 (full) | + | FRB |
| TPv1.8 | FKBP | ALuc30 | 19-212 | − | FRB |
| TPv2.1 | FRB | ALuc16 | 1-212 (full) | + | FKBP |
| TPv2.2 | FRB | ALuc16 | 19-212 | − | FKBP |
| TPv2.3 | FRB | ALuc23 | 1-212 (full) | + | FKBP |
| TPv2.4 | FRB | ALuc23 | 19-212 | − | FKBP |
| TPv2.5 | FRB | ALuc24 | 1-212 (full) | + | FKBP |
| TPv2.6 | FRB | ALuc24 | 19-212 | − | FKBP |
| TPv2.7 | FRB | ALuc30 | 1-212 (full) | + | FKBP |
| TPv2.8 | FRB | ALuc30 | 19-212 | − | FKBP |
| TPv3.1 | FRB | ALuc23 | 19-209 | − | FKBP |
| TPv3.2 | FRB | ALuc23 | 19-207 | − | FKBP |
| TPv3.3 | FRB | ALuc23 | 19-198 | − | FKBP |
| TPv4.1 | ER LBD | ALuc23 | 19-212 | − | SH2 |
| TPv4.2 | FRB | RLuc8 | 1-311 | − | FKBP |

[†]Proteins A and B refer to the proteins at the N- and C-terminal ends of the tension probe.
[‡]"Length of Luciferase" indicates the amino acid numbers of the inserted luciferase.
[*]The signs "+" and "−" represent the presence or absence of secretion peptide (SP).
Abbreviations:
ER LBD, the ligand-binding domain of estrogen receptor;
SH2, the SH2 domain.

A group of cDNA fragments encoding the components shown in Table 3 were generated by PCR using corresponding primers in order to introduce specific restriction sites. The specific restriction sites are HindIII/BamHI, BamHI/KpnI, or KpnI/XhoI at the 5'-terminus and 3'-terminus, respectively. A linker to be connected to the probe components was minimized in order to efficiently develop an intramolecular strain (intramolecular tension) in the probes. cDNA fragments were cleaved with corresponding restriction enzymes (NEB), ligated with a ligation kit (Takara Bio), and finally, subcloned into a pcDNA3.1(+) mammalian expression vector (Invitrogen) using HindIII and XhoI sites. The probes were divided into five groups (TPv0, TPv1, TPv2, TPv3, and TPv4 groups) on the basis of their molecular designs (Table 3).

The cDNA constructs encoding TPv1 and TPv2 series probes differ in the order of fragments from the 5'-terminus (FIG. 10(B)). The constructs encoding the TPv3 series probes are characterized by having a cDNA segment encoding ALuc23 at the shortened C-terminus as compared to other probes. The constructs encoding the TPv4 series probes were designed in order to investigate generally used existing probe designs and other PPI models, whereas the constructs encoding the TPv0 series probes were designed in order to confirm a negative control.

The DNA sequences of all the constructs were confirmed with a DNA sequence sequencer (GenomeLab GeXP, Beckman Coulter).

Evaluation of Optimal Molecular Design for Molecular TPs

Sixteen kinds of molecular designs were examined for designing efficient molecular TPs (FIG. 10(C)).

African green monkey kidney-derived COS-7 cells were cultured in a 96-well plate (Nunc) using a Dulbecco's modified Eagle's medium (DMEM) containing 10% fetal bovine serum (FBS; Gibco) and 1% penicillin/streptomycin in a cell incubator (5% $CO_2$; Sanyo) at 37° C. The cells on the plate were transiently transfected with a solution (0.2 μg/well) of pcDNA3.1(+) serving as one of the vectors encoding the TPv1 and TPv2 series probes and a lipofection reagent (TransIT-LT1; Mirus) as specified in FIG. 10(C), and were cultured under the condition of 5% $CO_2$ at 37° C. for 16 hours before proceeding to a subsequent experiment.

The cells on the plate were stimulated with a control (0.1% ethanol dissolved in the culture medium) or $10^{-6}$ M rapamycin for 4 hours, and then lysed with a lysis reagent (Promega). An aliquot (10 μL) of the lysate was transferred to a fresh 96-well optical bottom plate (Thermo Scientific), and simultaneously mixed with 10 μL of an assay solution (Promega) containing native coelenterazine (nCTZ) with a multichannel pipette (Gilson). The plate was immediately placed into the chamber of an image analyzer (LAS-4000; FujiFilm) equipped with a cooled CCD camera (−25° C.). The optical intensities were measured with image acquisition software (Image Reader V2.0) and analyzed with the specific image analysis software (Multi Gauge v3.1).

The luminescence intensities are expressed as fold luminescence intensities of relative luminescence intensities (RLU), i.e., RLU ratios (+/−). RLU(+) and RLU(−) represent the luminescence intensities with 1 μg of a cell lysate after the cells were cultured with and without rapamycin, respectively; the RLU is an amplified value of photon counts generated from the image analyzer.

Relative optical spectra were measured in the presence or absence of rapamycin (FIG. 10C, inset a). COS-7 cells expressing TPv2.4 were stimulated with $10^{-5}$ M rapamycin for 4 hours, and lysed with the lysis reagent. 5 μL of the lysate was mixed with 35 μL of the assay reagent (Promega) containing nCTZ in a 200 μL microtube. The relative optical spectra were integrated for 30 seconds with a high-precision spectrophotometer (AB-1850; ATTO) equipped with a cooled charge-coupled device (CCD) camera that enables one-shot capture of the entire light.

Fluorescence Under Molecular Strain by Protein-Protein Interactions (PPIs) Enhances their Optical Intensities A series of bioluminescent probes were designed for visualizing a luminescent molecular strain induced by intermolecular PPIs (FIG. 10(C)).

Some of the 16 designed probe candidates showed significantly enhanced or reduced optical intensities in response to rapamycin: TPv11.3 and TPv1.7 showed optical intensities reduced to one-third in response to $10^{-6}$ M rapamycin, whereas TPv2 exhibited a 6.7-fold enhanced bioluminescence intensity in the presence of $10^{-6}$ M rapamycin compared to the presence of a vehicle (culture medium containing 1% ethanol) alone. TPv2.7 and TPv2.8 resulted in approximately 2-fold stronger bioluminescence upon stimulation with the same ligand.

The relative optical intensities were obtained with COS-7 cells carrying TPv2.4, which were stimulated by the vehicle (0.1% ethanol) or $10^{-6}$ M rapamycin. The optical intensity in the spectra was greatly enhanced by rapamycin, and the maximum optical intensity ($\lambda_{max}$) was found at about 530 nm. About 13% of the overall light emission was located in the red and near-infrared region at a wavelength longer than 600 nm, which is highly tissue-permeable and commonly referred to as "optical window" (FIG. 10(C), inset a).

Secretion Protein (SP)-Embedding and -Deficient Probes Show Typical Ligand Sensitivity It has been previously predicted that copepod luciferases consist of a highly variable region that is an N-terminal region and its neighboring two repeated mirror image-like catalytic domains according to multiple alignment (Non Patent Literature 7 Inouye, S. and Y. Sahara, Identification of two catalytic domains in a luciferase secreted by the copepod *Gaussia princeps*. Biochem. Biophys. Res. Comm., 2008. 365(1): p. 96-101.). The highly variable domain constitutes a unique secretion protein (SP) at the N-terminus (Non Patent Literature 6).

It is interesting to compare the ligand sensitivities of SP-embedding and SP-deficient probes among the 16 molecular designs (FIG. 10(C)). (i) All of the molecular designs with SP failed to elevate the optical intensities, and (ii) a significant reduction of optical intensities was found only in the SP-embedding probes (TPv1.1, TPv1.3, TPv1.7, and TPv2.1).

The role of SPs in TPs is not clear yet. However, those results suggest that SPs act as natural flexible linkers inside the probes and, thus, may ease the intramolecular strain raised by the FKBP-FRB interaction. A corresponding view of the linker length, where a minimal length of the linkers was adapted between the probe domains to efficiently induce intramolecular strain to the sandwiched luciferase, was previously discussed (Kim, S. B., M. Sato, and H. Tao, Molecular Tension-Indexed Bioluminescent Probe for Determining Protein-Protein Interactions. Bioconjugate Chem., 2009. 20(12): p. 2324-2330).

All of the above-mentioned results show the following. (i) Luciferases may have the intrinsic nature to modulate their enzymatic activity in response to intramolecular strain induced by protein-protein interactions although the extent of optical variation may be trivial. (ii) The sensitivity of the probes to an intramolecular strain is dominated by the molecular designs including the flexible region of the luciferase, and the length of the flexible linkers.

Example 6

Ligand-Dependent Increase in Luminescence Intensity of TPv2.4

In order to investigate the ligand dependence of the luminescence intensity of TPv2.4, the luminescence intensity of TPv2.4 was measured with varying rapamycin concentrations (FIG. 12(A)). First, COS-7 cells expressing TPv2.4 were prepared in the following manner. First, cells were stimulated with a 0.1% aqueous ethanol solution (control) or rapamycin in the range of from $10^{-8}$ M to $10^{-4}$ M for 4 hours. After that, the cells were lysed with a lysis buffer (Promega), and an aliquot (10 μL) of the cell lysate was transferred to each well of a 96-well plate. An assay solution (50 uL) containing native coelenterazine was simultaneously added to the lysates on the microplate. The microplate was immediately moved into the black box of an image analyzer, and its luminescence intensity was measured. The resultant luminescence intensity (relative luminescence unit; RLU) was normalized with a protein amount (μg), an integration time (sec), and a luminescence area ($mm^2$). Accordingly, the unit is $RLU/\mu g/s/mm^2$.

Figure 12:
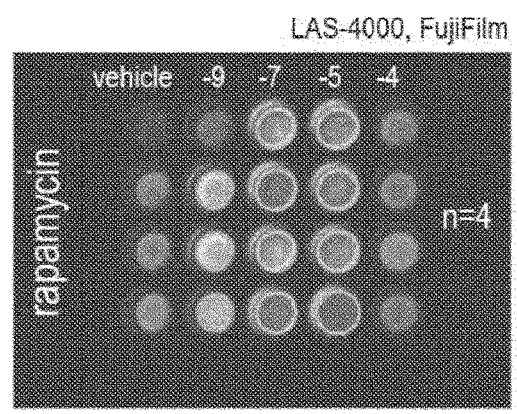
FIG. 12(A) is an image for showing changes in luminescence intensity of TPv2.4 dependent on changes in concentration of rapamycin (n=4). In inset a, luminescence intensities corrected with a protein amount (μg), a luminescence intensity integration time (sec), and a luminescence area (mm$^2$) are shown.
FIG. 12(B) is a graph for showing relative luminescence intensities of negative control probes (TPv0.1 and TPv0.2) and TPv2.4 before and after rapamycin stimulation (n=3). In inset a, molecular binding models of the molecular strain probes are illustrated. When stimulation is applied with $10^{-6}$ M rapamycin, a molecular strain is not applied to ALuc23 in the TPv0.1 or TPv0.2 probe. On the other hand, a strain is applied in the case of TPv2.4. When TPv0.1 and TPv0.2 are introduced into the same cells, intermolecular binding may occur therebetween. In inset b, their luminescence images are shown.
FIG. 12(C) is Western blot analysis for showing protein amounts of a PTv2.4 lysate. The lysate was electrophoresed, and blotted with an anti-FKBP antibody (abcam) and an anti-3-actin antibody (Sigma). Both showed luminescence intensities in the vicinity of 45 kD.
Figure 12:
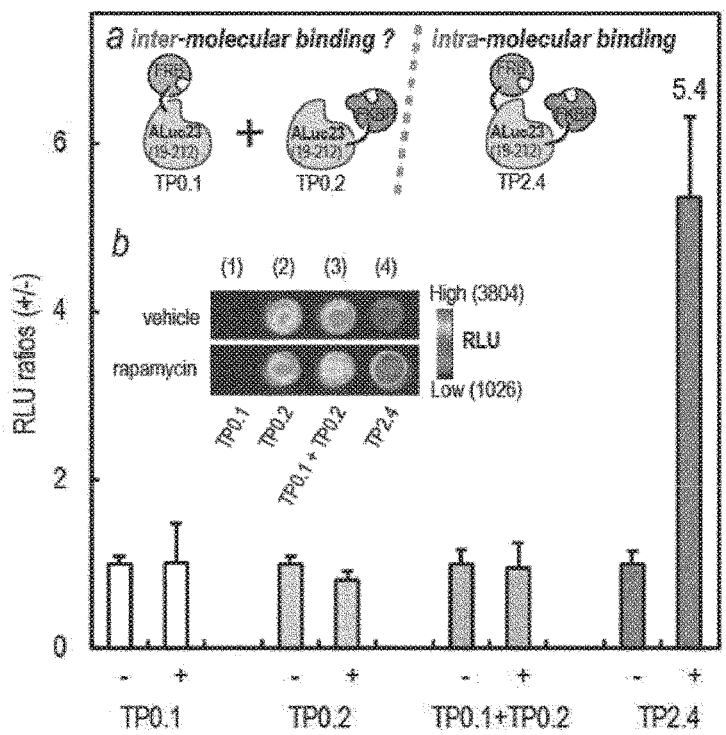
Figure 12:
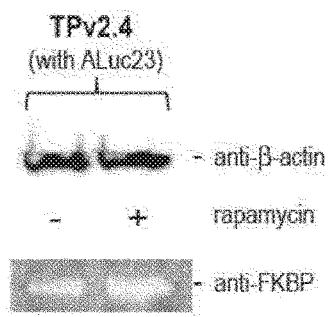

Luminescence Intensity of TPv2.4 Increased in Rapamycin-Quantitative/Dependent Manner The ligand dependence of the luminescence intensity of TPv2.4 was measured with varying rapamycin concentrations (FIG. 12). A background luminescence was shown with a 0.1% aqueous ethanol solution (control), whereas the luminescence intensity gradually increased with rapamycin stimulation and showed a maximal value at around $10^{-5}$ M. However, the luminescence intensity decreased to the background level to the contrary at a rapamycin concentration of $10^{-4}$ M. Such weak luminescence intensity was possibly due to the death of the cells caused by an excessive rapamycin concentration.

Negative Control for Demonstrating Molecular Strain—Luminescence Intensity Correlation of TPv2.4

The inventors of the present invention further investigated whether the luminescence intensity increased by rapamycin was a phenomenon caused by only the intramolecular strain of the molecular probe subjected to ligand stimulation. For example, it is possible that the phenomenon was caused by ligand-dependent intermolecular binding (FIG. 11 and FIG. 12(B)).

In order to perform an investigation eliminating the possibility that the phenomenon was caused by unpredicted intermolecular binding, the inventor fabricated TPv0.1 and TPv0.2. The probes have the structure of TP2.4 from which FKBP and FRB have been deleted, respectively. Constructs encoding such molecular probes were subcloned into pcDNA3.1(+), and the validity of the sequences thereof were verified with a DNA sequencer.

COS-7 cells were cultured in a 96-well microplate, and the cells in each well were transfected with the pcDNA3.1 (+) vector encoding (i) TPv0.1, (ii) TPv0.2, (iii) TPv0.1 plus TPv0.2, or (iv) TPv2.4. The cells were cultured in a $CO_2$ incubator for 16 hours, and then stimulated with rapamycin for 4 hours. The cells were lysed and an aliquot of the lysate (20 μL) was transferred to a 96-well microplate (plate for optical detection). Finally, an assay buffer (50 μL) containing a certain amount of native coelenterazine was simultaneously added to each lysate on the microplate, and each luminescence intensity was measured with an image analyzer.

In order to investigate the expression amount of TPv2.4, a Western blot experiment was performed (FIG. 12(C)). COS-7 cells were caused to transiently express TPv2.4, and then stimulated with $10^{-6}$ M rapamycin for 4 hours. After that, the cells were lysed with a certain amount of a sample buffer. The lysate was electrophoresed, and transferred onto nitrocellulose paper. After that, each protein was stained with a rabbit anti-FKBP antibody or a mouse anti-Q-actin antibody. After that, treatment with respective secondary antibodies was performed, and finally, luminescence was caused with a horseradish peroxidase (HRP) substrate solution (Immunostar, Wako).

Luminescence Intensities of TPv2.4 were Solely Enhanced by Interaction Between FRB and FKBP Bound by Ligand, and Intramolecular Strain Due to the Interaction The application of $10^{-6}$ M rapamycin stimulation to cells expressing (i) TPv0.1 alone, (ii) TPv0.2 alone, or (iii) both TPv0.1 and TPv0.2 failed to increase the luminescence intensities. Meanwhile, the same stimulation enhanced the luminescence intensities 5.4-fold in the case of cells expressing TPv2.4 (FIG. 12(B)).

An apparent expression level of TPv2.4 was investigated by Western blot analysis (FIG. 12(C)). As a result, an anti-FKBP antibody and an anti-β-actin antibody showed specific protein bands in the vicinity of 45 kD. The magnitudes of the molecular weights thereof agree with predicted molecular weights of TPv2.4 and β-actin. The densities of the bands before and after rapamycin stimulation did not significantly differ from each other.

The results of the negative control experiment show the following: (i) the interaction between FRB and FKBP induced by rapamycin induced a molecular strain, and was the only factor contributing to the enhancement of the luminescence intensity of the ALuc, (ii) the intermolecular protein-protein interaction did not enhance the luminescence intensity of the ALuc, (iii) $10^{-6}$ M rapamycin itself cannot enhance or inhibit ALuc activity, and (iv) according to the Western blot results, TPv2.4 is certainly expressed and its expression amount is not significantly biased by rapamycin stimulation.

Example 7

Development of Combinational Probe for Visualizing Protein-Protein Interaction

Figure 13:
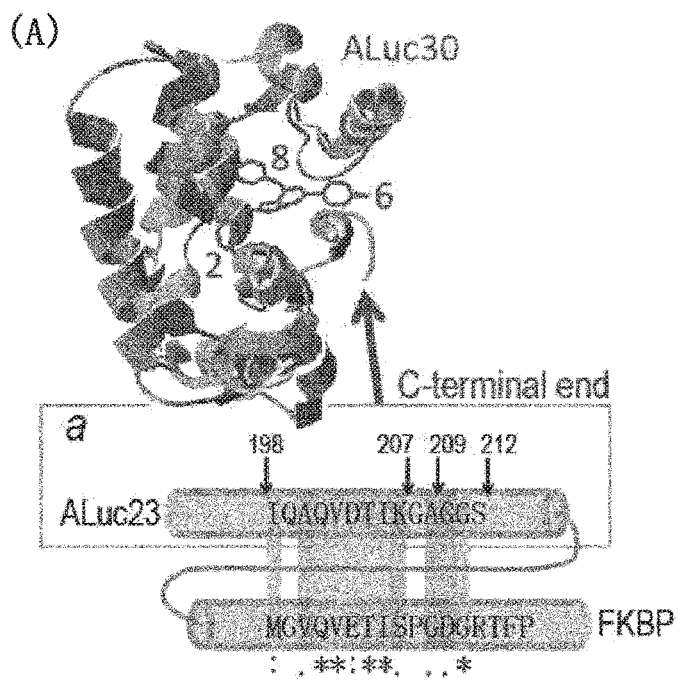
FIG. 13(A) is an illustration of supersecondary steric structure prediction of ALuc30 (SEQ ID NO: 34). In inset a, ALuc23 (SEQ ID NO: 32) is referenced, and the C-terminus of the ALuc is illustrated. The C-terminus of the ALuc (SEQ ID NO: 44) has a high homology with the N-terminal sequence of FKBP (SEQ ID NO: 45).
FIG. 13(B) is a graph for showing the luminescence intensities of the TPv3 series under the condition of the presence or absence of rapamycin (n=4). The TPv3 series templates share a feature in that the C-terminus of ALuc23 present between FRB and FKBP is short as compared to the TPv2 series. The white dotted box in the luminescence image indicates an extremely low background luminescence. Respective lengths are shown in parentheses. The asterisk indicates an extremely low background luminescence as compared to others. In inset a, their actual luminescence intensities are shown.
Figure 13:
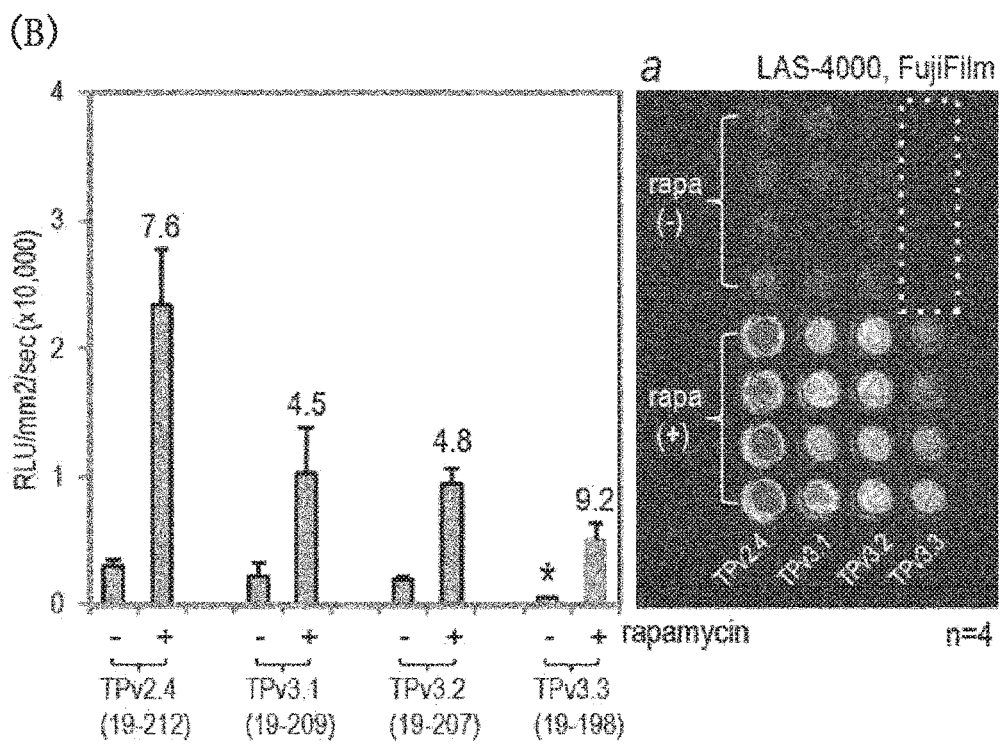
Figure 14:
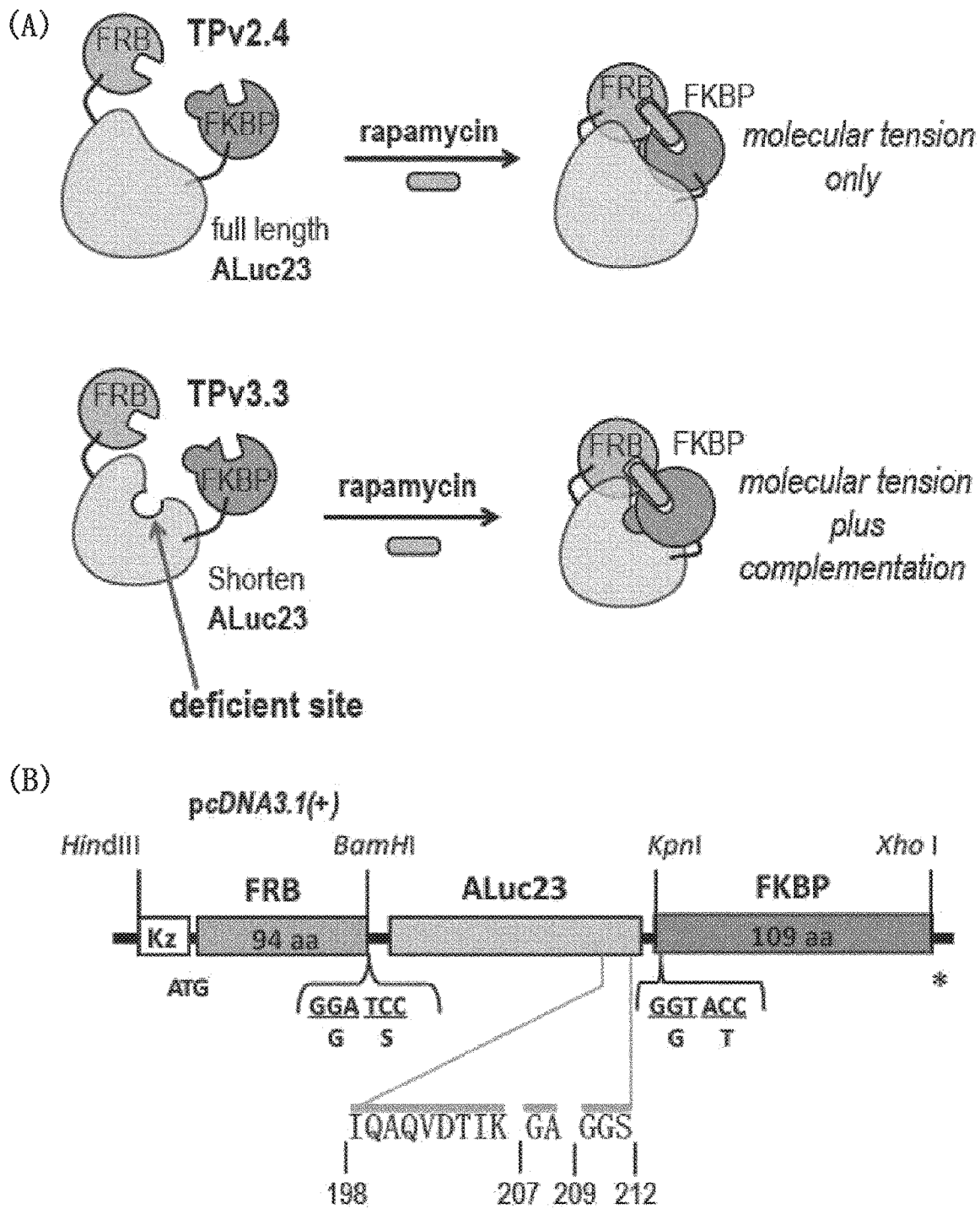
FIG. 14(A) is a schematic diagram for illustrating the working principles of combination bioluminescent probes. FRB-FKBP binding induces a strain therein on both upper and lower probes. The deficiency of the shortened ALuc23 (SEQ ID NO: 32) in the lower probe is complemented by the N-terminus of the neighboring FKBP (SEQ ID NO: 44).
FIG. 14(B) is a schematic diagram of a cDNA construct of a combination bioluminescent probe.

On the basis of the success of TPv2.4 described above, a combinational probe having the benefit of a molecular strain sensor in combination with the benefit of a protein fragment complementary assay was developed (FIG. 13 and FIG. 14).

The inventor of the present invention paid attention to the fact that, in TPv2.4, the C-terminal sequence of ALuc23 showed a high homology with the N-terminus of FRBP (FIG. 13(A), inset a). On the basis of this information, luminescent probes each having a form in which several amino acids in the amino acid sequence at the C-terminus of ALuc23 in TPv2.4 were deleted were developed, and were named TPv3.1, TPv3.2, and TPv3.3 (Table 3, FIG. 14(B)). This operation was obtained by an operation involving replacing the DNA of full-length ALuc23 with the DNA of ALuc23 having its 3'-terminus deleted.

COS-7 cells expressing any one of the above-mentioned TPv3 series probes (i.e., TPv2.4, TPv3.1, TPv3.2, and TPv3.3) were cultured in a 96-well transparent-bottom plate by the same method as that of the other experiments (FIG. 13(B)). The cells were stimulated with a control (0.1% ethanol) or $10^{-6}$ M rapamycin for 4 hours, and then a cell lysate was generated. A luminescence intensity emitted from the cell lysate was measured with the above-mentioned image analyzer.

Combinational probes showed improved signal-to-background (S/B) ratios: as described above, a series of combinational probes having the features of both a molecular strain sensor and a protein complementary assay were created (FIG. 13).

When amino acids at the C-terminus of ALuc23 were sequentially deleted, the probe luminescence intensity was also sequentially weakened (FIG. 13(B)). TPv3.3, which showed the maximal S/B ratio, was the one containing the shortest ALuc23 (18-198 AA). As can be seen, the improved S/B ratio was obtained by a significant reduction in background intensity rather than by the luminescence intensity enhanced by rapamycin. In actuality, the luminescence intensity of TPv3.3 obtained through control (0.1% ethanol) stimulation did not significantly differ from the background intensity (FIG. 13(B), inset a, dotted line). This result demonstrates that (1) first, a combinational probe having the benefit of a molecular strain sensor in combination with the benefit of a protein fragment complementary assay can be actually fabricated. In addition, (2) in consideration of general benefits of the molecular strain sensor and the protein complementary assay, it may be even possible for the combinational probe to obtain a stronger luminescence intensity and S/N ratio through a certain optimization process.

Example 8

Substrate Dependence of Luminescence Intensity and Time Course of TPv2.4

Figure 15:
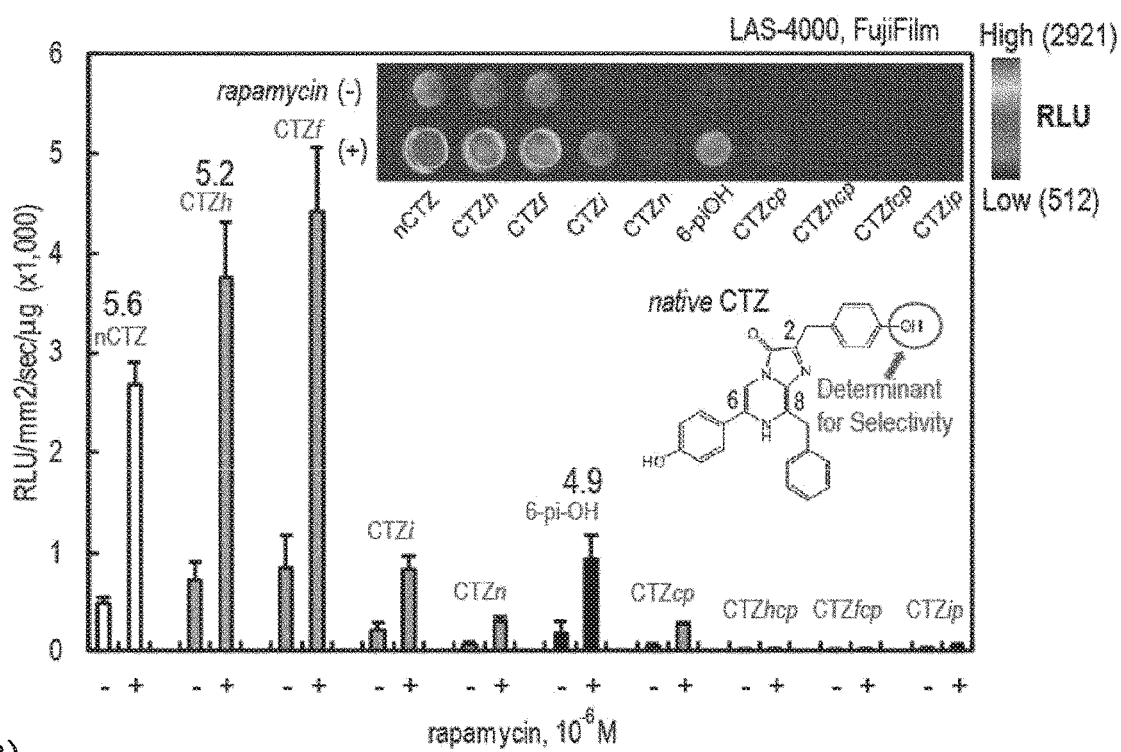
FIG. 15 are graphs for showing the substrate selectivity of a molecular strain sensor (TPv2.4).
Figure 15:
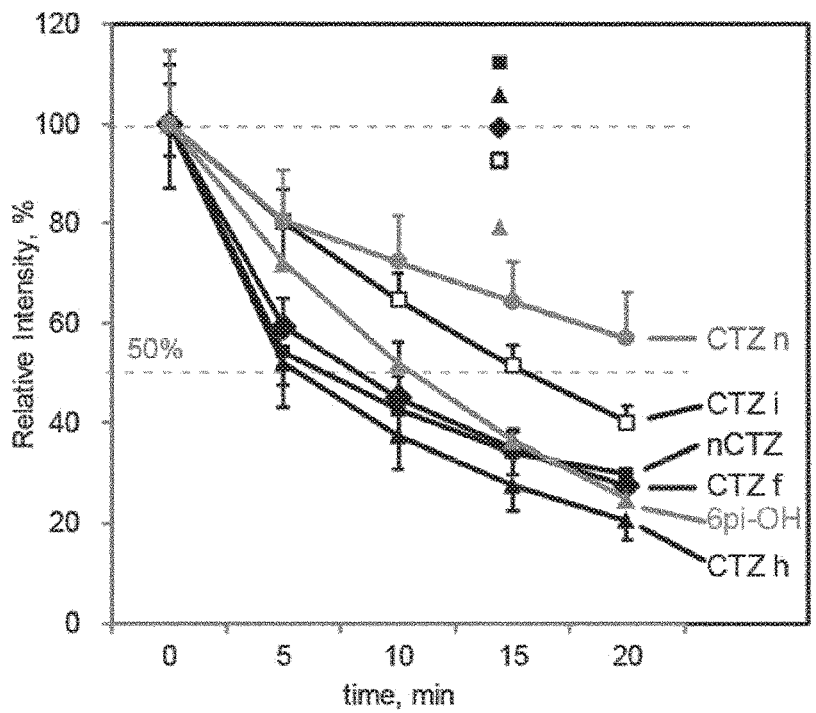

The substrate dependence of the luminescence intensity and time course of TPv2.4 was measured under the condition of the presence or absence of rapamycin (FIG. 15).

COS-7 cells were cultured in a 96-well plate, and the cells were transiently transfected with the pcDNA3.1(+) vector encoding TP2.4. After that, the cells were cultured for 2 days. After being stimulated with $10^{-6}$ M rapamycin for 4 hours, the cells in each well were lysed with a cell lysis buffer (50 µl) for 20 minutes. After that, an aliquot of the lysate (10 µL) was transferred to a 96-well transparent-bottom plate. Separately, about 10 kinds of coelenterazine analogs (substrates, 25 µg) were dissolved in 25 µL of ethanol. The solution was further 10-fold diluted with an assay buffer (Promega) to prepare a solution having a final concentration of 0.1 µg/µL. The solution was named substrate solution. 50 µL of the substrate solution was simultaneously introduced into the lysate solution on the plate using a multipipette, and the plate was immediately moved into an image analyzer (LAS-4000, FujiFilm), followed by optical measurement every 5 minutes in a 30-second integration time mode.

The coelenterazine analogs subjected to the measurement in this research were 9 kinds from "Coelenterazine Sampler Kit" of Promokine, i.e., native coelenterazine (nCTZ), coelenterazine h (CTZ h), coelenterazine f (CTZ f), coelenterazine i (CTZ i), coelenterazine n (CTZ n), coelenterazine cp (CTZ-cp), coelenterazine hcp (CTZ hcp), coelenterazine fcp (CTZ fcp), and coelenterazine ip (CTZ ip).

TPv2.4 Prefers nCTZ, CTZ h, and CTZ f for Strong Luminescence Intensity

The substrate selectivity and time course characteristics of TPv2.4 were studied with various coelenterazine analogs (FIG. 15).

The strongest bioluminescence intensities for TPv2.4 were observed in the cases of nCTZ, CTZ h, and CTZ f (FIG. 15(A)). For example, the absolute luminescence intensities thereof were 4- to 5-fold stronger as compared to the case of CTZ i. On the other hand, of the substrates, the CTZs hcp, fcp, and ip showed weak luminescence intensities, i.e., luminescence intensities close to the background intensities. A "chemical structure-luminescence intensity correlation" was studied for more precise analysis, and as a result, it was found that the luminescence intensity was dependent on the size of the side chain at the C-2 position of coelenterazine. That is, the size of the side chain at this position decreases in the order of CTZ n, CTZ i, CTZ f, and CTZ h, but the luminescence intensity increases in about the same order. The weak luminescence intensities of CTZ cp, CTZ hcp, CTZ fcp, and CTZ ip may be explained by the side chain at the C-8 position of coelenterazine. Similar results had also been obtained from the previous research conducted by the inventor of the present invention on the substrate dependence of an artificial bioluminescent enzyme (ALuc) (Non Patent Literature 7). Also in the previous research, the luminescence intensity increased in the order of CTZ n, CTZ i, CTZ f, and CTZ h.

Luminescence intensity sustainability longer than that of native coelenterazine was able to be observed in the case of using CTZ n or CTZ i (FIG. 15(B)). The luminescence half-life of CTZ i is about 15 minutes from substrate injection. Meanwhile, in the case of CTZ n, about 60% of the initial luminescence intensity was retained even 20 minutes after substrate injection.

The above-mentioned results shown by the molecular strain sensor (TP) may be analyzed as follows. (1) The luminescence intensity and stability of the substrate are basically dominated by the size effects of functional groups in side chains at the C-2, C-6, and C-8 positions. (2) The C-2 of the coelenterazine analog is the most important site for determining the luminescence intensity and sustainability. (3) The C-8 position of coelenterazine is conserved for the substrate to recognize the molecular strain sensor (TP), and any change at the C-8 position inhibits the recognition of the molecular strain sensor (TP) by the substrate.

Example 9

Living Cell Imaging of COS-7 Cells Carrying TPv2.4

Bioluminescence imaging of living COS-7 cells expressing TPv2.4 in a multichannel microslide (μ-slide VI$^{0.4}$, ibidi) was performed. First, COS-7 cells were cultured in a 6-channel microslide, and the cells were transiently transfected with the pcDNA3.1(+) vector encoding TPv2.4, and were cultured for 2 days. The left and right three channels of the cells were stimulated with a control (0.1% ethanol) and $10^{-6}$ M rapamycin, respectively, for 4 hours. After that, the culture medium in the slide was exchanged with an HBSS buffer containing a substrate (native coelenterazine). Immediately after that, the slide was moved into the chamber of an image analysis apparatus, and luminescence images were measured every 5 minutes in a 30-second integration mode.

Figure 16:
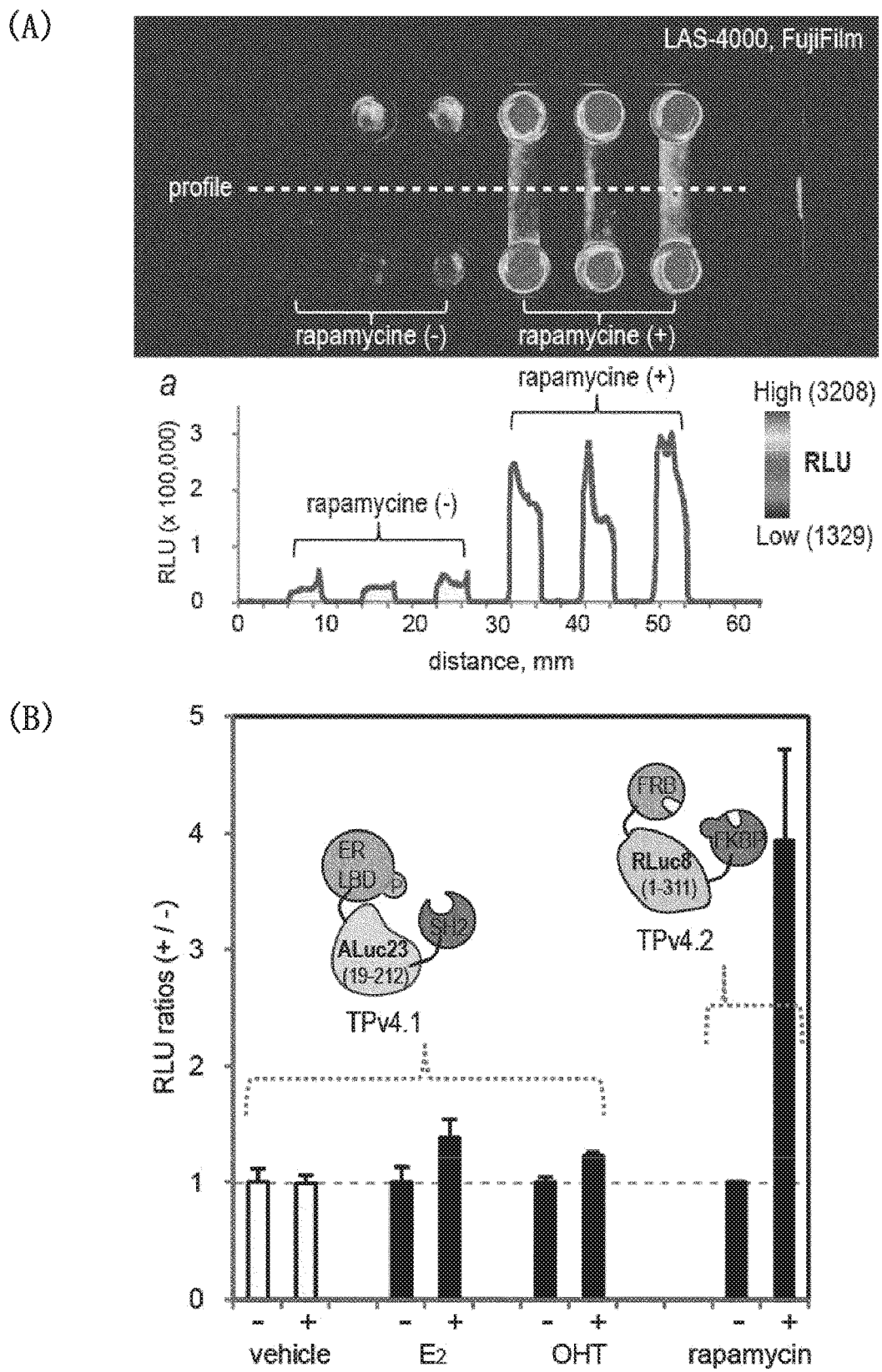
FIG. 16(A) is an image for showing the rapamycin-dependent luminescence intensity of living COS-7 cells on a microslide. TPv2.4 emits bioluminescence in a rapamycin-dependent manner. In inset a, the profile of the image of the optical slide is shown.
FIG. 16(B) is a graph for showing relative luminescence intensities of TPv4.1 and TPv4.2 for various ligands (n=3). In the insets, the molecular structures of TPv4.1 and TPv4.2 are illustrated. Abbreviations: ER LBD represents the ligand binding domain of human estrogen receptor, SH2 represents the Src homology domain of v-Src, RLuc8 represents an 8-mutation-bearing variant of Renilla luciferase, E2 represents 17β-estradiol, and OHT represents 4-hydroxytamoxifen.

Application to Other Protein-Protein Binding Models for Studying General Applicability of Concept of this Probe Through further modification of TPv2.4, whether the concept was generally applicable to other protein-protein binding models was tested (FIG. 16(B)).

The DNAs encoding FRB and FKBP in TPv2.4 were replaced with ER LBD and SH2 domain, respectively, and the resultant was named TPv4.1. The binding between the phosphorylated ER LBD and SH2 domain represents a typical nongenomic signaling mechanism of ER in mammalian cells. Separately, the cDNA of ALuc23 (18-212 AA) in TPv2.4 was replaced with cDNA of RLuc8, and the resultant was named TPv4.2 (Table 3, FIG. 11, and FIG. 16(B)). Bioluminescence intensities were measured by image analysis using nCTZ as the substrate in the above-mentioned manner.

TPv2.4 Induces Ligand-Dependent Bioluminescence Increase in Living Cells

Bioluminescence imaging in a small-animal model is an attractive theme in the fields of medicine and pharmacy. Biological applicability of this luminescent probe was tested using living COS-7 cells expressing TPv2.4 (FIG. 16(A)).

Only the right three channels stimulated with $10^{-6}$ M rapamycin exhibited about 6-fold stronger luminescence as compared to the left three channels stimulated with the control (0.1% ethanol). High S/B ratio results shown in this model research indicate that living mammalian cells expressing TPv2.4 can be implanted into a specific organ of living animals, where rapamycin activity can be confirmed on the basis of the bioluminescence intensity.

Basic Concept of Molecular Strain Sensors is Generally Applicable to Other Protein-Protein Binding Models The general applicability of the concept of the present molecular strain sensors was examined with the following protein-protein binding models (PPI): i.e., (i) TPv4.1 (ER LBD-ALuc23-SH2), in which 17β-estradiol ($E_2$) promotes binding between ER LBD and SH2; and (ii) TPv4.2 (FRB-RLuc8-FKBP), in which rapamycin promotes binding between FRB and FKBP.

Example 10

Figure 18A:
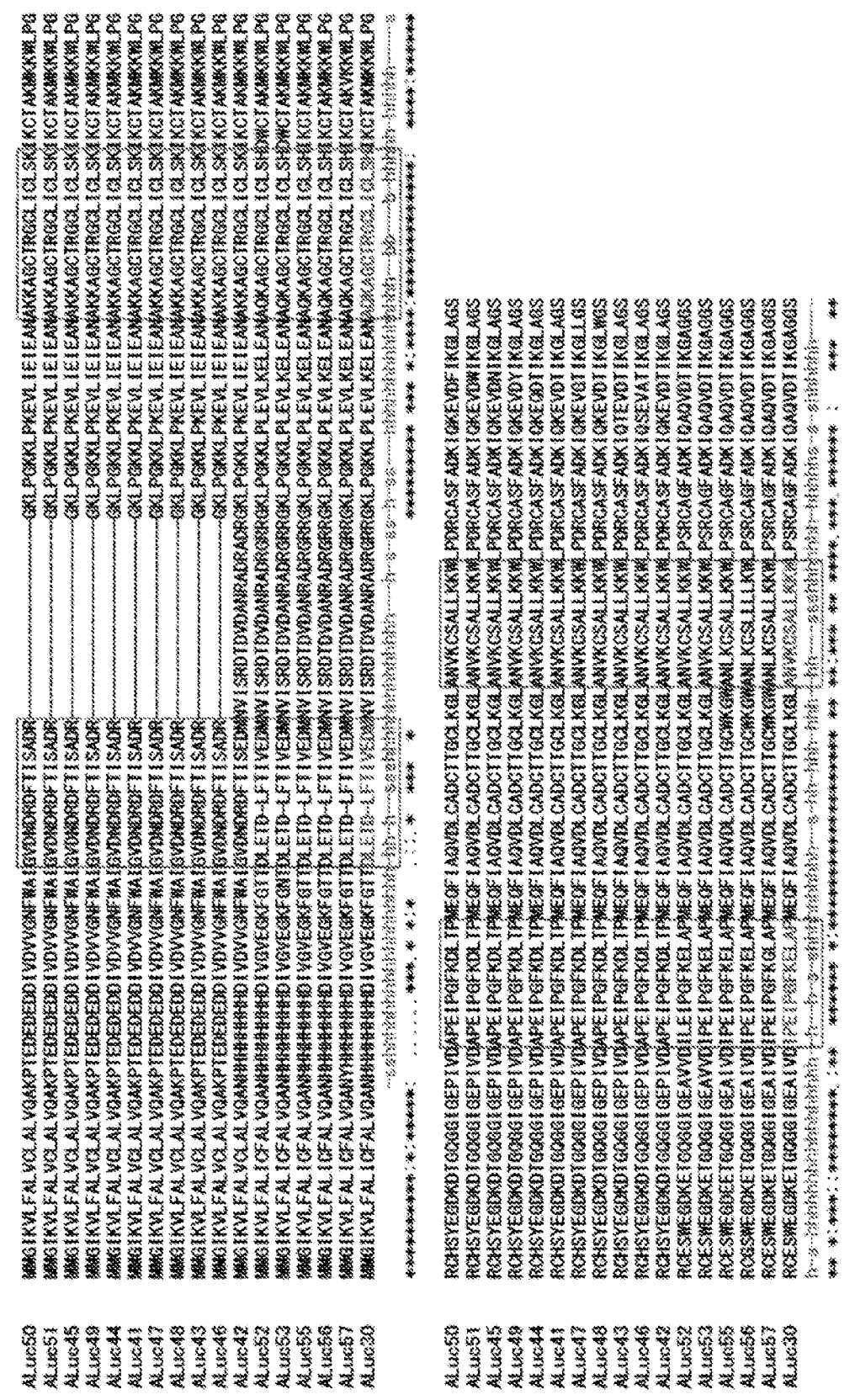
Figure 18B:
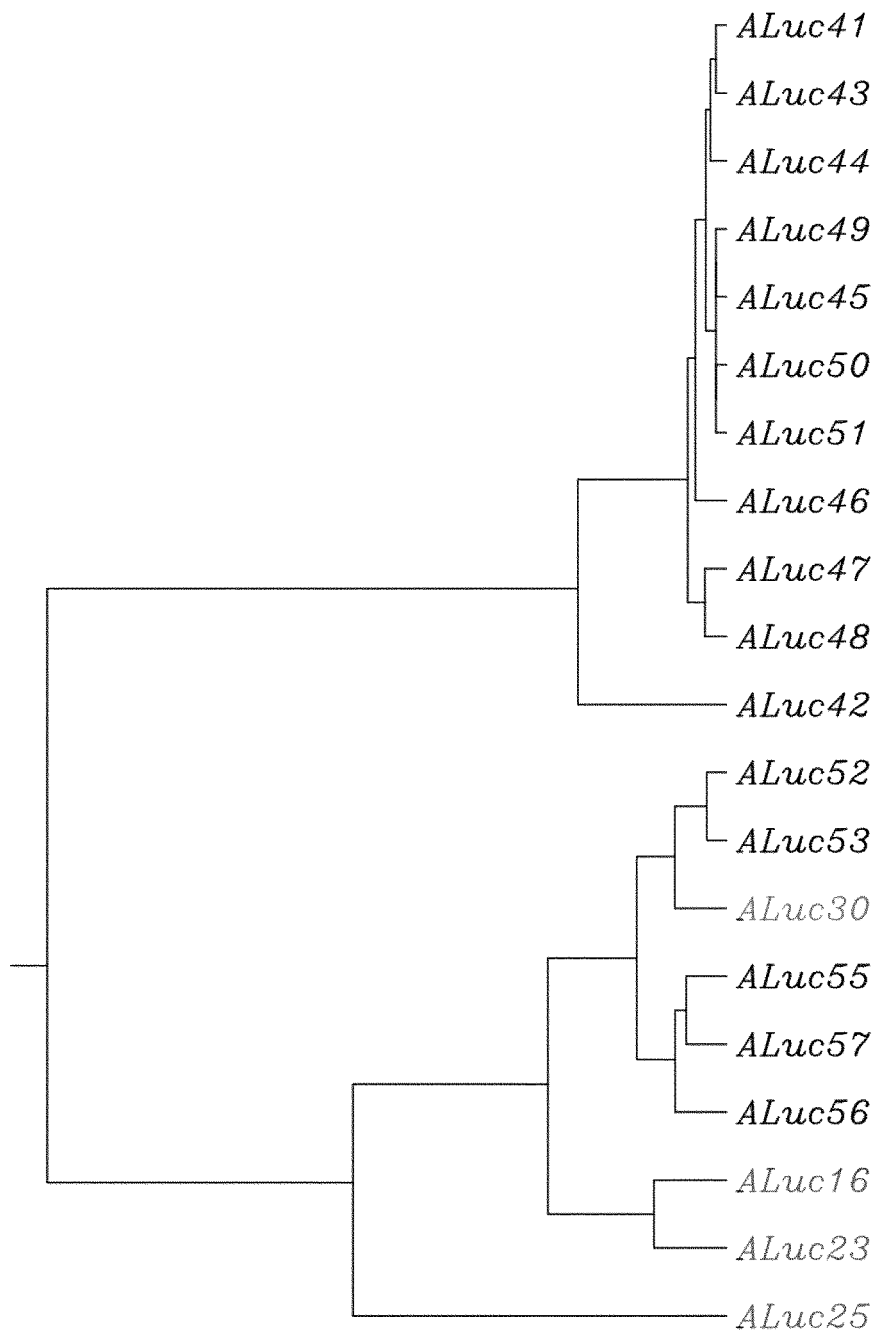
FIG. 18(B) is a relative genetic phylogram of newly synthesized artificial bioluminescent enzymes. On the basis of the sequences of the newly synthesized artificial bioluminescent enzymes, their mutual genetic correlation was investigated. A search was made with public software CLUSTAL 2.1.

Generation of Novel Artificial Bioluminescent Enzyme and Evaluation of Luminescence Activity Thereof In order to establish novel artificial bioluminescent enzymes, frequently occurring amino acids were extracted from the amino acid sequences of natural bioluminescent enzymes using known WebLogo Display software (weblogo.berkeley.edu/logo.cgi) (FIG. 17). As a result, enzymes capable of luminescence even when a partial sequence in the amino acid sequence was deleted were found. Frequently occurring amino acids were highlighted, and the sequences were connected together to develop luminescent enzymes of numbers from ALuc41 to ALuc51. In addition, on the basis of the backbones of existing ALucs, novel artificial bioluminescent enzymes (ALuc51-ALuc57) were developed with reference to the amino acid sequences of ALuc41. Their specific sequences are shown in FIG. 18(A). FIG. 18(B) is a relative genetic phylogram of the present newly synthesized artificial bioluminescent enzymes. The relative genetic phylogram was calculated with CLUSTALW 2.1.

Figure 19:
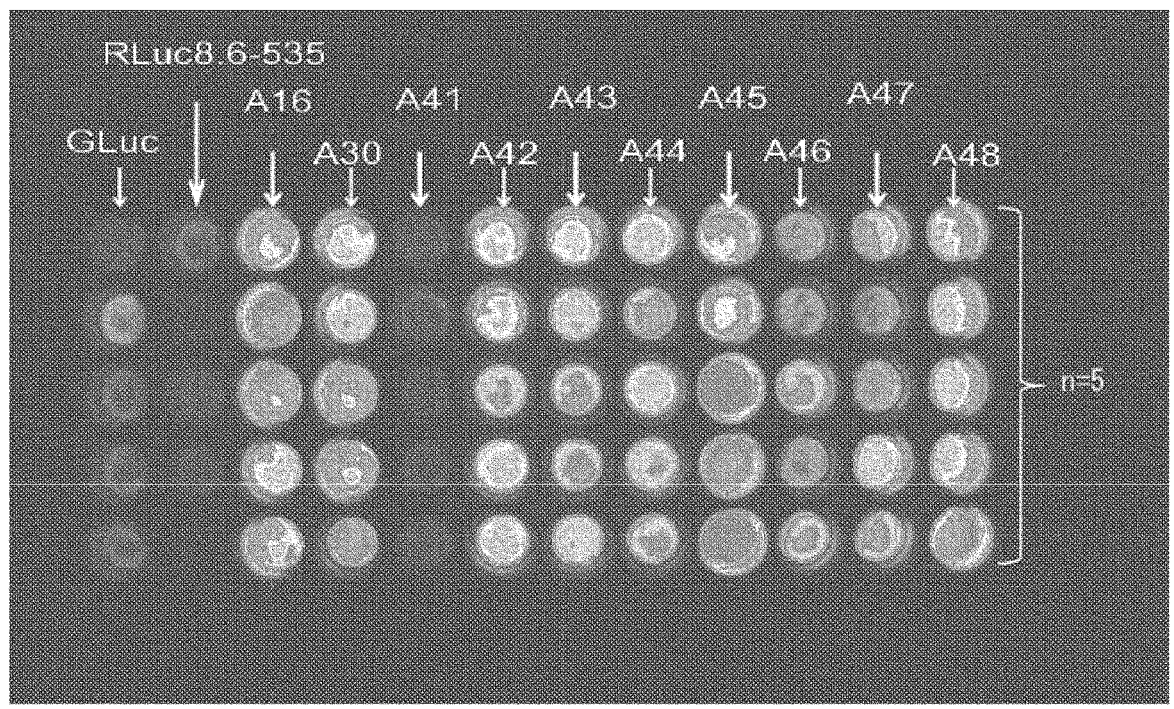
FIG. 19 is an image for showing relative luminescence intensities of novel artificial bioluminescent enzymes (GLuc, RLuc8.6-535, ALuc16, ALuc30, and ALuc41-48) (n=5).
Figure 20:
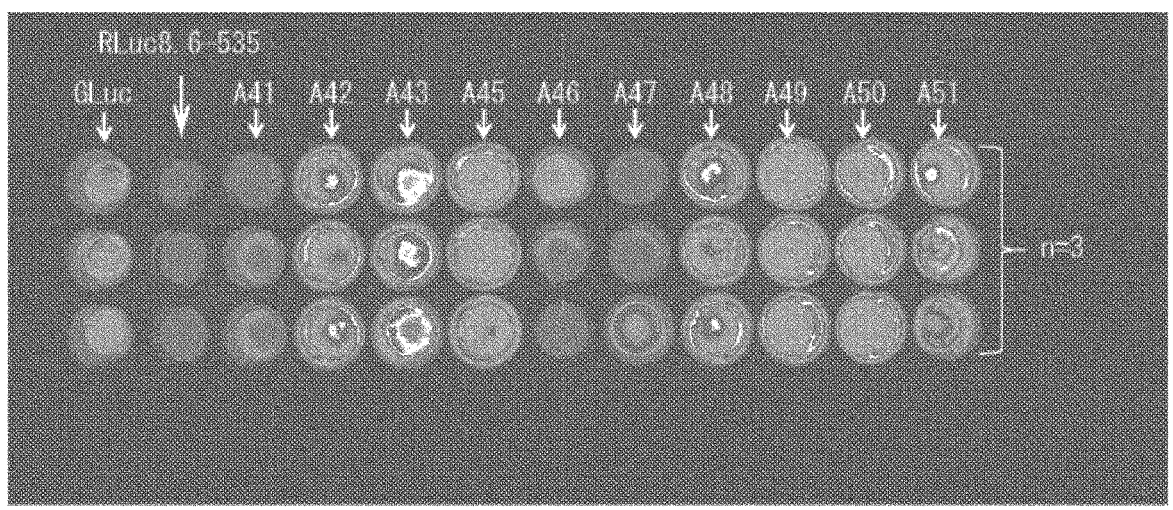
FIG. 20 is an image for showing relative luminescence intensities of novel artificial bioluminescent enzymes (GLuc, RLuc8.6-535, and ALuc41-51) (n=3).

African green monkey kidney-derived COS-7 cells were cultured using a 96-well microplate. The COS-7 cells were grown until occupying 90% of the bottom-surface area of the culture plate, and, as shown in FIG. 19 and FIG. 20, were each transiently transfected with a pcDNA 3.1(+) vector (Invitrogen) encoding each luminescent enzyme with a lipofection reagent (TransIT-LT1, Mirus). After that, the cells were further cultured for about 1 day. After the culture, cell lysates were prepared using a cell lysis agent (Lysis buffer, Promega), and 5 μL each of the cell lysates was taken from each well and transferred to a 96-well microplate for measurement. An assay buffer (50 μL) containing native coelenterazine was simultaneously added to each well using a multichannel pipette. Immediately after the addition of the assay buffer, the microplate was moved into the black box of an image analyzer (LAS-4000, FujiFilm), and luminescence images were measured with a CCD camera (FIG. 19 and FIG. 20).

As a result, it was found that each of the novel artificial bioluminescent enzymes had a high luminescence activity as compared to a conventional natural luciferase or the like. In particular, it was able to be confirmed that ALuc45, ALuc49, ALuc50, and the like showed even stronger luminescence intensities even as compared to conventional ALucs (e.g., ALuc16 and ALuc30). Meanwhile, ALuc41, ALuc46, ALuc47, and the like showed relatively low luminescence intensities as compared to the conventional ALucs (e.g., ALuc16 and ALuc30).

Example 11

Metal Cation Effects on Bioluminescent Probe

Figure 21:
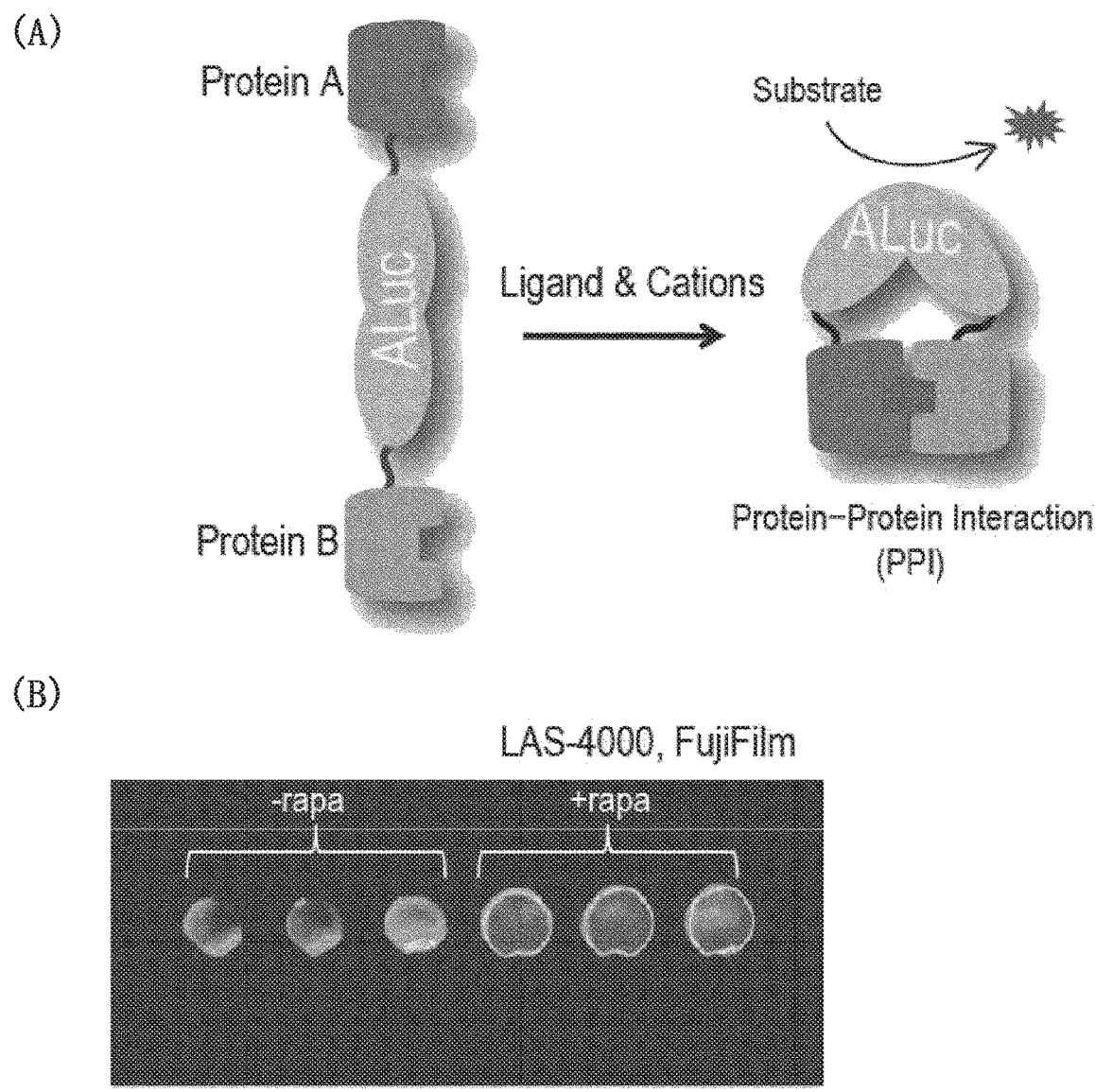
FIG. 21(A) is the working principle of a molecular strain sensor.
FIG. 21(B) is an image for showing a rapamycin-dependent change in luminescence intensity of the molecular strain sensor.
Figure 22:
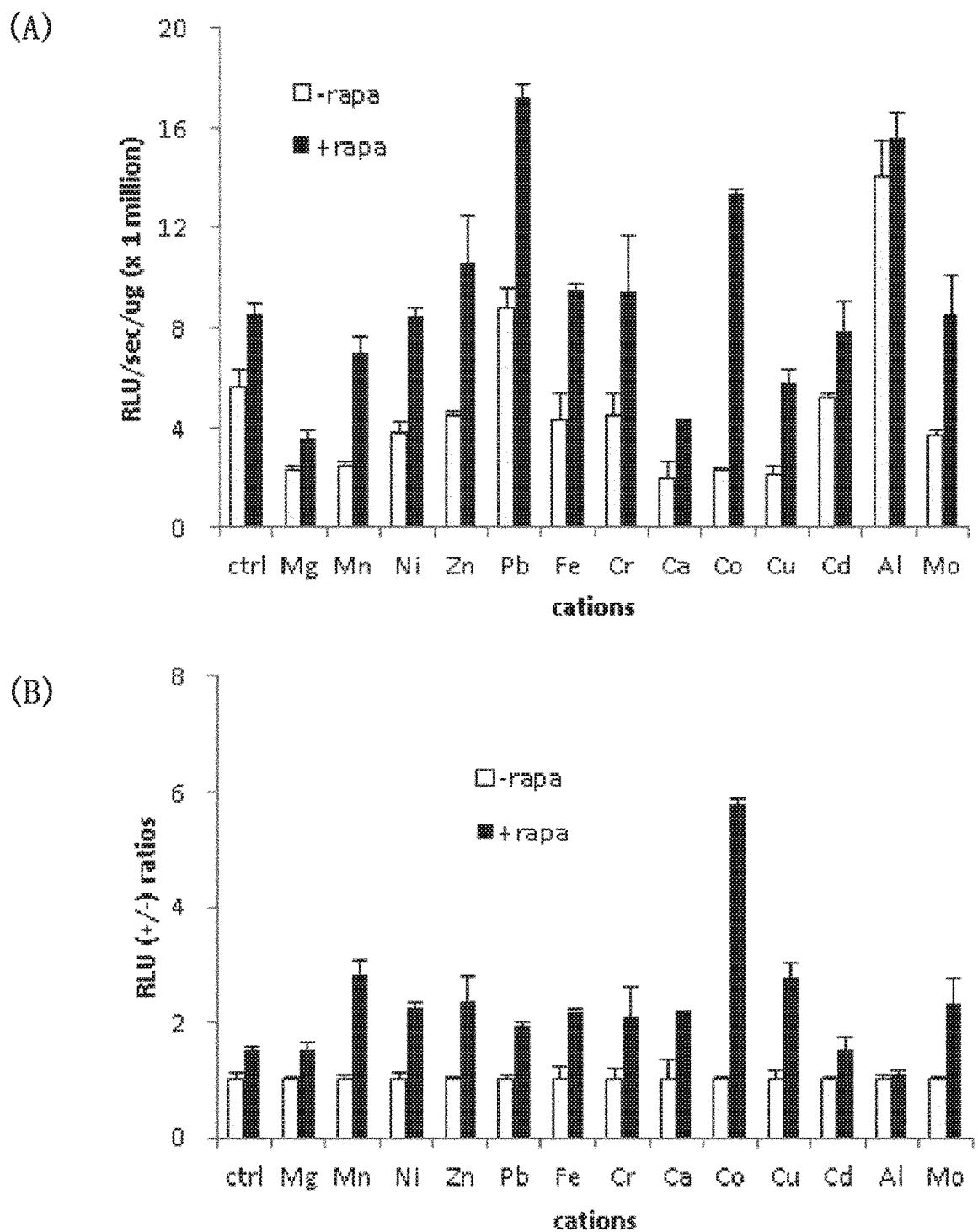
FIG. 22 are graphs for showing the metal ion sensitivity of a molecular strain sensor. A white bar and a black bar represent the conditions of absence and presence of rapamycin, respectively.

Metal ion effects on a bioluminescent probe were studied using a purified bioluminescent probe (FIG. 21 and FIG. 22).

First, for this experiment, a unique molecular probe in which rapamycin-binding proteins FRB and FKBP were arranged at the N-terminus and the C-terminus and an artificial bioluminescent enzyme (ALuc23) was inserted therebetween was developed (FIG. 21). In this probe, an intramolecular protein-protein interaction between FRB and FKBP occurs under the condition of the presence of rapamycin, and hence a molecular strain is applied to ALuc23 present between FRB and FKBP. As a result, the luminescence intensity is enhanced.

A pOPTHM vector encoding the molecular strain sensor was introduced into *Escherichia coli* to express the fusion protein (FIG. 21). After that, the fusion protein was purified with a His-tag affinity column, and the pure molecular strain sensor was extracted. In order to confirm the ligand sensitivity of the pure molecular strain sensor, the luminescence intensities of the molecular stress sensor were studied under the condition of the presence or absence of rapamycin. As a result, brighter luminescence was obtained under the condition of the presence of rapamycin (FIG. 21(B)).

Figure 23:
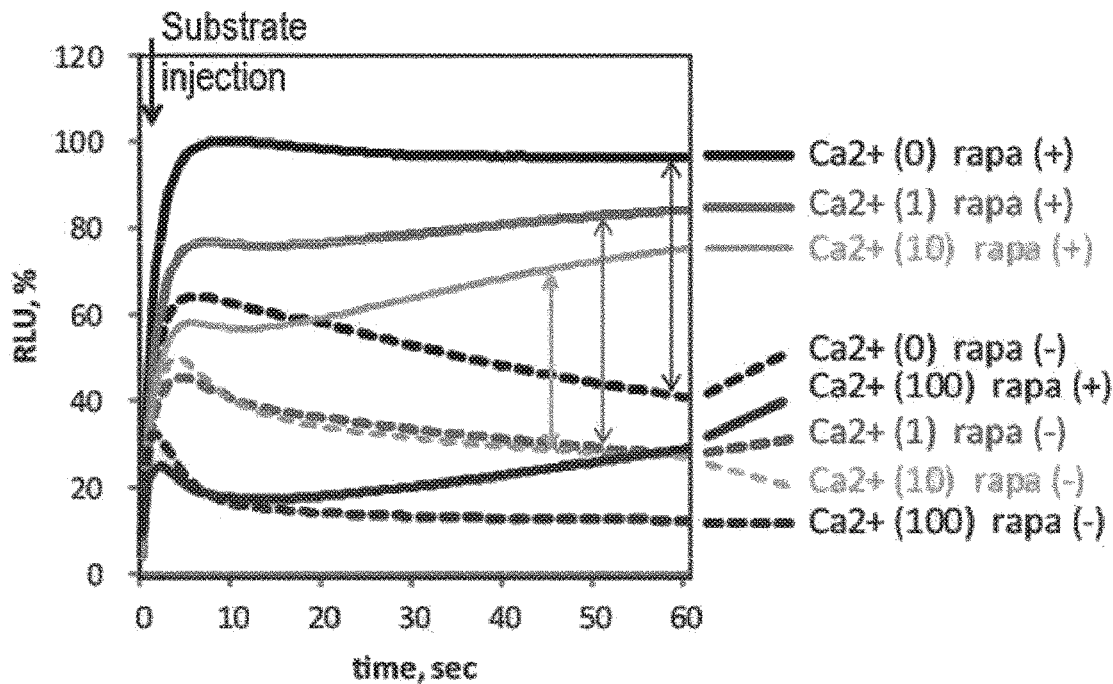
FIG. 23 are graphs for showing the stability of the luminescence intensity of a molecular strain sensor with respect to a metal ion concentration.
Figure 23:
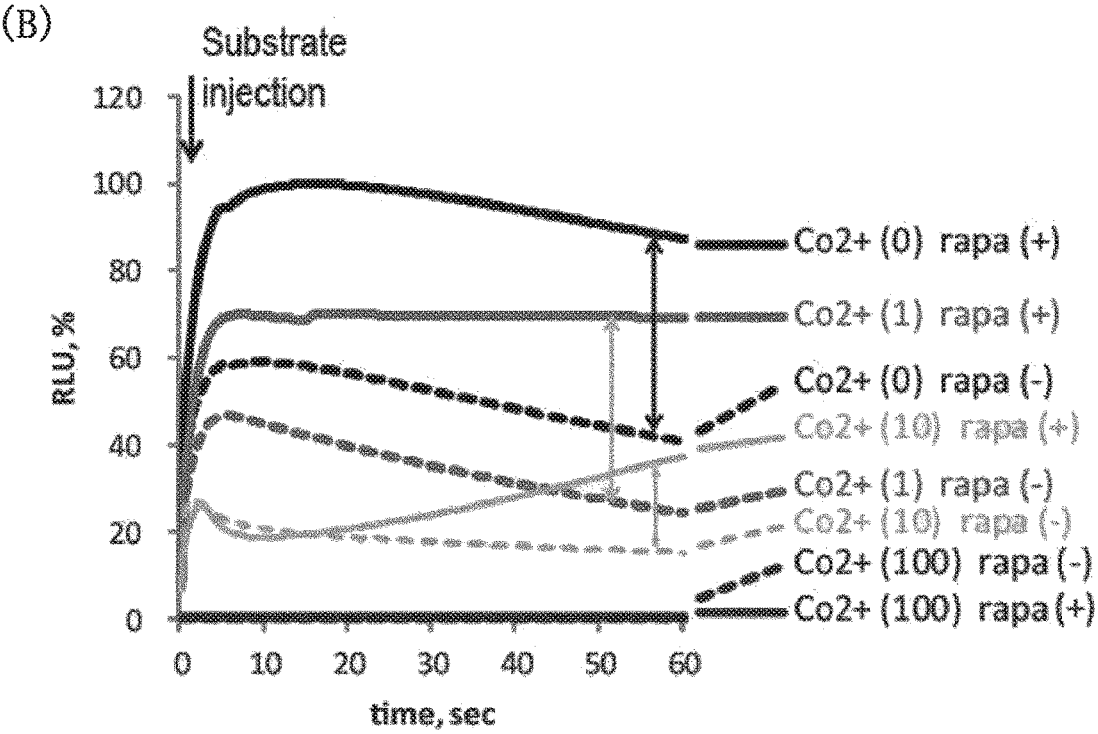

Further, in order to measure metal ion effects on this molecular strain sensor, changes in luminescence intensity were measured under the condition of the presence or absence of rapamycin and with various metal ions added (FIG. 22 and FIG. 23).

For this experiment, the concentration of the purified molecular strain sensor was adjusted to 0.1 mg/mL by dilution in a Tris-HCl buffer (pH 8.2). Rapamycin was added to the molecular strain sensor and the final concentration was adjusted to $10^{-5}$ M. After that, the resultant was diluted with metal ion-containing Tris-HCl buffer (pH 8.2) to make a 0.01 mg/mL molecular strain sensor solution. At this time, the final concentration of the metal ion added was 10 μg/mL. The solution was transferred to a 96-well microplate, and, while the substrate solution was added from a microinjector, luminescence intensities were measured with or without a metal ion.

The luminescence stability of the luminescent probe dependent on different metal ion concentrations was studied by a similar technique (FIG. 23). The substrate solution was added from a microinjector in the same manner as above, and then changes in luminescence intensity over 1 minute were measured.

The invention claimed is:

1. A polypeptide comprising any one of amino acid sequences (i) to (iii) below, and having luciferase activity:
   (i) an amino acid sequence selected from the group consisting of amino acid sequences of SEQ ID NOs: 2 to 11,
   (ii) an amino acid sequence selected from the group consisting of amino acid sequences of SEQ ID NOs: 2 to 11 in which no more than 10 amino acids are deleted, substituted, inserted, or added, or
   (iii) an amino acid sequence having at least 95% sequence identity to an amino acid sequence selected from the group consisting of amino acid sequences of SEQ ID NOs: 2 to 11.

2. A nucleic acid encoding the polypeptide of claim 1.

3. An expression vector comprising the nucleic acid of claim 2.

4. The expression vector according to claim 3, wherein the nucleic acid further comprises a nucleic acid encoding a heterologous protein so that the polypeptide encoded by the nucleic acid is expressed as a fusion protein with the heterologous protein.

5. An isolated transformed cell comprising the nucleic acid of claim 2.

6. A reporter protein comprising the polypeptide of claim 1.

7. A luminescent fusion protein, wherein the luminescent fusion protein comprises the reporter protein of claim 6, and a target protein or a peptide that recognizes a target protein.

8. The luminescent fusion protein according to claim 7, wherein the luminescent fusion protein further comprises a membrane localization signal (MLS) attached to a C-terminus of the reporter protein, and a target polypeptide inserted therebetween.

9. The luminescent fusion protein according to claim 8, wherein the target polypeptide inserted is a fluorescent protein or a luciferase.

10. The luminescent fusion protein according to claim 9, wherein the target polypeptide inserted is a polypeptide that changes form in a plasma membrane or a polypeptide having an amino acid sequence recognizable by the polypeptide that changes form in a plasma membrane.

11. An expression vector comprising a polynucleotide encoding the luminescent fusion protein of claim 8.

12. An isolated transformed cell comprising the expression vector of claim 11.

13. A reporter-gene assay method for assaying an expression position, an expression timing, or an expression amount upon expression of a target gene in a cell in response to external stimulus, the method comprising measuring luminescence of the transformed cell of claim 12.

14. The assay method according to claim 13, wherein the assay method is a reporter-gene assay or a two-hybrid assay.

15. A fusion protein for detecting a ligand, the fusion protein comprising the polypeptide of claim 1, which is located between a protein A and a protein B, which have a binding site to which the ligand binds, wherein the luciferase activity of the polypeptide varies depending on molecular strain that occurs when the protein A and the protein B have the ligand bound thereto.

16. An expression vector comprising a polynucleotide encoding the fusion protein of claim 15.

17. An isolated transformed cell comprising the expression vector of claim 16.

18. A method of detecting a ligand in a test sample, the method comprising a step of bringing the test sample into contact with the fusion protein of claim 15 and measuring luciferase activity to thereby detect the ligand in the test sample.

* * * * *

SEQUENCE LISTING

```
<160> NUMBER OF SEQ ID NOS: 45

<210> SEQ ID NO 1
<211> LENGTH: 194
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (11)..(11)
<223> OTHER INFORMATION: Xaa can be any hydrophobic amino acid
<220> FEATURE:
<221> NAME/KEY: misc_feature
<222> LOCATION: (13)..(13)
<223> OTHER INFORMATION: Xaa can be any hydrophobic amino acid
<220> FEATURE:
<221> NAME/KEY: misc_feature
<222> LOCATION: (19)..(19)
<223> OTHER INFORMATION: Xaa can be any hydrophilic amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (21)..(27)
<223> OTHER INFORMATION: Xaa can be any hydrophilic amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any hydrophilic amino acid
```

```
<220> FEATURE:
<221> NAME/KEY: misc_feature
<222> LOCATION: (37)..(37)
<223> OTHER INFORMATION: Xaa can be any hydrophobic amino acid
<220> FEATURE:
<221> NAME/KEY: misc_feature
<222> LOCATION: (38)..(39)
<223> OTHER INFORMATION: Xaa can be any neutral amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any hydrophobic amino acid
<220> FEATURE:
<221> NAME/KEY: misc_feature
<222> LOCATION: (42)..(43)
<223> OTHER INFORMATION: Xaa can be any hydrophilic amino acid
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any neutral amino acid
<220> FEATURE:
<221> NAME/KEY: misc_feature
<222> LOCATION: (51)..(51)
<223> OTHER INFORMATION: Xaa can be any hydrophobic amino acid
<220> FEATURE:
<221> NAME/KEY: misc_feature
<222> LOCATION: (52)..(52)
<223> OTHER INFORMATION: Xaa can be any hydrophilic amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any hydrophobic amino acid
<220> FEATURE:
<221> NAME/KEY: misc_feature
<222> LOCATION: (74)..(74)
<223> OTHER INFORMATION: Xaa can be any hydrophilic amino acid
<220> FEATURE:
<221> NAME/KEY: misc_feature
<222> LOCATION: (88)..(88)
<223> OTHER INFORMATION: Xaa can be any hydrophilic amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any hydrophobic amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (110)..(111)
```

```
<223> OTHER INFORMATION: Xaa can be any hydrophilic amino acid
<220> FEATURE:
<221> NAME/KEY: misc_feature
<222> LOCATION: (120)..(121)
<223> OTHER INFORMATION: Xaa can be any hydrophobic amino acid
<220> FEATURE:
<221> NAME/KEY: misc_feature
<222> LOCATION: (124)..(125)
<223> OTHER INFORMATION: Xaa can be any hydrophobic amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any neutral amino acid
<220> FEATURE:
<221> NAME/KEY: misc_feature
<222> LOCATION: (154)..(154)
<223> OTHER INFORMATION: Xaa can be any hydrophobic amino acid
<220> FEATURE:
<221> NAME/KEY: misc_feature
<222> LOCATION: (157)..(157)
<223> OTHER INFORMATION: Xaa can be any hydrophobic amino acid
<220> FEATURE:
<221> NAME/KEY: misc_feature
<222> LOCATION: (160)..(160)
<223> OTHER INFORMATION: Xaa can be any hydrophobic amino acid
<220> FEATURE:
<221> NAME/KEY: misc_feature
<222> LOCATION: (164)..(164)
<223> OTHER INFORMATION: Xaa can be any hydrophobic amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any hydrophilic amino acid
<220> FEATURE:
<221> NAME/KEY: misc_feature
<222> LOCATION: (176)..(176)
<223> OTHER INFORMATION: Xaa can be any neutral amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any hydrophilic amino acid
<220> FEATURE:
<221> NAME/KEY: misc_feature
<222> LOCATION: (185)..(185)
<223> OTHER INFORMATION: Xaa can be any neutral amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any neutral amino acid
<220> FEATURE:
<221> NAME/KEY: misc_feature
<222> LOCATION: (191)..(191)
<223> OTHER INFORMATION: Xaa can be any hydrophobic amino acid
<220> FEATURE:
<221> NAME/KEY: misc_feature
<222> LOCATION: (192)..(192)
<223> OTHER INFORMATION: Xaa can be any neutral amino acid

<400> SEQUENCE: 1

Met Met Gly Ile Lys Val Leu Phe Ala Leu Xaa Cys Xaa Ala Leu Val
1               5                   10                  15
```

Gln Ala Xaa Xaa Xaa Xaa Xaa Xaa Xaa Asp Ile Val Xaa Val
            20                  25                  30

Xaa Gly Xaa Phe Xaa Xaa Xaa Xaa Xaa Xaa Asp Xaa Xaa Phe Thr
        35                  40                  45

Ile Xaa Xaa Xaa Arg Gly Lys Leu Pro Gly Lys Lys Leu Pro Xaa Glu
    50                  55                  60

Val Leu Xaa Glu Xaa Glu Ala Asn Ala Xaa Lys Ala Gly Cys Thr Arg
65              70                  75                  80

Gly Cys Leu Ile Cys Leu Ser Xaa Xaa Xaa Cys Thr Ala Lys Xaa Lys
                85                  90                  95

Lys Trp Leu Pro Gly Arg Cys Xaa Ser Xaa Glu Gly Asp Xaa Xaa Thr
                100                 105                 110

Gly Gln Gly Gly Ile Gly Glu Xaa Xaa Val Asp Xaa Xaa Glu Ile Pro
            115                 120                 125

Gly Phe Lys Xaa Leu Xaa Pro Met Glu Gln Phe Ile Ala Gln Val Asp
            130                 135                 140

Leu Cys Ala Asp Cys Thr Thr Gly Cys Xaa Lys Gly Xaa Ala Asn Xaa
145                 150                 155                 160

Lys Cys Ser Xaa Leu Leu Xaa Lys Trp Leu Pro Xaa Arg Cys Ala Xaa
                165                 170                 175

Phe Ala Asp Lys Ile Gln Xaa Xaa Xaa Xaa Xaa Ile Lys Gly Xaa Xaa
                180                 185                 190

Gly Ser

<210> SEQ ID NO 2
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 2

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
        35                  40                  45

Ile Ser Ala Asp Arg Gly Lys Leu Pro Gly Lys Lys Leu Pro Lys Glu
    50                  55                  60

Val Leu Ile Glu Ile Glu Ala Asn Ala Lys Lys Ala Gly Cys Thr Arg
65              70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
                100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
            130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Thr Ile Lys Gly Leu Ala

-continued

```
                180                 185                 190
Gly Ser

<210> SEQ ID NO 3
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 3

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
        35                  40                  45

Ile Ser Ala Asp Arg Gly Lys Leu Pro Gly Lys Lys Leu Pro Lys Glu
    50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125

Gly Phe Lys Asp Leu Thr Pro Met Glu Gln Phe Ile Ala Gln Val Asp
    130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Thr Glu Val Asp Thr Ile Lys Gly Leu Ala
            180                 185                 190

Gly Ser

<210> SEQ ID NO 4
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 4

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
        35                  40                  45

Ile Ser Ala Asp Arg Gly Lys Leu Pro Gly Lys Lys Leu Pro Lys Glu
    50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95
```

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
            165                 170                 175

Phe Ala Asp Lys Ile Gln Lys Glu Gln Asp Thr Ile Lys Gly Leu Ala
            180                 185                 190

Gly Ser

<210> SEQ ID NO 5
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 5

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
            85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
            165                 170                 175

Phe Ala Asp Lys Ile Gln Lys Glu Val Asp Asn Ile Lys Gly Leu Ala
            180                 185                 190

Gly Ser

<210> SEQ ID NO 6
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 6

Met Met Gly Ile Lys Val Leu Phe Ala Leu Val Cys Leu Ala Leu Val
1               5                   10                  15

Gln Ala Lys Pro Thr Glu Asp Glu Asp Glu Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
50                      55                  60

Val Leu Ile Glu Ile Glu Ala Asn Ala Lys Lys Ala Gly Cys Thr Arg
65                      70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
            130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
            165                 170                 175

Phe Ala Asp Lys Ile Gln Ser Glu Val Ala Thr Ile Lys Gly Leu Ala
            180                 185                 190

Gly Ser

<210> SEQ ID NO 7
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 7

Met Met Gly Ile Lys Val Leu Phe Ala Leu Val Cys Leu Ala Leu Val
1               5                   10                  15

Gln Ala Lys Pro Thr Glu Asp Glu Asp Glu Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
50                      55                  60

Val Leu Ile Glu Ile Glu Ala Asn Ala Lys Lys Ala Gly Cys Thr Arg
65                      70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
            130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser

```
                    165                 170                 175

Phe Ala Asp Lys Ile Gln Lys Glu Val Gly Thr Ile Lys Gly Leu Leu
            180                 185                 190

Gly Ser

<210> SEQ ID NO 8
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 8

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
    50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125

Gly Phe Lys Asp Leu Thr Pro Met Glu Gln Phe Ile Ala Gln Val Asp
    130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Thr Ile Lys Gly Leu Trp
            180                 185                 190

Gly Ser

<210> SEQ ID NO 9
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 9

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
    50                  55                  60

Val Leu Ile Glu Ile Glu Ala Asn Ala Lys Lys Ala Gly Cys Thr Arg
65                  70                  75                  80
```

Gly Cys Leu Ile Cys Leu Ser Lys Ile Lys Cys Thr Ala Lys Met Lys
              85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125

Gly Phe Lys Asp Leu Thr Pro Met Glu Gln Phe Ile Ala Gln Val Asp
    130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Tyr Ile Lys Gly Leu Ala
            180                 185                 190

Gly Ser

<210> SEQ ID NO 10
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 10

Met Met Gly Ile Lys Val Leu Phe Ala Leu Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
        115                 120                 125

Gly Phe Lys Asp Leu Thr Pro Met Glu Gln Phe Ile Ala Gln Val Asp
    130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Phe Ile Lys Gly Leu Ala
            180                 185                 190

Gly Ser

<210> SEQ ID NO 11
<211> LENGTH: 194
<212> TYPE: PRT
<213> ORGANISM: Artificial sequence
<220> FEATURE:
<223> OTHER INFORMATION: Synthetic Sequence

<400> SEQUENCE: 11

Met Met Gly Ile Lys Val Leu Phe Ala Leu Val Cys Leu Ala Leu Val
1               5                   10                  15

Gln Ala Lys Pro Thr Glu Asp Glu Asp Asp Ile Val Asp Val
            20                  25                  30

Val Gly Asn Phe Trp Ala Ile Gly Val Asp Asn Asp Arg Asp Phe Thr
            35                  40                  45

Ile Ser Ala Asp Arg Gly Lys Leu Pro Gly Lys Lys Leu Pro Lys Glu
        50                  55                  60

Val Leu Ile Glu Ile Glu Ala Asn Ala Lys Lys Ala Gly Cys Thr Arg
65                  70                  75                  80

Gly Cys Leu Ile Cys Leu Ser Lys Ile Lys Cys Thr Ala Lys Met Lys
                85                  90                  95

Lys Trp Leu Pro Gly Arg Cys His Ser Tyr Glu Gly Asp Lys Asp Thr
            100                 105                 110

Gly Gln Gly Gly Ile Gly Glu Pro Ile Val Asp Ala Pro Glu Ile Pro
            115                 120                 125

Gly Phe Lys Asp Leu Thr Pro Met Glu Gln Phe Ile Ala Gln Val Asp
130                 135                 140

Leu Cys Ala Asp Cys Thr Thr Gly Cys Leu Lys Gly Leu Ala Asn Val
145                 150                 155                 160

Lys Cys Ser Ala Leu Leu Lys Lys Trp Leu Pro Asp Arg Cys Ala Ser
                165                 170                 175

Phe Ala Asp Lys Ile Gln Lys Glu Val Asp Trp Ile Lys Gly Leu Ala
            180                 185                 190

Gly Ser

<210> SEQ ID NO 12
<211> LENGTH: 213
<212> TYPE: PRT
<213> ORGANISM: Artificial sequence
<220> FEATURE:
<223> OTHER INFORMATION: Synthetic Sequence
<220> FEATURE:
<221> NAME/KEY: misc_feature
<222> LOCATION: (11)..(11)
<223> OTHER INFORMATION: Xaa can be any hydrophobic amino acid
<220> FEATURE:
<221> NAME/KEY: misc_feature
<222> LOCATION: (13)..(13)
<223> OTHER INFORMATION: Xaa can be any hydrophobic amino acid
<220> FEATURE:
<221> NAME/KEY: misc_feature
<222> LOCATION: (19)..(19)
<223> OTHER INFORMATION: Xaa can be any hydrophilic amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (21)..(27)
<223> OTHER INFORMATION: Xaa can be any hydrophilic amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)

```
<223> OTHER INFORMATION: Xaa can be any hydrophilic amino acid
<220> FEATURE:
<221> NAME/KEY: misc_feature
<222> LOCATION: (37)..(37)
<223> OTHER INFORMATION: Xaa can be any hydrophobic amino acid
<220> FEATURE:
<221> NAME/KEY: misc_feature
<222> LOCATION: (38)..(39)
<223> OTHER INFORMATION: Xaa can be any neutral amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any hydrophobic amino acid
<220> FEATURE:
<221> NAME/KEY: misc_feature
<222> LOCATION: (42)..(43)
<223> OTHER INFORMATION: Xaa can be any hydrophilic amino acid
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any neutral amino acid
<220> FEATURE:
<221> NAME/KEY: misc_feature
<222> LOCATION: (51)..(69)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any hydrophobic amino acid
<220> FEATURE:
<221> NAME/KEY: misc_feature
<222> LOCATION: (71)..(71)
<223> OTHER INFORMATION: Xaa can be any hydrophilic amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any hydrophobic amino acid
<220> FEATURE:
<221> NAME/KEY: misc_feature
<222> LOCATION: (93)..(93)
<223> OTHER INFORMATION: Xaa can be any hydrophilic amino acid
<220> FEATURE:
<221> NAME/KEY: misc_feature
<222> LOCATION: (107)..(107)
<223> OTHER INFORMATION: Xaa can be any hydrophilic amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any hydrophobic amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (124)..(125)
<223> OTHER INFORMATION: Xaa can be any hydrophobic amino acid
<220> FEATURE:
<221> NAME/KEY: misc_feature
```

```
<222> LOCATION: (129)..(130)
<223> OTHER INFORMATION: Xaa can be any hydrophilic amino acid
<220> FEATURE:
<221> NAME/KEY: misc_feature
<222> LOCATION: (139)..(140)
<223> OTHER INFORMATION: Xaa can be any hydrophobic amino acid
<220> FEATURE:
<221> NAME/KEY: misc_feature
<222> LOCATION: (143)..(144)
<223> OTHER INFORMATION: Xaa can be any hydrophobic amino acid
<220> FEATURE:
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any neutral amino acid
<220> FEATURE:
<221> NAME/KEY: misc_feature
<222> LOCATION: (173)..(173)
<223> OTHER INFORMATION: Xaa can be any hydrophobic amino acid
<220> FEATURE:
<221> NAME/KEY: misc_feature
<222> LOCATION: (176)..(176)
<223> OTHER INFORMATION: Xaa can be any hydrophobic amino acid
<220> FEATURE:
<221> NAME/KEY: misc_feature
<222> LOCATION: (179)..(179)
<223> OTHER INFORMATION: Xaa can be any hydrophobic amino acid
<220> FEATURE:
<221> NAME/KEY: misc_feature
<222> LOCATION: (183)..(183)
<223> OTHER INFORMATION: Xaa can be any hydrophobic amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any hydrophilic amino acid
<220> FEATURE:
<221> NAME/KEY: misc_feature
<222> LOCATION: (195)..(195)
<223> OTHER INFORMATION: Xaa can be any hydrophilic amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any hydrophilic amino acid
<220> FEATURE:
<221> NAME/KEY: misc_feature
<222> LOCATION: (204)..(204)
<223> OTHER INFORMATION: Xaa can be any neutral amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any neutral amino acid
<220> FEATURE:
<221> NAME/KEY: misc_feature
<222> LOCATION: (210)..(210)
<223> OTHER INFORMATION: Xaa can be any hydrophobic amino acid
<220> FEATURE:
<221> NAME/KEY: misc_feature
<222> LOCATION: (211)..(211)
<223> OTHER INFORMATION: Xaa can be any neutral amino acid

<400> SEQUENCE: 12

Met Met Gly Ile Lys Val Leu Phe Ala Leu Xaa Cys Xaa Ala Leu Val
1               5                   10                  15
```

Gln Ala Xaa Xaa Xaa Xaa Xaa Xaa Xaa Asp Ile Val Xaa Val
        20                  25                  30

Xaa Gly Xaa Phe Xaa Xaa Xaa Xaa Xaa Asp Xaa Xaa Phe Thr
        35                  40                  45

Ile Xaa Xaa Xaa Xaa Xaa Xaa Xaa Xaa Xaa Xaa Xaa Xaa Xaa
    50                  55                  60

Xaa Xaa Xaa Xaa Xaa Xaa Arg Gly Lys Leu Pro Gly Lys Lys Leu
65                  70                  75                  80

Pro Xaa Glu Val Leu Xaa Glu Xaa Glu Ala Asn Ala Xaa Lys Ala Gly
            85                  90                  95

Cys Thr Arg Gly Cys Leu Ile Cys Leu Ser Xaa Xaa Cys Thr Ala
            100                 105                 110

Lys Xaa Lys Lys Trp Leu Pro Gly Arg Cys Xaa Ser Xaa Glu Gly Asp
    115                 120                 125

Xaa Xaa Thr Gly Gln Gly Gly Ile Gly Glu Xaa Xaa Val Asp Xaa Xaa
130                 135                 140

Glu Ile Pro Gly Phe Lys Xaa Leu Xaa Pro Met Glu Gln Phe Ile Ala
145                 150                 155                 160

Gln Val Asp Leu Cys Ala Asp Cys Thr Thr Gly Cys Xaa Lys Gly Xaa
                165                 170                 175

Ala Asn Xaa Lys Cys Ser Xaa Leu Leu Xaa Lys Trp Leu Pro Xaa Arg
        180                 185                 190

Cys Ala Xaa Phe Ala Asp Lys Ile Gln Xaa Xaa Xaa Xaa Ile Lys
        195                 200                 205

Gly Xaa Xaa Gly Ser
        210

<210> SEQ ID NO 13
<211> LENGTH: 213
<212> TYPE: PRT
<213> ORGANISM: Artificial sequence
<220> FEATURE:
<223> OTHER INFORMATION: Synthetic Sequence

<400> SEQUENCE: 13

Met Met Gly Ile Lys Val Leu Phe Ala Leu Val Cys Leu Ala Leu Val
1               5                   10                  15

Gln Ala Asn His His His His His His Asp Ile Val Asp Val
        20                  25                  30

Val Gly Asn Phe Trp Ala Ile Gly Val Asp Asn Asp Arg Asp Phe Thr
        35                  40                  45

Ile Ser Glu Asp Met Asn Val Ile Ser Arg Thr Asp Val Asp Ala
    50                  55                  60

Asn Arg Ala Asp Arg Ala Asp Arg Gly Lys Leu Pro Gly Lys Lys Leu
65                  70                  75                  80

Pro Lys Glu Val Leu Ile Glu Ile Glu Ala Asn Ala Lys Lys Ala Gly
            85                  90                  95

Cys Thr Arg Gly Cys Leu Ile Cys Leu Ser Lys Ile Lys Cys Thr Ala
            100                 105                 110

Lys Met Lys Lys Trp Leu Pro Gly Arg Cys His Ser Tyr Glu Gly Asp
    115                 120                 125

Lys Asp Thr Gly Gln Gly Gly Ile Gly Glu Pro Ile Val Asp Ala Pro
130                 135                 140

Glu Ile Pro Gly Phe Lys Asp Leu Thr Pro Met Glu Gln Phe Ile Ala
145                 150                 155                 160

Gln Val Asp Leu Cys Ala Asp Cys Thr Thr Gly Cys Leu Lys Gly Leu
            165                 170                 175

Ala Asn Val Lys Cys Ser Ala Leu Leu Lys Lys Trp Leu Pro Asp Arg
            180                 185                 190

Cys Ala Ser Phe Ala Asp Lys Ile Gln Lys Glu Val Asp Thr Ile Lys
            195                 200                 205

Gly Leu Ala Gly Ser
    210

<210> SEQ ID NO 14
<211> LENGTH: 212
<212> TYPE: PRT
<213> ORGANISM: Artificial sequence
<220> FEATURE:
<223> OTHER INFORMATION: Synthetic Sequence

<400> SEQUENCE: 14

Met Met Gly Ile Lys Val Leu Phe Ala Leu Ile Cys Phe Ala Leu Val
1               5                   10                  15

Gln Ala Asn His His His His His His His Asp Ile Val Gly Val
            20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
            85                  90                  95

Thr Arg Gly Cys Leu Ile Cys Leu Ser His Asp Trp Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Val Val Asp Ile Leu Glu
            130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
            165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
            195                 200                 205

Ala Gly Gly Ser
    210

<210> SEQ ID NO 15
<211> LENGTH: 212
<212> TYPE: PRT
<213> ORGANISM: Artificial sequence
<220> FEATURE:
<223> OTHER INFORMATION: Synthetic Sequence

<400> SEQUENCE: 15

Met Met Gly Ile Lys Val Leu Phe Ala Leu Ile Cys Phe Ala Leu Val
1               5                   10                  15

Gln Ala Asn His His His His His His His His Asp Ile Val Gly Val

```
            20                  25                  30
Glu Gly Lys Phe Gly Asn Thr Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60

Arg Ala Asp Arg Gly Arg Gly Lys Leu Pro Gly Lys Lys Leu Pro
65                  70                  75                  80

Leu Glu Val Leu Lys Glu Leu Ala Asn Ala Gln Lys Ala Gly Cys
                85                  90                  95

Thr Arg Gly Cys Leu Ile Cys Leu Ser His Asp Trp Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Val Val Asp Ile Pro Glu
            130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
            195                 200                 205

Ala Gly Gly Ser
        210

<210> SEQ ID NO 16
<211> LENGTH: 212
<212> TYPE: PRT
<213> ORGANISM: Artificial sequence
<220> FEATURE:
<223> OTHER INFORMATION: Synthetic Sequence

<400> SEQUENCE: 16

Met Met Gly Ile Lys Val Leu Phe Ala Leu Ile Cys Phe Ala Leu Val
1               5                   10                  15

Gln Ala Asn His His His His His His His Asp Ile Val Gly Val
            20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Glu
            115                 120                 125

Glu Thr Gly Gln Gly Gly Ile Gly Glu Ala Ile Val Asp Ile Pro Glu
            130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Trp Lys Gly Trp Ala
```

```
                        165                 170                 175

Asn Leu Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 17
<211> LENGTH: 212
<212> TYPE: PRT
<213> ORGANISM: Artificial sequence
<220> FEATURE:
<223> OTHER INFORMATION: Synthetic Sequence

<400> SEQUENCE: 17

Met Met Gly Ile Lys Val Leu Phe Ala Leu Ile Cys Phe Ala Leu Val
1               5                   10                  15

Gln Ala Asn His His His His His His Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Gly Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Trp Lys Gly Trp Ala
                165                 170                 175

Asn Leu Lys Cys Ser Leu Leu Leu Lys Trp Leu Pro Ser Arg Cys
            180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 18
<211> LENGTH: 212
<212> TYPE: PRT
<213> ORGANISM: Artificial sequence
<220> FEATURE:
<223> OTHER INFORMATION: Synthetic Sequence

<400> SEQUENCE: 18

Met Met Gly Ile Lys Val Leu Phe Ala Leu Ile Cys Phe Ala Leu Val
1               5                   10                  15

Gln Ala Asn Tyr His His His His His His Asp Ile Val Gly Val
            20                  25                  30
```

```
Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
 50                  55                  60

Arg Ala Asp Arg Gly Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Val Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
 130                 135                 140

Ile Pro Gly Phe Lys Gly Leu Ala Pro Met Glu Gln Phe Ile Ala Gln
145                 150                 155                 160

Val Asp Leu Cys Ala Asp Cys Thr Thr Gly Cys Trp Lys Gly Trp Ala
                165                 170                 175

Asn Leu Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
            195                 200                 205

Ala Gly Gly Ser
        210

<210> SEQ ID NO 19
<211> LENGTH: 6
<212> TYPE: PRT
<213> ORGANISM: Artificial sequence
<220> FEATURE:
<223> OTHER INFORMATION: Synthetic Sequence - His-tag

<400> SEQUENCE: 19

His His His His His His
1               5

<210> SEQ ID NO 20
<211> LENGTH: 8
<212> TYPE: PRT
<213> ORGANISM: Artificial sequence
<220> FEATURE:
<223> OTHER INFORMATION: Synthetic Sequence - FLAG-tag

<400> SEQUENCE: 20

Asp Tyr Lys Asp Asp Asp Asp Lys
1               5

<210> SEQ ID NO 21
<211> LENGTH: 10
<212> TYPE: PRT
<213> ORGANISM: Artificial sequence
<220> FEATURE:
<223> OTHER INFORMATION: Synthetic Sequence - Myc-tag

<400> SEQUENCE: 21

Glu Gln Lys Leu Ile Ser Glu Glu Asp Leu
1               5                   10

<210> SEQ ID NO 22
<211> LENGTH: 9
<212> TYPE: PRT
```

```
<213> ORGANISM: Artificial sequence
<220> FEATURE:
<223> OTHER INFORMATION: Synthetic Sequence - HA-tag

<400> SEQUENCE: 22

Tyr Pro Tyr Asp Val Pro Asp Tyr Ala
1               5

<210> SEQ ID NO 23
<211> LENGTH: 14
<212> TYPE: PRT
<213> ORGANISM: Artificial sequence
<220> FEATURE:
<223> OTHER INFORMATION: Synthetic Sequence - V5-tag

<400> SEQUENCE: 23

Gly Lys Pro Ile Pro Asn Pro Leu Leu Gly Leu Asp Ser Thr
1               5                   10

<210> SEQ ID NO 24
<211> LENGTH: 11
<212> TYPE: PRT
<213> ORGANISM: Artificial sequence
<220> FEATURE:
<223> OTHER INFORMATION: Synthetic Sequence - T7-tag

<400> SEQUENCE: 24

Met Ala Ser Met Thr Gly Gly Gln Gln Met Gly
1               5                   10

<210> SEQ ID NO 25
<211> LENGTH: 4
<212> TYPE: PRT
<213> ORGANISM: Artificial sequence
<220> FEATURE:
<223> OTHER INFORMATION: Synthetic Sequence

<400> SEQUENCE: 25

Asp Glu Val Asp
1

<210> SEQ ID NO 26
<211> LENGTH: 4
<212> TYPE: PRT
<213> ORGANISM: Artificial sequence
<220> FEATURE:
<223> OTHER INFORMATION: Synthetic Sequence

<400> SEQUENCE: 26

Ile Glu Thr Asp
1

<210> SEQ ID NO 27
<211> LENGTH: 11
<212> TYPE: PRT
<213> ORGANISM: Artificial sequence
<220> FEATURE:
<223> OTHER INFORMATION: Synthetic Sequence

<400> SEQUENCE: 27

Met Leu Cys Cys Met Arg Arg Thr Lys Gln Val
1               5                   10

<210> SEQ ID NO 28
<211> LENGTH: 10
<212> TYPE: PRT
<213> ORGANISM: Artificial sequence
```

```
<220> FEATURE:
<223> OTHER INFORMATION: Synthetic Sequence

<400> SEQUENCE: 28

Gly Arg Lys Lys Arg Gln Arg Arg Arg
1               5                   10

<210> SEQ ID NO 29
<211> LENGTH: 4
<212> TYPE: PRT
<213> ORGANISM: Artificial sequence
<220> FEATURE:
<223> OTHER INFORMATION: Synthetic Sequence

<400> SEQUENCE: 29

Lys Asp Glu Leu
1

<210> SEQ ID NO 30
<211> LENGTH: 8
<212> TYPE: PRT
<213> ORGANISM: Artificial sequence
<220> FEATURE:
<223> OTHER INFORMATION: Synthetic Sequence

<400> SEQUENCE: 30

Asp Pro Lys Lys Lys Arg Lys Val
1               5

<210> SEQ ID NO 31
<211> LENGTH: 212
<212> TYPE: PRT
<213> ORGANISM: Artificial sequence
<220> FEATURE:
<223> OTHER INFORMATION: Synthetic Sequence - ALuc16

<400> SEQUENCE: 31

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
        50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
            180                 185                 190
```

```
Ala Thr Phe Ala Ser Lys Ile Gln Ala Gln Val Asp Lys Ile Lys Gly
        195                 200                 205

Ala Gly Gly Ser
    210

<210> SEQ ID NO 32
<211> LENGTH: 212
<212> TYPE: PRT
<213> ORGANISM: Artificial sequence
<220> FEATURE:
<223> OTHER INFORMATION: Synthetic Sequence - ALuc23

<400> SEQUENCE: 32

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 33
<211> LENGTH: 212
<212> TYPE: PRT
<213> ORGANISM: Artificial sequence
<220> FEATURE:
<223> OTHER INFORMATION: Synthetic Sequence - ALuc25

<400> SEQUENCE: 33

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
```

```
        50                  55                  60
Arg Gly Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
                115                 120                 125

Glu Thr Gly Gln Gly Gly Ile Gly Glu Ala Ile Val Asp Ile Pro Glu
                130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
                195                 200                 205

Ala Gly Gly Ser
        210

<210> SEQ ID NO 34
<211> LENGTH: 212
<212> TYPE: PRT
<213> ORGANISM: Artificial sequence
<220> FEATURE:
<223> OTHER INFORMATION: Synthetic Sequence - ALuc30

<400> SEQUENCE: 34

Met Met Gly Ile Lys Val Leu Phe Ala Leu Ile Cys Phe Ala Leu Val
  1               5                  10                  15

Gln Ala Asn His His His His His His Asp Ile Val Gly Val
                 20                  25                  30

Glu Gly Lys Phe Gly Thr Thr Asp Leu Glu Thr Asp Leu Phe Thr Ile
             35                  40                  45

Val Glu Asp Met Asn Val Ile Ser Arg Asp Thr Asp Val Asp Ala Asn
 50                  55                  60

Arg Ala Asp Arg Gly Arg Arg Gly Lys Leu Pro Gly Lys Lys Leu Pro
 65                  70                  75                  80

Leu Glu Val Leu Lys Glu Leu Glu Ala Asn Ala Gln Lys Ala Gly Cys
                 85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
                115                 120                 125

Glu Thr Gly Gln Gly Gly Ile Gly Glu Ala Ile Val Asp Ile Pro Glu
                130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
```

195                 200                 205

Ala Gly Gly Ser
    210

<210> SEQ ID NO 35
<211> LENGTH: 212
<212> TYPE: PRT
<213> ORGANISM: Artificial sequence
<220> FEATURE:
<223> OTHER INFORMATION: Synthetic Sequence - ALuc34

<400> SEQUENCE: 35

Met Met Gly Ile Lys Val Leu Phe Ala Leu Ile Cys Phe Ala Leu Val
1               5                   10                  15

Gln Ala Asn Met Met Asp Tyr Lys Asp Asp Asp Lys Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 36
<211> LENGTH: 184
<212> TYPE: PRT
<213> ORGANISM: Artificial Sequence
<220> FEATURE:
<223> OTHER INFORMATION: Synthetic Sequence - Renilla muelleri CBP
      (2HPS)

<400> SEQUENCE: 36

Glu Ile Thr Glu Ser Glu Arg Ala Tyr His Leu Arg Lys Met Lys Thr
1               5                   10                  15

Arg Met Gln Arg Val Asp Val Thr Gly Asp Gly Phe Ile Ser Arg Glu
            20                  25                  30

Asp Tyr Glu Leu Ile Ala Val Arg Ile Ala Lys Ile Ala Lys Leu Ser
        35                  40                  45

Ala Glu Lys Ala Glu Glu Thr Arg Gln Glu Phe Leu Arg Val Ala Asp
    50                  55                  60

```
Gln Leu Gly Leu Ala Pro Gly Val Arg Ile Ser Val Glu Glu Ala Ala
 65                  70                  75                  80

Val Asn Ala Thr Asp Ser Leu Leu Lys Met Lys Gly Glu Glu Lys Ala
                 85                  90                  95

Met Ala Val Ile Gln Ser Leu Ile Met Tyr Asp Cys Ile Asp Thr Asp
            100                 105                 110

Lys Asp Gly Tyr Val Ser Leu Pro Glu Phe Lys Ala Phe Leu Gln Ala
        115                 120                 125

Val Gly Pro Asp Leu Thr Asp Asp Lys Ala Ile Thr Cys Phe Asn Thr
    130                 135                 140

Leu Asp Phe Asn Lys Asn Gly Gln Ile Ser Arg Asp Glu Phe Leu Val
145                 150                 155                 160

Thr Val Asn Asp Phe Leu Phe Gly Leu Glu Glu Thr Ala Leu Ala Asn
                165                 170                 175

Ala Phe Tyr Gly Asp Leu Val Asp
            180

<210> SEQ ID NO 37
<211> LENGTH: 189
<212> TYPE: PRT
<213> ORGANISM: Artificial Sequence
<220> FEATURE:
<223> OTHER INFORMATION: Synthetic Sequence - Clytia gregaria Clytin
      (3KPX)

<400> SEQUENCE: 37

Val Lys Leu Lys Thr Asn Phe Glu Asp Pro Lys Trp Val Asn Arg His
  1               5                  10                  15

Lys Phe Met Phe Asn Phe Leu Asp Ile Asn Gly Asn Gly Lys Ile Thr
                 20                  25                  30

Leu Asp Glu Ile Val Ser Lys Ala Ser Asp Asp Ile Cys Ala Lys Leu
             35                  40                  45

Gly Ala Thr Pro Ala Gln Thr Gln Arg His Gln Glu Ala Val Glu Ala
     50                  55                  60

Phe Phe Lys Lys Ile Gly Leu Asp Tyr Gly Lys Glu Val Glu Phe Pro
 65                  70                  75                  80

Ala Phe Val Asn Gly Trp Lys Glu Leu Ala Lys His Asp Leu Lys Leu
                 85                  90                  95

Trp Ser Gln Asn Lys Lys Ser Leu Ile Arg Asn Trp Gly Glu Ala Val
            100                 105                 110

Phe Asp Ile Phe Asp Lys Asp Gly Ser Gly Ser Ile Ser Leu Asp Glu
        115                 120                 125

Trp Lys Thr Tyr Gly Gly Ile Ser Gly Ile Cys Pro Ser Asp Glu Asp
    130                 135                 140

Ala Glu Lys Thr Phe Lys His Cys Asp Leu Asp Asn Ser Gly Lys Leu
145                 150                 155                 160

Asp Val Asp Glu Met Thr Arg Gln His Leu Gly Phe Trp Tyr Thr Leu
                165                 170                 175

Asp Pro Asn Ala Asp Gly Leu Tyr Gly Asn Phe Val Pro
            180                 185

<210> SEQ ID NO 38
<211> LENGTH: 189
<212> TYPE: PRT
<213> ORGANISM: Artificial Sequence
<220> FEATURE:
<223> OTHER INFORMATION: Synthetic Sequence - Obelia longissima Obelin
```

(1QV0

<400> SEQUENCE: 38

Val Lys Leu Lys Thr Asp Phe Asp Asn Pro Arg Trp Ile Lys Arg His
1               5                   10                  15

Lys His Met Phe Asp Phe Leu Asp Ile Asn Gly Asn Gly Lys Ile Thr
            20                  25                  30

Leu Asp Glu Ile Val Ser Lys Ala Ser Asp Asp Ile Cys Ala Lys Leu
        35                  40                  45

Glu Ala Thr Pro Glu Gln Thr Lys Arg His Gln Val Cys Val Glu Ala
    50                  55                  60

Phe Phe Arg Gly Cys Gly Met Glu Tyr Gly Lys Glu Ile Ala Phe Pro
65                  70                  75                  80

Gln Phe Leu Asp Gly Trp Lys Gln Leu Ala Thr Ser Glu Leu Lys Lys
                85                  90                  95

Trp Ala Arg Asn Glu Pro Thr Leu Ile Arg Glu Trp Gly Asp Ala Val
            100                 105                 110

Phe Asp Ile Phe Asp Lys Asp Gly Ser Gly Thr Ile Thr Leu Asp Glu
        115                 120                 125

Trp Lys Ala Tyr Gly Lys Ile Ser Gly Ile Ser Pro Ser Gln Glu Asp
    130                 135                 140

Cys Glu Ala Thr Phe Arg His Cys Asp Leu Asp Asn Ala Gly Asp Leu
145                 150                 155                 160

Asp Val Asp Glu Met Thr Arg Gln His Leu Gly Phe Trp Tyr Thr Leu
                165                 170                 175

Asp Pro Glu Ala Asp Gly Leu Tyr Gly Asn Gly Val Pro
            180                 185

<210> SEQ ID NO 39
<211> LENGTH: 187
<212> TYPE: PRT
<213> ORGANISM: Artificial Sequence
<220> FEATURE:
<223> OTHER INFORMATION: Synthetic Sequence - Aequorea aequorea aequorin
      (1EJ3)

<400> SEQUENCE: 39

Leu Thr Ser Asp Phe Asp Asn Pro Arg Trp Ile Gly Arg His Lys His
1               5                   10                  15

Met Phe Asn Phe Leu Asp Val Asn His Asn Gly Lys Ile Ser Leu Asp
            20                  25                  30

Glu Met Val Tyr Lys Ala Ser Asp Ile Val Ile Asn Asn Leu Gly Ala
        35                  40                  45

Thr Pro Glu Gln Ala Lys Arg His Lys Asp Ala Val Glu Ala Phe Phe
    50                  55                  60

Gly Gly Ala Gly Met Lys Tyr Gly Val Glu Thr Asp Trp Pro Ala Tyr
65                  70                  75                  80

Ile Glu Gly Trp Lys Lys Leu Ala Thr Asp Glu Leu Glu Lys Tyr Ala
                85                  90                  95

Lys Asn Glu Pro Thr Leu Ile Arg Ile Trp Gly Asp Ala Leu Phe Asp
            100                 105                 110

Ile Val Asp Lys Asp Gln Asn Gly Ala Ile Thr Leu Asp Glu Trp Lys
        115                 120                 125

Ala Tyr Thr Lys Ala Ala Gly Ile Ile Gln Ser Ser Glu Asp Cys Glu
    130                 135                 140

Glu Thr Phe Arg Val Cys Asp Ile Asp Glu Ser Gly Gln Leu Asp Val

```
              145                 150                 155                 160
Asp Glu Met Thr Arg Gln His Leu Gly Phe Trp Tyr Thr Met Asp Pro
                        165                 170                 175
Ala Cys Glu Lys Leu Tyr Gly Gly Ala Val Pro
                    180                 185

<210> SEQ ID NO 40
<211> LENGTH: 148
<212> TYPE: PRT
<213> ORGANISM: Artificial Sequence
<220> FEATURE:
<223> OTHER INFORMATION: Synthetic Sequence - Rattus rattus Calmodulin
      (3CLN)

<400> SEQUENCE: 40

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
                20                  25                  30

Gly Thr Val Met Arg Ser Leu Gly Gln Asn Pro Thr Glu Ala Glu Leu
            35                  40                  45

Gln Asp Met Ile Asn Glu Val Asp Ala Asp Gly Asn Gly Thr Ile Asp
        50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Lys Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asn Ile Asp Gly Asp Gly Gln Val Asn Tyr Glu Glu Phe Val Gln Met
    130                 135                 140

Met Thr Ala Lys
145

<210> SEQ ID NO 41
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 41

His His His His His His His
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 42

Thr Glu Asp Glu Asp Glu Asp
1               5

<210> SEQ ID NO 43
<211> LENGTH: 19
<212> TYPE: PRT
```

```
<213> ORGANISM: Artificial Sequence
<220> FEATURE:
<223> OTHER INFORMATION: Synthetic Sequence

<400> SEQUENCE: 43

Glu Asp Met Asn Val Ile Ser Arg Asp Thr Asp Val Asp Ala Asn Arg
1               5                   10                  15

Ala Asp Arg

<210> SEQ ID NO 44
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 44

Ile Gln Ala Gln Val Asp Thr Ile Lys Gly Ala Gly Gly Ser
1               5                   10

<210> SEQ ID NO 45
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 45

Met Gly Val Gln Val Glu Thr Ile Ser Pro Gly Asp Gly Arg Thr Phe
1               5                   10                  15

Pro
```